United States Patent
Shishikura et al.

[11] Patent Number: 6,133,258
[45] Date of Patent: Oct. 17, 2000

[54] INHIBITOR OF KAINIC ACID NEUROTOXICITY AND PYRIDOTHIAZINE DERIVATIVE

[75] Inventors: Jun-ichi Shishikura; Hiroshi Inami; Tomoyuki Yasunaga; Masaaki Hirano; Shuichi Sakamoto; Kazushige Ohno; Masamichi Okada; Shin-ichi Tsukamoto, all of Ibaraki, Japan

[73] Assignee: Yamanouchi Pharmaceutical Co., Ltd., Tokyo, Japan

[21] Appl. No.: 09/068,534

[22] PCT Filed: Nov. 14, 1996

[86] PCT No.: PCT/JP96/03339

§ 371 Date: May 13, 1998

§ 102(e) Date: May 13, 1998

[87] PCT Pub. No.: WO97/17970

PCT Pub. Date: May 22, 1997

[30] Foreign Application Priority Data

Nov. 5, 1995 [JP] Japan .................. 7-296857

[51] Int. Cl.[7] .............. A61K 31/542; C07D 513/04
[52] U.S. Cl. ......................... 514/224.2; 544/48
[58] Field of Search ................. 544/48; 514/224.2

[56] References Cited

PUBLICATIONS

Koscik et. al. Collection Czechoslovek Chem. Commun. 48, 3315–28, 1983.
Zawisa et. al., Pyridothiazines . . . Roczniki Chemii, 49(4), 743–748, 1975.
Koscik et al. collection Czechoslovek Chem. Commun. 48, 3426–32, 1983.
Zawisza et al., Acta Polon. Pharm., 38, 145–152, 1981.
Zawisza et al., Polish Journal of Chemistry, 54, 1875, 1980.
Zawisza et al., I1 Pharmac, 41, 964 (1986).
Zawisza et al., I1 Pharmac, 40, 58 (1985).
Zawisza et al., I1 Pharmac, 40, 65 (1985).
J. Med. Chem., 37, 1616, 1994.
Synthesis, 816, 1988.
Synthesis, 543, 1983.
J. Chem. Soc. Chem. Commun., 561, 1980.

Primary Examiner—Mukund J. Shah
Assistant Examiner—V Balasubramanian
Attorney, Agent, or Firm—Sughrue, Mion, Zinn, Macpeak & Seas, PLLC

[57] ABSTRACT

Neuroprotective agents based on inhibition of kainic acid neurotoxicity and compounds useful as neuroprotective agents based on inhibition of kainic acid neurotoxicity. An inhibitors of kainic acid neurotoxicity, comprising as an active ingredient a pyridothiazine derivative represented by the following general formula (I) or a pharmaceutically acceptable salt thereof, and a pyridothiazine derivative represented by the following general formula (I) or a pharmaceutically acceptable salt thereof:

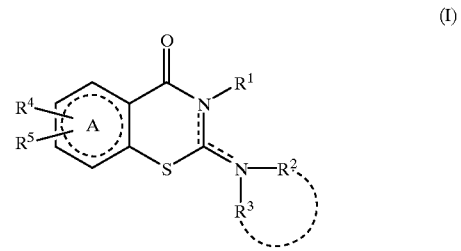

(I)

wherein symbols in the formula have the following respective meanings:

the ring A: a pyridine ring;

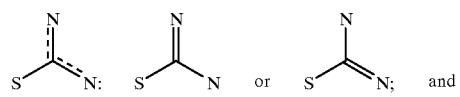

$R^1$, $R^2$, $R^3$, $R^4$ and $R^5$ may be the same or different and each represent a hydrogen atom or a lower alkyl, cycloalkyl, alkenyl, aryl, carboxyl or lower alkoxycarbonyl group which may have substituent(s), or are not present, with the proviso that $R^2$ and $R^3$ may together form a nitrogen-containing heterocyclic group which may have nitrogen atoms as another hetero atom, may be fused with a benzene ring and may have a lower alkyl group as a substituent.

9 Claims, No Drawings

INHIBITOR OF KAINIC ACID NEUROTOXICITY AND PYRIDOTHIAZINE DERIVATIVE

TECHNICAL FIELD

The present invention relates to a potent inhibitor of kainic acid neurotoxicity based on noncompetitive antagonism upon AMPA receptor response, which comprises a pyridothiazine derivative or a salt thereof as an active ingredient. The present invention also relates to a pyridothiazine derivative or a pharmaceutically acceptable salt thereof which has an activity of inhibiting the kainic acid neurotoxicity to provide a neuroprotecting effect, an anti-neurodegeneration effect, an anti-psychiatric diseases effect, an anti-pain effect, and an anti-glaucoma effect.

BACKGROUND OF THE INVENTION

Excitatory amino acids such as L-glutamic acid and L-aspartic acid are known to be central nervous system neurotransmitters. It is believed that excessive excitation by the excitatory amino acids causes neurodegeneration observed in Huntington's chorea, Parkinson's disease, epilepsy, Alzheimer's disease, senile dementia, cerebral ischemia, anoxia, diabetes, hypoglycemia, drug dependence, head injury, etc, which leads to deficiency in mental and motor functions. Therefore, an agent which can control abnormality of the excitatory amino acid function is considered to be useful for protection from the aforementioned neurodegenerative diseases and psychiatric diseases. Further, recent studies show that such an agent is useful also for amyotrophic lateral sclerosis, multiple sclerosis, pain, glaucoma, etc.

Excitatory amino acids exert the effect via specific receptors located in postsynaptic or presynaptic sites. At present, based on electrophysiologic and neurobiochemical evidences, the receptors are classified into the following three groups:

1) NMDA (N-methyl-D-aspartate) receptor;
2) Non-NMDA receptor;
   a) AMPA (2-amino-3-(3-hydroxy-5-methyl-4-isoxazole)propionate)/kainate receptor,
   b) kainate receptor; and
3) Metabotropic glutamate receptor L-glutamic acid or L-aspartic acid activates the aforementioned receptors to transmit excitation.

Exposure to an excess amount of NMDA, AMPA or kainic acid causes neuronal cell death. It has been reported that 2-amino-5-phosphonovaleric acid and 2-amino-7-phosphonoheptanic acid, both of which are selective NMDA antagonists, are protective against NMDA excitotoxicity or in experimental animal models for epilepsy, cerebral ischemia, etc. (*J. Pharmacology and Experimental Therapeutics*, 250, 100 (1989): *J. Pharmacology and Experimental Therapeutics*, 240, 737 (1987): *Science*, 226, 850 (1984)).

It has been reported that the NMDA receptor is under allosteric control by glycine (*Nature*, 325, 529 (1987)).

Glycine exerts its effect via a glycine receptor located on the NMDA receptor. It has been reported that HA-966, which is a glycine antagonist, is effective in an experimental animal model for cerebral ischemia (*Society for Neuroscience*, Annual Meeting Abstract, 1989).

It has also been reported that NBQX (6-nitro-7-sulfamoylbenzo[f]quinoxaline), which is a selective AMPA antagonist, is effective in the experimental animal model for cerebral ischemia (*Science*, 247, 571 (1990)).

It has been reported that the AMPA receptor usually undergoes very rapid desensitization (*Proc. Natl. Acad. Sci. USA*, 85, 2834 (1988)). It is considered that this action protects neurons from excessive excitation by glutamic acid (*Neuron*, 5, 61 (1990)). As a desensitization inhibitor there has been found cyclothiazide (*J. Neurosci.*, 13, 3904 (1993), which has been reported to accelerate AMPA-induced cell death (*J. Neurochem.*, 60, 1171 (1993)). It has also been reported that GYKI52466, which had been known as a noncompetitive AMPA antagonist (*Neurosci. Lett.*, 125, 5 (1993)), counteracts the inhibition of desensitization by cyclothiazide (*Neuron*, 10, 51 (1993)), and that this agent is effective in an experimental animal model for cerebral ischemia (*Stroke*, 23, 861 (1992)).

Some pyridothiazine derivatives have been reported (*Collect. Czech. Chem. Commun.*, 48, (11), 3315 (1983); *Rocz. Chem.*, 49 (4), 748 (1975); *Acta. Polon. Pharm.*, 38 (2), 145 (1981); *Il Farmaco. Ed. Sc.*, 41 (12), 964 (1986)). However, these pyridothiazine derivatives have been merely reported for the anti-serotonin, anti-spasm, antidepressant, and analgesic, and anti-inflammation effects. These pyridothiazine derivatives have never been known to act as noncompetitive antagonists at AMPA receptor and inhibit the kainic acid neurotoxicity.

DISCLOSURE OF THE INVENTION

The present inventors made studies on pyridothiazine derivatives. As a result, they found compounds which exert a higher noncompetitive antagonism upon AMPA receptor response than GYKI52466 and thus provides very potent inhibition of kainic acid neurotoxicity based on the antagonism. Thus, the present invention was accomplished.

An object of the present invention is to provide a medicament comprising an active ingredient a pyridothiazine derivative represented by the following general formula (I) or a pharmaceutically acceptable salt thereof which provides potent inhibition of kainic acid neurotoxicity based on noncompetitive antagonism upon AMPA receptor response and to provide a medicine comprising as an active ingredient the compound (I) of the present invention or a pharmaceutically acceptable salt thereof which provides inhibition of kainic acid neurotoxicity and which is a neuroprotecting agent and an agent for treating neurodegenerative diseases, psychiatric diseases, pain, and glaucoma, particularly a medicine comprising as an active ingredient the compound (I) of the present invention or a pharmaceutically acceptable salt thereof which provides inhibition of kainic acid neurotoxicity and which is an agent for treating Huntington's chorea, Parkinson's disease, epilepsy, Alzheimer's disease, senile dementia, cerebral ischemia, anoxia, diabetes, hypoglycemia, drug dependence, head injury, amyotrophic lateral sclerosis and multiple sclerosis.

The present invention also includes the use of the compound (I) or a pharmaceutically acceptable salt thereof for the preparation of an agent for treating any of these diseases or a method for treating any of these diseases which comprises administering an effective amount of the compound (II) or a pharmaceutically acceptable salt thereof to a patient of any of these diseases.

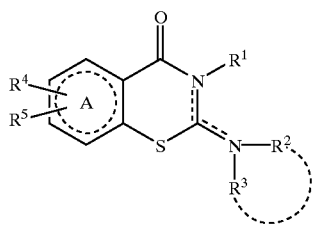
(I)

wherein symbols in the formula have the following respective meanings:

the ring A: a pyridine ring;

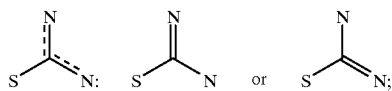

$R^1$ and $R^3$: one of them is not present and the other represents a hydrogen atom or a lower alkyl, lower alkenyl, lower alkynyl or lower alkanoyl group which may have substituent(s);

$R^2$: a group represented by the formula

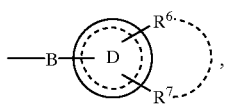

or a mono- or oligocycloalkane which may have a lower alkyl group as a substituent and may have nitrogen atom(s);

B: a bond or a lower alkylene group;

the ring D: a 5- or 6-membered aromatic ring which may have one or two of one or more types of hetero atoms selected from the group consisting of a nitrogen atom, an oxygen atom and a sulfur atom;

$R^6$ and $R^7$: may be the same or different and each represent a hydrogen atom, a lower alkyl group which may have substituent(s), a lower alkanoyl group, a cycloalkyl group, an aryl group, a hydroxyl group, a lower alkoxy group, a halogeno-lower alkoxy group, a carboxyl group, a lower alkoxycarbonyl group, a halogen atom, a nitro group, a cyano group, an amino group, a mono- or di-lower alkylamino group, a hydroxylamino group or a lower alkoxyamino group, with the proviso that $R^6$ and $R^7$ may together form a 5- to 7-membered ring which may have one or two of one or more types of hetero atoms selected from the group consisting of a nitrogen atom, an oxygen atom and a sulfur atom and may have a lower alkyl group as a substituent);

with the proviso that $R^2$ and $R^3$ may together form a 5- to 7-membered nitrogen-containing heterocyclic group which may have a nitrogen atom as another hetero atom, may be fused with a benzene ring which may have substituent(s) and may have substituent(s); and $R^4$ and $R^5$: may be the same or different and each represent a hydrogen atom, a lower alkyl group, a carboxyl group, a lower alkoxycarbonyl group or an aryl group.

Another object of the present invention is to provide a pyridothiazine derivative represented by the following general formula (II) or a pharmaceutically acceptable salt thereof or to provide a pharmaceutical composition comprising a compound (II) of the present invention or a pharmaceutically acceptable salt thereof and a pharmaceutically acceptable carrier.

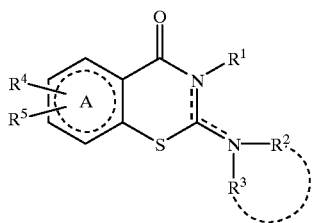
(II)

wherein symbols in the formula have the following respective meanings:

the ring A: a pyridine ring;

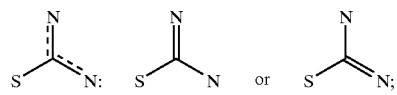

$R^1$ and $R^3$: one of them is not present and the other represents a lower alkyl, lower alkenyl, lower alkynyl or lower alkanoyl group which may have substituent(s);

$R^2$: a group represented by the formula

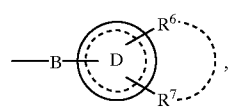

or a mono- or oligocycloalkane which may have a lower alkyl group as a substituent and may have nitrogen atom(s);

B: a bond or lower alkylene group;

the ring D: a 5- or 6-membered aromatic ring which may have one or two of one or more types of hetero atoms selected from the group consisting of a nitrogen atom, an oxygen atom and a sulfur atom;

$R^6$ and $R^7$: may be the same or different and each represent a hydrogen atom, a lower alkyl group which may have substituent(s), a lower alkanoyl group, a cycloalkyl group, an aryl group, a hydroxyl group, a lower alkoxy group, a halogeno-lower alkoxy group, a carboxyl group, a lower alkoxycarbonyl group, a halogen atom, a nitro group, a cyano group, an amino group, a mono- or di-lower alkylamino group, a hydroxylamino group or a lower alkoxyamino group, with the proviso that $R^6$ and $R^7$ may together form a 5- to 7-membered ring which may have one or two of one or more types of hetero atoms selected from the group consisting of a nitrogen atom, an oxygen atom and a sulfur atom and may have a lower alkyl group as a substituent);

with the proviso that $R^2$ and $R^3$ may together form (1) a 5- to 7-membered nitrogen-containing heterocyclic group which may have substituent(s) and which may have a nitrogen atom as another hetero atom, or (2) a 5- to 7-membered nitrogen-containing heterocyclic group which may be fused with a benzene ring which may have substituent(s), which may have a nitrogen atom as another hetero atom, and which may have substituent(s); and R⁴ and R⁵ may be the same or different and each represent a hydrogen atom, a lower alkyl group, a carboxyl group, a lower alkoxycarbonyl group or an aryl group; with the proviso that when one of R¹ and R³ is a methyl group and B is a bond, one of R⁶ and R⁷ represents a group other than a hydrogen atom.

Preferred examples of the present invention is the compound (II) wherein R² is a group represented by the formula

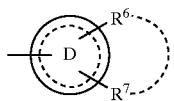

and one of R¹ and R³ is not present and the other represents a lower alkyl group which may have substituent(s), more preferably, those wherein the group

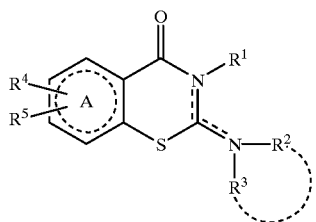

is a group represented by

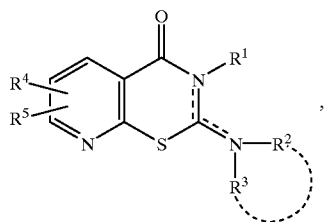

even more preferably, those R² is a group represented by the formula

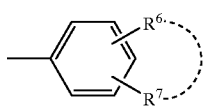

Particularly preferred examples of the present invention include 2-[N-methyl-N-(4-chlorophenyl)amino]-4H-pyrido[3,2-e]-1,3-thiazin-4-one or a pharmaceutically acceptable salt thereof; 2-[N-methyl-N-(3-methylphenyl)amino]-4H-pyrido[3,2-e]-1,3-thiazin-4-one or a pharmaceutically acceptable salt thereof; 2-[N-methyl-N-(4-bromophenyl)amino]-4H-pyrido[3,2-e]-1,3-thiazin-4-one or a pharmaceutically acceptable salt thereof; 2-[N-ethyl-N-(3,4-methylenedioxyphenyl)amino]-4H-pyrido[3,2-e]-1,3-thiazin-4-one or a pharmaceutically acceptable salt thereof; 2-[N-methyl-N-(4-trifluoromethoxylphenyl)amino]-4H-pyrido[3,2-e]-1,3-thiazin-4-one or a pharmaceutically acceptable salt thereof; 2-[N-(4-chlorophenyl)-N-(4-oxo-4H-pyrido[3,2-e]-1,3-thiazin-2-yl)amino]acetonitrile or a pharmaceutically acceptable salt thereof; and 2-[N-(4-chlorophenyl)imino]-3-(2,3-dihydroxypropyl)-2,3-dihydro-4H-pyrido[3,2-e]-1,3-thiazin-4-one or a pharmaceutically acceptable salt thereof.

The aforementioned general formulae (I) and (II) will be further described hereinafter.

The term "lower" as used in the general formulae herein is meant to indicate a $C_{1-6}$ straight or branched carbon chain unless otherwise specified.

Specific examples of the "lower alkyl group" include a methyl group, an ethyl group, a propyl group, an isopropyl group, a butyl group, an isobutyl group, a sec-butyl group, a tert-butyl group, a pentyl(amyl) group, an isopentyl group, a neopentyl group, a tert-pentyl group, a hexyl group, and an isohexyl group. Preferred among these groups are a methyl group, an ethyl group, a propyl group, and an isopropyl group. Particularly preferred among these groups are a methyl group and an ethyl group.

Specific examples of the "lower alkenyl group" include a vinyl group, a 1-propenyl group, an allyl group, an isopropenyl group, a 1-butenyl group, a 2-butenyl group, a 3-butenyl group, a 2-buten-2-yl group, a 2-methyl-1-propenyl group, a 3-buten-2-yl group, a 2-methyl-2-propenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, and a 5-hexenyl group. Preferred among these groups are an allyl group and a 2-butenyl group. Particularly preferred among these groups is an allyl group.

Specific examples of the "lower alkynyl group" include an ethynyl group, a 1-propynyl group, a 2-propynyl group, a 1-methylethynyl group, a 1-butynyl group, a 2-butynyl group, a 3-butynyl group, a 2-butyn-2-yl group, a 2-methyl-1-propynyl group, a 3-butyn-2-yl group, a 2-methyl-2-propynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, and a 5-hexynyl group. Preferred among these groups are an ethynyl group, a 2-propynyl group, and a 2-butynyl group. Particularly preferred among these groups is a 2-propynyl group.

Specific examples of the "lower alkanoyl group" include a formyl group, an acetyl group, a propionyl group, a butyryl group, an isobutyryl group, a valeryl group, an isovaleryl group, a pivaloyl group, and a hexanonyl group. Preferred among these groups is an acetyl group.

The term "mono- or oligocycloalkane which may have nitrogen atom(s)" as used herein is meant to indicate a monocyclic, bicyclic or tricyclic bridged hydrocarbon ring group having from 4 to 16 ring-forming atoms or an aza-cyclo ring obtained by replacing arbitrary carbon atom(s) in the hydrocarbon ring group by nitrogen atom(s). Specific examples of such a group include cyclobutane, cyclopentane, cyclohexane, cycloheptane, bicyclo[2,1,1]hexane, bicyclo[3,1,1]heptane, bicyclo[2,2,2]octane, bicyclo[3,2,1]octane, bicyclo[3,2,2]nonane, bicyclo[3,3,1]nonane, bicyclo[4,3,1]decane, norbornane, adamantane, tricyclo[3,3,1,1³,⁷]decane, azetidine, pyrrolidine, piperidine, piperazine, hexahydroazepine, octahydroazocin, nonahydroazonin, quinuclidine, and diazabicycloundecene. Preferred among these groups are cyclopentane, cyclohexane, cycloheptane, norbornane, pyrrolidine, piperidine, piperazine, hexahydroazepine, and quinuclidine. Particularly preferred among these groups are cyclohexane, norbornane, and piperidine.

Specific examples of the "lower alkylene group" include a methylene group, an ethylene group, an ethylidene group, a propylidene group, a methylethylene group, a propylene group, a butylene group, a pentylene group, and a hexylene group. Preferred among these groups are a methylene group and an ethylene group. Particularly preferred among these groups is a methylene group.

Specific examples of the "5- or 6-membered aromatic ring which may have one or two of one or more types of hetero atoms selected from the group consisting of a nitrogen atom, an oxygen atom or a sulfur atom" include pyrrole, imidazole, furan, oxazole, isoxazole, thiophene, thiazole, isothiazole, pyridine, pyridazine, pyrimidine, and pyrazine. Preferred among these rings are pyrrole, furan, thiophene, and pyridine. Particularly preferred among these rings are thiophene and pyridine.

The term "cycloalkyl group" as used herein is meant to indicate a hydrocarbon ring group having from 3 to 8 ring-forming atoms. Specific examples of the cycloalkyl group include a cyclopropyl group, a cyclobutyl group, a cyclopentyl group, a cyclohexyl group, a cycloheptyl group, and a cyclooctyl group. Preferred among these groups are a cyclopentyl group, a cyclohexyl group, and a cycloheptyl group. Particularly preferred among these groups is a cyclohexyl group.

The term "aryl group" as used herein is meant to indicate a carbocyclic aryl group. Specific examples of the carbocyclic aryl group include a phenyl group, a tolyl group, a xylyl group, a biphenyl group, a naphthyl group, an anthryl group, and a phenanthryl group. Preferred among these groups are a phenyl group and a naphthyl group. Particularly preferred among these groups is a phenyl group.

Specific examples of the "lower alkoxy group" include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a 1-methylbutoxy group, a 2-methylbutoxy group, a 1,2-dimethylpropoxy group, a hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2 -trimethylpropoxy group, a 1-ethyl-1-methylpropoxy group, and a 1-ethyl-2-methylpropoxy group. Preferred among these groups are a methoxy group, an ethoxy group, a propoxy group, an isopropoxy group, a butoxy group, an isobutoxy group, a sec-butoxy group, and a tert-butoxy group. Particularly preferred among these groups is a methoxy group.

Specific examples of the "lower alkoxycarbonyl group" include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxy carbonyl group, a tert-pentyloxycarbonyl group, a 1-methylbutoxycarbonyl group, a 2-methylbutoxycarbonyl group, a 1,2-dimethylpropoxycarbonyl group, a hexyloxycarbonyl group, an isohexyloxycarbonyl group, a 1-methylpentyloxycarbonyl group, a 2-methylpentyloxycarbonyl group, a 3-methylpentyloxycarbonyl group, a 1,1-dimethylbutoxycarbonyl group, a 1,2-dimethylbutoxycarbonyl group, a 2,2-dimethylbutoxycarbonyl group, a 1,3-dimethylbutoxycarbonyl group, a 2,3-dimethylbutoxycarbonyl group, a 3,3-dimethylbutoxy carbonyl group, a 1-ethylbutoxycarbonyl group, a 2-ethylbutoxycarbonyl group, a 1,1,2-trimethylpropoxycarbonyl group, a 1,2,2-trimethylpropoxycarbonyl group, a 1-ethyl-1-methylpropoxycarbonyl group, and a 1-ethyl-2 -methylpropoxycarbonyl group. Preferred among these groups are a methoxycarbonyl group, an ethoxycarbonyl group, a propoxycarbonyl group, and an isopropoxycarbonyl group. Particularly preferred among these groups is an ethoxycarbonyl group.

The term "halogeno-lower alkoxy group" as used herein is meant to indicate the lower alkoxy group which is substituted by halogen atom(s) in an arbitrary position. Specific examples of the halogeno-lower alkoxy group include a fluoromethoxy group, a chloromethoxy group, a bromomethoxy group, a difluoromethoxy group, a dichloromethoxy group, a dibromomethoxy group, a trifluoromethoxy group, a trichloromethoxy group, a tribromomethoxy group, a 1-f luoroethoxy group, a 2-fluoroethoxy group, a 1-chloroethoxy group, a 2-chloroethoxy group, a 1-bromoethoxy group, a 2-bromoethoxy group, a 1,1-difluoroethoxy group, a 1,2-difluoroethoxy group, a 2,2-difluoroethoxy group, a 1,1-dichloroethoxy group, a 1,2-dichloroethoxy group, a 2,2-dichloroethoxy group, a 1,1-dibromoethoxy group, a 1,2-dibromoethoxy group, a 2,2-dibromoethoxy group, a 1,1,2-trifluoroethoxy group, a 1,2,2-trifluoroethoxy group, a 2,2,2-trifluoroethoxy group, a ,1,2-trichloroethoxy group, a 1,2,2-trichloroethoxy group, a 2,2,2-trichloroethoxy group, a 1,122-tribromoethoxy group, a 1,2,2-tribromoethoxy group, and a 2,2,2-tri bromoethoxy group. Preferred among these group s are a trifluoromethoxy group, a trichloromethoxy group, and a tribromomethoxy group. Particularly preferred among these groups is a trifluoromethoxy group.

Specific examples of the "halogen atom" include a fluorine atom, a chlorine atom, a bromine atom, and an iodine atom. Preferred among these halogen atoms are a chlorine atom and a bromine atom. Particularly preferred halogen atom is a chlorine atom.

The term "mono- or di-lower alkylamino group" as used herein is meant to indicate an amino group substituted by one or two of the aforementioned lower alkyl group(s). Specific examples of the mono- or di-lower alkylamino group include a methylamino group, an ethylamino group, a propylamino group, an isopropylamino group, a dimethylamino group, a diethylamino group, a dipropylamino group, and a diisopropylamino group. Preferred among these groups are a dimethylamino group and a diethylamino group.

Specific examples of the "lower alkoxyamino group" include a methoxyamino group, an ethoxyamino group, a propoxyamino group, an isopropoxyamino group, a butoxyamino group, an isobutoxyamino group, a sec-butoxyamino group, a tert-butoxyamino group, a pentyloxyamino group, an isopentyloxyamino group, a neopentyloxyamino group, a tert-pentyloxyamino group, a 1-methylbutoxyamino group, a 2-methylbutoxyamino group, a 1,2-dimethylpropoxyamino group, a hexyloxyamino group, an isohexyloxyamino group, a 1-methylpentyloxyamino group, a 2-methylpentyloxyamino group, a 3-methylpentyloxyamino group, a 1,1-dimethylbutoxyamino group, a 1,2-dimethylbutoxyamino group, a 2,2-dimethylbutoxyamino group, a 1,3-dimethylbutoxyamino group, a 2,3-dimethylbutoxyamino group, a 3,3-dimethylbutoxyamino group, a 1-ethylbutoxyamino group, a 2-ethylbutoxyamino group, a 1,1,2-trimethylpropoxyamino group, a 1,2,2- trimethylpropoxyamino group, a 1-ethyl-1-methylpropoxyamino group, and a 1-ethyl-2-methylpropoxyamino group. Preferred among these groups are a methoxyamino group and an ethoxyamino group.

Specific examples of the "5- to 7-membered ring formed by $R^6$ and $R^7$ which may have one or two of one or more types of hetero atoms selected from the group consisting of a nitrogen atom, an oxygen atom and a sulfur atom and may have a lower alkyl group as a substituent" include cyclopentene, cyclopentadiene, benzene, cyclohexene, cyclohexadiene, cycloheptene, cycloheptadiene, cycloheptatoluene, pyrrole, pyrroline, imidazole, imidazoline, triazole, triazoline, pyridine, dihydropyridine, tetrahydropyridine, pyridazine, pyrimidine, pyrazine, triazine, azacycloheptene, azacycloheptadiene, furan, dihydrofuran, pyran, dihydropyran, dioxol, dioxin, dihydrodioxin, thiophene, dihydrothiophene, oxazole, oxazoline, isoxazole, oxadiazole, thiazole, isothiazole, and thiadiazole. Preferred among these rings are benzene, cyclopentene, cycloheptene, furan, dihydrofuran, dioxol, dihydrodioxin, thiophene, dihydrothiophene, thiazole, pyridine, and dihydropyridine. Particularly preferred among these rings are benzene, cyclopentene, dioxol, dihydrodioxin, thiazole, and pyridine.

Specific examples of the "5- to 7-membered nitrogen-containing heterocyclic group formed by $R^2$ and $R^3$ which may have a nitrogen atom as another hetero atom, may be fused with a benzene ring which may have substituent(s) and may have substituent(s)" include pyrrole, pyrroline, pyrrolidine, imidazole, imidazoline, imidazolidine, pyridine, dihydropyridine, tetrahydropyridine, piperidine, pyridazine, dihydropyridazine, pyrimidine, dihydropyrimidine, tetrahydropyrimidine, pyrazine, dihydropyrazine, piperazine, homopiperazine, azepine, hexahydroazepine, indole, indoline, isoindole, isoindoline, benzimidazole, quinoline, dihydroquinoline, tetrahydroquinone, isoquinoline, dihydroisoquinoline, tetrahydroisoquinoline, tetrahydroquinoxaline, benzazepine, dihydrobenzazepine, dihydrobenzazepine, tetrahydrobenzazepine, and benzodiazepine. Preferred among these groups are dihydropyridine, piperidine, dihydropyrazine, piperazine, indoline, isoindoline, dihydroquinoline, tetrahydroquinoline, dihydroisoquinoline, tetrahydroisoquinoline, benzazepine, and dihydrobenzazepine. Particularly preferred among these groups are dihydropyridine, piperidine, piperazine, indoline, isoindoline, tetrahydroquinoline, tetrahydroisoquinoline, and tetrahydroazepine. Examples of the substituents on the nitrogen-containing heterocyclic group include a lower alkyl group, a hydroxyl group, a lower alkoxy group, a carboxyl group, a lower alkoxycarbonyl group, an oxo group, and a phenyl group which may have a lower alkyl group, a hydroxyl group or a lower alkoxy group as substituent(s). One or two of these substituents may be used. Preferred among these substituents are a methyl group, an ethyl group, a hydroxyl group, a methoxy group, an ethoxy group, a carboxyl group, a methoxycarbonyl group, an ethoxycarbonyl group, an oxo group, and a phenyl group which may have lower alkoxy group as substituent(s). Particularly preferred among these substituents are a methyl group, a hydroxyl group, an ethoxycarbonyl group, an oxo group, and a phenyl group which may have a methoxy group. Examples of the substituents on the benzene ring include a lower alkyl group, a halogen atom, a hydroxyl group, and a lower alkoxy group. One or two of these substituents may be used. Preferred among these substituents are a methyl group, an ethyl group, a chlorine atom, and a bromine atom. Particularly preferred among these substituents is a bromine atom.

Specific examples of the "5- to 7-membered nitrogen-containing heterocyclic group which may have substituent(s) and which may have a nitrogen atom as another hetero atom" include pyrrole, pyrroline, pyrrolidine, imidazoline, imidazolidine, dihydropyridine, tetrahydropyridine, piperidine, dihydropyridazine, dihydropyrimidine, tetrahydropyrimidine, dihydropyrazine, piperazine, homopiperazine, azepine, and hexahydroazeptine. Preferred among these groups are pyrrolidine, tetrahydropyridine, piperidine, piperazine, and hexahydroazepine. Particularly preferred among these groups are piperidine, piperazine, tetrahydropyridine, and hexahydroazepine. Examples of the substituents include a lower alkyl group, a hydroxyl group, a lower alkoxy group, a carboxyl group, a lower alkoxycarbonyl group, an oxo group, and a phenyl group which may have a lower alkyl group, a hydroxyl group or a lower alkoxy group as substituent(s). One or two of these substituents may be used. Preferred among these substituents are a methyl group, an ethyl group, a hydroxyl group, a methoxy group, an ethoxy group, a carboxyl group, a methoxycarbonyl group, an ethoxycarbonyl group, an oxo group, and a phenyl group which may have a lower alkoxy group as substituent(s). Particularly preferred among these substituents are a methyl group, a hydroxyl group, an ethoxycarbonyl group, an oxo group, and a phenyl which may have methoxy group(s).

Specific examples of the "a 5- to 7-membered nitrogen-containing heterocyclic group which may be fused with a benzene ring which may have substituent(s), which may have a nitrogen atom as another hetero atom, and which may have substituent(s)" include indole, indoline, isoindole, isoindoline, benzimidazole, quinoline, dihydroquinoline, tetrahydroquinoline, isoquinoline, dihydroisoquinoline, tetrahydroisoquinoline, tetrahydroquinoxaline, benzazepine, tetrahydrobenzazepine, and benzodiazepine. Preferred among these groups are indole, indoline, isoindoline, quinoline, tetrahydroquinoline, isoquinoline, tetrahydroisoquinoline, and tetrahydrobenzazepine. Particularly preferred among these groups are indoline, isoindoline, tetrahydroquinoline, tetrahydroisoquinoline, and tetrahydrobenzazepine. Examples of the substituents on the nitrogen-containing heterocyclic group include lower alkyl group. One or two of these substituents may be used. Preferred among these substituents are a methyl group and an ethyl group. Particularly preferred among these substituents is a methyl group. Examples of the substituents on the benzene ring include a lower alkyl group, a halogen atom, a hydroxyl group, and a lower alkoxy group. One or two of these substituents may be used. Preferred among these substituents are a methyl group, an ethyl group, a chlorine atom, and a bromine atom. Particularly preferred among these substituents is a bromine atom.

Specific examples of the "substituent(s)" on "the lower alkyl group which may have substituent(s)" include a cyano group, an oxo group, a carboxyl group, a lower alkoxycarbonyl group, a carbamoyl group, a mono- or di-lower alkylcarbamoyl group, a hydroxyl group, a lower alkoxy group, a lower alkanoyloxy group, an amino group, a mono- or di-lower alkylamino group, an aryl group which may have one or two lower alkyl, hydroxyl, lower alkoxy, halogeno, or oxo groups as substituent(s), and 5- or 6-membered aromatic ring which may have 1 to 4 hetero atoms selected from the group consisting of a nitrogen atom, an oxygen atom and a sulfur atom and may be fused with a benzene ring. One or two of these substituents may be used. Preferred among these substituents are a cyano group, an oxo group, a carboxyl group, an ethoxycarbonyl group, a carbamoyl group, a hydroxyl group, a methoxy group, an acetyloxy group, an amino group, a dimethylamino group, a diethylamino group, a tetrazolyl group, a halogenothienyl group, a dioxalanyl group, a phthaloyl group, a lower alkoxyphenyl group, and a pyridyl group. Particularly preferred among these substituents are a cyano group, a hydroxyl group, an oxo group, and a pyridyl group.

Specific examples of the "lower alkanoyloxy group" include an acetyloxy group, a propionyloxy group, a butyryloxy group, an isobutyryloxy group, a valeryloxy group, an isovaleryloxy group, a pivaloyloxy group, and a hexanoyloxy group. Preferred among these groups are an acetyloxy group and a propionyloxy group. Particularly preferred among these groups is an acetyloxy group.

The term "mono- or di-lower alkylcarbamoyl group" as used herein is meant to indicate a carbamoyl group substituted by one or two of the aforementioned lower alkyl group(s). Specific examples of the carbamoyl group include a methylcarbamoyl group, an ethylcarbamoyl group, a propylcarbamoyl group, an isopropylcarbamoyl group, a dimethylcarbamoyl group, a diethylcarbamoyl group, a dipropylcarbamoyl group, and a diisopropylcarbamoyl group. Preferred among these groups are a dimethylcarbamoyl group and a diethylcarbamoyl group.

Specific examples of the "5- or 6-membered heterocyclic group which may have 1 to 4 hetero atoms selected from the group consisting of a nitrogen atom, an oxygen atom and a sulfur atom and may be fused with a benzene ring" include pyrrole, pyrrolidine, imidazole, triazole, tetrazole, pyridine, pyridazine, pyrimidine, pyrazine, triazine, furan, tetrahydrofuran, dioxolane, dioxane, thiophene, indole, indoline, isoindoline, benzimidazole, benzotriazole, quinoline, benzofuran, and benzothiophene. Preferred among these groups are pyrrole, imidazole, triazole, tetrazole, dioxolane, dioxane, thiophene, pyridine, indoline, and isoindoline. Particularly preferred among these groups are tetrazole, dioxolane, thiophene, and pyridine.

The compounds (I) and (II) of the present invention occur in the form of tautomers arising from pyridothiazine skeleton. Accordingly, The compounds (I) and (II) wherein $R^1$ is a hydrogen atom are the same as those wherein $R^3$ is a hydrogen atom.

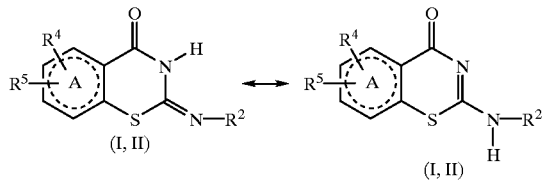

The compounds (I) and (II) of the present invention may have an asymmetric carbon atom or double bond depending on the kind of substituents. Accordingly, the compounds (I) and (II) of the present invention have various isomers such as optical isomer and geometrical isomer (e.g., cis isomer, trans isomer) as a mixture or isolated ones.

The compounds (I) and (II) form a salt with an acid. Examples of such a salt include acid addition salts with inorganic acids such as hydrochloric acid, hydrobromic acid, hydroiodic acid, sulfuric acid, nitric acid and phosphoric acid; organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid and ethanesulfonic acid; or acidic amino acids such as aspartic acid and glutamic acid.

Further, the compounds (I) and (II) or salts thereof of the present invention may be isolated in the form of various solvates such as hydrate and ethanolated material or polymorphic material thereof. Therefore, the present invention contains these hydrates, solvates or polymorphic materials thereof.

(Preparation method)

The compound of the present invention can be prepared by various synthesis methods using the characteristics based on the kind of its basic skeleton or substituents. Representative preparation methods will be given below.

(1st preparation method)

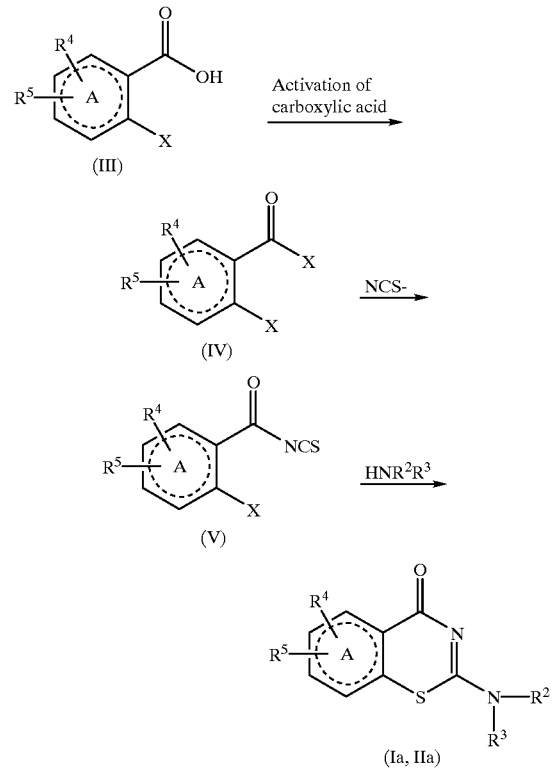

(wherein $R^2$, $R^3$, $R^4$ and $R^5$ are as defined above, and X represents a leaving group such as tosyloxy group, mesyloxy group, trifluoromethanesulfonyloxy group and a halogen atom.)

The carboxyl group in the starting material (III) can be activated to synthesize an active intermediate product (IV) which is then reacted with a thiocyanate to prepare an acylisothiocyanate (V). The acylisothiocyanate (V) can then be reacted with a primary or secondary amine to prepare a compound (Ia) or (IIa) of the present invention.

The active intermediate product (IV) can be prepared by the reaction of the starting material (III) with thionyl chloride, phosphorous oxychloride, phosphorus pentachloride, tosyl chloride, mesyl chloride, trifluoromethanesulfonyl chloride or the like. The reaction may be effected in the presence of an organic solvent which is inert to the reaction, such as methylene chloride, benzene, tetrahydrofuran (THF), ether, acetone and dimethyl sulfoxide (DMSO). Alternatively, the reaction may be effected without solvent. The reaction may be accelerated by the use of dimethyl formamide (DMF), tertiary amine or the like. Further, the reaction may be effected at a temperature of 0° C. to elevated temperatures.

Examples of the thiocyanate to be used in the preparation of the acylisothiocyanate (V) include ammonium thiocyanate, sodium thiocyanate, and potassium thiocyanate. The reaction may be effected in the presence of an organic solvent which is inert to the reaction, such as methylene chloride, benzene, THF, ether, acetone and DMSO. Further, the reaction may be effected at a temperature of 0° C. to elevated temperatures.

The reaction for the preparation of the compound (Ia) or (IIa) may be effected in the presence of an organic solvent such as methylene chloride, benzene, THF, ether, acetone and DMSO. Further, the reaction may be effected at a temperature of 0° C. to elevated temperatures.

(2nd preparation method)

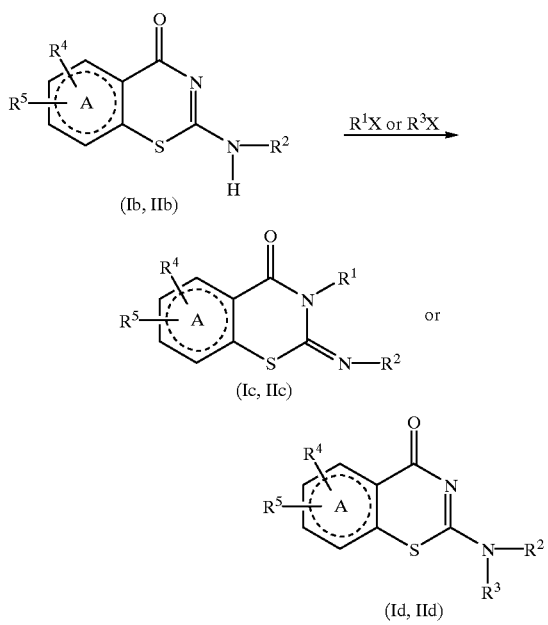

(wherein $R^1$, $R^2$, $R^3$, $R^4$, $R^5$ and X are as defined above.)

The compound (Ib) or (IIb), which is a compound of the present invention obtained by the 1st preparation method wherein $R^3$ is a hydrogen atom, can be reacted with an alkylating agent ($R^1X$ or $R^3X$) in the presence of a base to prepare the compound (Id) or (IId) of the present invention.

Examples of the base to be used in the aforementioned reaction include lithium hydride, sodium hydride, potassium hydride, butyllithium, and lithium isopropylamide. The reaction may be effected in the presence of an organic solvent which is inert to the reaction, such as methylene chloride, benzene, THF, ether, acetone and DMSO. Further, the reaction may be effected at a temperature of 0° C. to elevated temperatures.

(3rd preparation method)

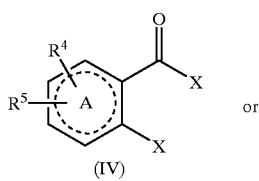

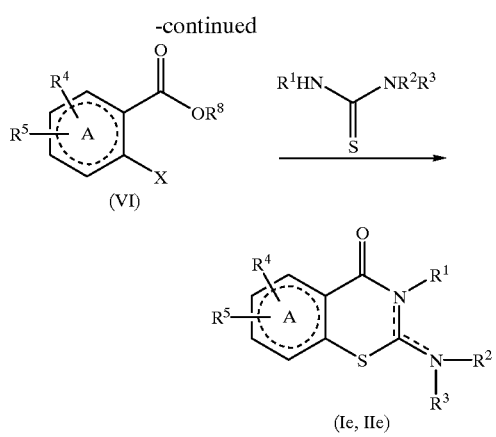

(wherein $R^1$, $R^2$, $R^3$, $R^4$, $R^5$ and X are as defined above; and $R^8$ represents a lower alkyl group.) The active intermediate product (IV) or nicotinic acid ester derivative (VI) can be reacted with a thiourea derivative to prepare the compound (Ie) or (IIe) of the present invention. The reaction may be effected in the presence of an organic solvent which is inert to the reaction, such as methylene chloride, benzene, THF, ether, acetone, DMSO, ethanol and methanol. Further, the reaction may be effected at a temperature of 0° C. to elevated temperatures.

The compound (I) or (II) of the present invention thus prepared is isolated and purified as a free compound or as salt, hydrate, solvate or polymorphic material. The salt of the compound (I) or (II) of the present invention can be prepared by subjecting the compound (I) or (II) to ordinary salt-forming reaction.

The isolation and purification can be accomplished by an ordinary chemical operation such as extraction, concentration, distillation, crystallization, filtration, recrystallization and various types of chromatography.

The various isomers can be isolated by properly selecting starting compounds or making the use of difference in physical properties between isomers. For example, an optical isomer can be led to a stereochemically pure isomer by properly selecting starting materials or by optical resolution of racemic compound (e.g., involving the conversion to a diastereomer salt with an ordinary optically active acid or base which is then subjected to optical resolution).

Besides the compounds described in the following examples, the following compounds can be obtained without any special experiments by the use of the aforementioned preparation methods, the preparation methods described in the following examples and modified preparation methods known to those skilled in the art.

2-[N-(4-bromophenyl)-N-(2-propynyl)amino]-4H-pyrido[3,2-e]-1,3-thiazin-4-one

2-[N-(4-bromophenyl)-N-(1H-tetrazol-5-ylmethyl)amino]-4H-pyrido[3,2-e]-1,3-thiazin-4-one 2-[N-(4-bromophenyl)-N-(4-oxo-4H-pyrido[3,2-e]-1,3-thiazin-2-yl)amino]acetonitrile 2-[N-(3,4-methylenedioxyphenyl)-N-(2-propynyl)amino]-4H-pyrido[3,2-e]-1,3-thiazin-4-one 2-[N-(3,4-methylenedioxyphenyl)-N-(1H-tetrazol-5-ylmethyl)amino]-4H-pyrido[3,2-e]-1,3-thiazin-4-one 2-[N-(3,4-methylenedioxyphenyl)-N-(4-oxo-4H-pyrido[3,2-e]-1,3-thiazin-2-yl)amino]acetonitrile 2-[N-(3,4-ethylenedioxyphenyl)-N-(2-propynyl)amino]-4H-pyrido[3,2-e]-1,3-thiazin-4-one 2-[N-(3,4-ethylenedioxyphenyl)-N-(1H-tetrazol-5-ylmethyl)amino]-4H-pyrido[3,2-e]-1,3-thiazin-4-one N-(3,4-ethylenedioxyphenyl)-N-(4-oxo-4H-pyrido[3,2-e]-1,3-thiazin-2-yl)-2-aminoacetonitrile 2-[N-(benzo[b]thiophen-5-yl)-N-(2-propynyl)amino]-4H-pyrido[3,2-e]-1,3-thiazin-4-one 2-[N-(benzo[b]thiophen-5-yl)-N-(1H-tetrazol-5-ylmethyl)amino]-4H-pyrido[3,2-e]-1,3-thiazin-4-one N-(benzo[b]thiophen-5-yl)-N-(4-oxo-4H-pyrido[3,2-e]-1,3-thiazin-2-yl)-2-aminoacetonitrile 2-[N-(2-propynyl)-N-(quinoxalin-6-yl)amino]-4H-pyrido[3,2-e]-1,3-thiazin-5-one 2-[N-methyl-N-(quinoxalin-6-yl)amino]-4H-pyrido[3,2-e]-1,3-thiazin-4-one 2-[N-(quinoxalin-6-yl)-N-(1H-tetrazol-5-ylmethyl)amino]-4H-pyrido[3,2-e]-1,3-thiazin-4-one 2-[N-(quinoxalin-6-yl)-N-(4-oxo-4H-pyrido[3,2-e]-1,3-thiazin-2-yl)amino]acetonitrile 2-[N-(benzo[b]furan-5-yl)-N-(2-propynyl)amino-4H-pyrido[3,2-e]-1,3-thiazin-4-one 2-[N-(benzo[b]furan-5-yl)-N-methylamino]-4H-pyrido[3,2-e]-1,3-thiazin-4-one 2-[N-(benzo[b]furan-5-yl)-N-(1H-tetrazol-5-ylmethyl)amino]-4H-pyrido[3,2-e]-1,3-thiazin-4-one 2-[N-(benzo[b]furan-5-yl)-N-(4-oxo-4H-pyrido[3,2-e]-1,3-thiazin-2-yl)-2-amino]acetonitrile 2-[N-(1-methylindol-5-yl)-N-(2-propynyl)amino]-4H-pyrido[3,2-e]-1,3-thiazin-4-one 2-[N-methyl-N-(1-methylindol-5-yl)amino]-4H-pyrido[3,2-e]-1,3-thiazin-4-one 2-[N-(1-methylindol-5-yl)-N-(1H-tetrazol-5-ylmethyl)amino]-4H-pyrido[3,2-e]-1,3-thiazin-4-one 2-[N-(1-methylindol-5-yl)-N-(4-oxo-4H-pyrido[3,2-e]-1,3-thiazin-2-yl)-2-amino]acetonitrile 2-(1,2,3,4-tetrahydro-1,5-benzo[b]oxazepin-1-yl)-4H-pyrido[3,2-e]-1,3-thiazin-4-one 2-[N-(4-chlorophenyl)-N-methylamino]-4H-pyrido[2,3-e]thiazin-4-one 2-[N-(4-chlorophenyl)-N-[2-(1H-imidazol-1-yl)ethyl]amino]-4H-pyrido[2,3-e]thiazin-4-one 2-[N-(4-chlorophenyl)-N-[(1H-imidazol-5-yl)methyl]amino]-4H-pyrido[2,3-e]thiazin-4-one

INDUSTRIAL APPLICABILITY

The compound of the present invention exerts a noncompetitive antagonism upon AMPA receptor response, and provides potent inhibitory action against kainic acid neurotoxicity and anticonvulsant effect for audiogenic seizure in DBA/2 mouse.

Accordingly, the compound of the present invention is a medicine particularly useful for prevention or treatment of Huntington's chorea, Parkinson's disease, epilepsy, Alzheimer's disease, senile dementia, cerebral ischemia, anoxia, diabetes, hypoglycemia, drug dependence, head injury, amyotrophic lateral sclerosis and multiple sclerosis.

The inhibition of kainic acid neurotoxicity and anticonvulsant effect for audiogenic seizure in DBA/2 mice by the compound of the present invention was confirmed as follows:

1) Inhibition of kainic acid neurotoxicity

The effect of the compound of the present invention for inhibiting kainic acid neurotoxicity was studied using primary rat hippocampal cultures.

(1) Incubation conditions

The hippocampus was dissected from a brain of the 18 to 20-day-old fetal rat and was subjected to enzyme treatment with papain and DNase I to disperse the cells. The cells so obtained were suspended in MEM containing 10% serum and plated on poly-L-lysine coated 48-well plates at a density of $4 \times 10^5$ cells/cm$^2$. Twenty four hours later, the medium was replaced by a serum-free medium. The medium was changed twice a week. The cells which were cultured for at least 6 days were provided for the following test.

(2) Inhibition against kainic acid neurotoxicity

Neurotoxicity was assessed by an activity of lactate dehydrogenase released into the culture medium from destroyed cells. As a control, neurons which were exposed to a serum-free medium containing 300 $\mu$M kainic acid for 24 hours were used. Each compound, together with 300 $\mu$M kainic acid, was allowed to act on the neuron for 24 hours and inhibitory action of each compound against kainic acid neurotoxicity was evaluated.

As a result, these compounds each exhibit inhibition of kainic acid neurotoxicity when it occurs in a concentration of not more than 2 $\mu$M as set forth in Table 1.

TABLE 1

Inhibition of kainic acid neurotoxicity

| Example No. | IC$_{50}$ ($\mu$M) |
|---|---|
| 16-2) | 1.0 |
| 64 | 1.4 |
| 72 | 1.9 |

2) Measurement of audiogenic seizure inhibitory action in DBA/2 mice

Ten male 21 to 28-day-old mice were exposed to the sound of 12 kHz and 120 dB in a sound proof box for one minute or until these mice exhibited tonic seizure.

The test compound was suspended in a 0.5% methylcellulose solution and the resulting suspension was intraperitoneally administered 45 minutes before the stimulation by the sound. The drug efficacy was evaluated by presence or absence of the appearance of seizure and the minimum effective dose was determined.

As a result, these compounds exhibited anticonvulsant effect at a dosage of 30 mg/kg, i.p. or less as set forth in Table 2.

TABLE 2

Measurement of anticonvulsant effect for audiogenic seizure in DBA/2 mice

| Example No. | Minimum effective dose (mg/kg, i.p.) |
|---|---|
| 16-2) | 30 |
| 64 | 10 |
| 72 | 30 |

Thus, the compound of the present invention exhibits inhibition of kainic acid neurotoxicity and thus is useful as a neuroprotective agent or an agent for treating neurodegenerative diseases, psychiatric diseases, pain, and glaucoma, particularly, as an agent for treating Huntington's chorea, Parkinson's disease, epilepsy, Alzheimer's disease, senile dementia, cerebral ischemia, anoxia, diabetes, hypoglycemia, drug dependence, head injury, amyotrophic lateral sclerosis and multiple sclerosis.

A pharmaceutical composition comprising as an active ingredient one or more of the compound (I) or (II), a pharmaceutically acceptable salt thereof, a hydrate thereof, a solvate thereof, etc. is prepared by using a carrier, vehicle or other additives commonly used for pharmaceutical preparations in the form of tablet, powder, fine granule, granule, capsule, pill, solution, injection, suppository, ointment, patch, etc. which can be administered orally (including sublingual administration) or parenterally.

The clinical dosage of the compound (I) or (II) of the present invention to human patient can be properly determined case by case taking into account the symptom, weight, age and sex of the patient, administration method, etc. In general, the compound (I) or (II) can be administered at a time or batchwise to an adult orally at a dosage of from 10 mg to 1,000 mg, preferably from 50 mg to 200 mg a day or can be administered at a time or in several times; or continuously for 1 to 24 hours a day to an adult intravenously at a dosage of from 1 mg to 500 mg, preferably from 5 mg to 100 mg. As described above, the dose may vary depending on various conditions, so it is needless to say that the dose smaller than the above range may sometimes be sufficient.

As a solid composition for the oral administration according to the present invention, tablets, powders, granules or the like may be used. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium metasilicate. The composition may contain an additive other than the inactive diluent, for example, a lubricant such as magnesium stearate, disintegrator such as calcium cellulose glycolate, stabilizer such as lactose, or solubilizing agent or solubilizing assistant such as glutamic acid or aspartic acid. The tablet or pill may be coated with a film made of a gastric or enteric substance such as sucrose, gelatin, hydroxypropylcellulose or hydroxypropylmethylcellulose phthalate.

Examples of the liquid composition for the oral administration include a pharmaceutically acceptable emulsion, solution, suspension, syrup or elixir and it contains a generally employed inactive diluent such as purified water or ethanol. In addition to the inactive diluent, the liquid composition may also contain an adjuvant such as solubilizing agent or solubilizing assistant, wetting agent or suspending agent, a sweetener, a flavoring agent, an aroma or an antiseptic.

Examples of the injections for parenteral administration include sterile aqueous or nonaqueous solution, suspension and emulsion. As a diluent for aqueous solution or suspension, injection-grade distilled water and physiological saline are included. Examples of the diluent for nonaqueous solution or suspension include propylene glycol, polyethylene glycol, vegetable oil such as olive oil, alcohol such as ethanol and "Polysolbate 80" (trade name). Such a composition may further contain an additive such as an isotonicity agent, antiseptic, wetting agent, emulsifying agent, dispersing agent, stabilizing agent (e.g., lactose), or solubilizing agent or solubilizing assistant. They are sterilized, for example, by filtration through a bacteria-retaining filter, incorporation of an insecticide, or irradiation. The injection can also be obtained by first preparing a sterile solid composition and then dissolving it in a sterile water or sterile injection-graded solvent upon use.

BEST MODE OF THE PRESENT INVENTION

The present invention will be further described in the following Examples, but the present invention should not be construed as being limited thereto.

EXAMPLE 1

2-(4-Methylanilino)-4H-pyrido[3,2-e]-1,3-thiazin-4-one 1) 1-(2-Chloronicotinoyl)-3-(4-methylphenyl)thiourea A mixture of 7.58 g (48.1 mmol) of 2-chloroniconitic acid, 30 ml of thionyl chloride and two droplets of DMF was heated under reflux in a 200 ml flask for 2 hours. The resulting reaction mixture was allowed to cool, and then concentrated under reduced pressure. The resulting residue was then dissolved in 30 ml of acetone.

A mixture of 3.66 g of ammonium thiocyanate and 50 ml of acetone was stirred in another 200 ml flask. To the flask was then connected a dropping funnel which contained the aforementioned acetone solution of chloronicotinoyl chloride. The acetone solution was then added dropwise to the ammonium thiocyanate solution with stirring, followed by further stirring for 15 minutes.

The insoluble matters which had separated out in the reaction mixture were removed by filtration. The filtrate was then put in a 300 ml flask. To the flask was then connected a dropping funnel which contained a solution of 5.16 g of p-toluidine in 30 ml of acetone. The toluidine solution was then added dropwise to the filtrate with stirring in 5 minutes, followed by further stirring for 15 minutes. The resulting reaction mixture was poured into ice-water in an amount of 20 or more times that of the reaction mixture. The resulting precipitate was collected by filtration, washed with water, and then dried under reduced pressure to obtain 13.9 g of 1-(2-chloronicotinoyl)-3-(4-methylphenyl)thiourea.

Mass spectrum (m/z): 306 ($M^+$)

Nuclear magnetic resonance spectrum (DMSO-$d_6$, TMS internal standard) δ: 2.38 (1H, s), 7.23 (2H, d, J=8.2 Hz), 7.44 (1H, dd, J=4.9, 7.9 Hz), 7.56 (2H, d, J=8.2 Hz), 8.16 (1H, dd, J=1.8, 7.9 Hz), 8.60 (1H, dd, J=1.8, 4.9 Hz), 9.48 (1H, s), 12.12 (1H, s)

2) 2-(4-Methylanilino)-4H-pyrido[3,2-e]-1,3-thiazin-4-one 5.66 g of 1-(2-chloronicotinoyl)-3-(4-methylphenyl) thiourea and 30 mf of toluene were put in a 100 ml flask. To the flask were then connected a Dean-Stark water separator and a Dimroth condenser. The mixture was then heated under reflux for 4 hours. The reaction mixture was then allowed to cool. The resulting precipitate was collected by filtration, washed with toluene, and then dried under reduced pressure to obtain 4.69 g of 2-(4-methylanilino)-4H-pyrido [3,2-e]-1,3-thiazin-4-one.

Melting point: 208–209° C.

Elementary analysis (for $C_{14}H_{11}N_3O_3S$):

|  | C (%) | H (%) | N (%) | S (%) |
| --- | --- | --- | --- | --- |
| Calcd.: | 62.43 | 4.12 | 15.52 | 11.91 |
| Found: | 62.53 | 4.11 | 15.52 | 12.02 |

EXAMPLE 2

2-(4-Chloroanilino)-4H-pyrido[3,2-e]-1,3-thiazin-4-one 1) 1-(2-Chloronicotinoyl)-3-(4-chlorophenyl)thiourea The reaction procedure of (1) of Example 1 was followed except that 7.58 g (48.1 mmol) of 2-chloronicotinic acid, 30 ml of thionyl chloride, 3.67 g of ammonium thiocyanate and 6.14 g of 4-chloroaniline were used. As a result, 14.65 g of 1-(2-chloronicotinoyl)-3-(4-chlorophenyl)thiourea was obtained.

Mass spectrum (m/z): 326 (M⁺)

Nuclear magnetic resonance spectrum (DMSO-$d_6$, TMS internal standard) δ: 7.49 (2H, d, J=8.5 Hz), 7.57 (1H, dd, J=4.8, 7.6 Hz), 7.73 (2H, d, J=8.5 Hz), 8.12 (1H, dd, J=1.7, 7.6 Hz), 8.56 (1H, dd, J=1.7, 4.8 Hz), 12.15 (1H, s), 12.19 (1H, s)

2) 2-(4-Chloroanilino)-4H-pyrido[3,2-e]-1,3-thiazin-4-one

The reaction procedure of (2) of Example 1 was followed except that 6.19 g (19 mmol) of 1-(2-chloronicotinoyl)-3-(4-chlorophenyl)thiourea was used. As a result, 5.49 g of 2-(4-chloroanilino)-4H-pyrido[3,2-e]-1,3-thiazin-4-one was obtained.

Melting point: 278–279° C.

Elementary analysis (for $C_{13}H_8N_3OS$):

|  | C (%) | H (%) | N (%) | S (%) | Cl (%) |
|---|---|---|---|---|---|
| Calcd.: | 53.89 | 2.78 | 14.50 | 11.07 | 12.24 |
| Found: | 53.90 | 2.70 | 14.55 | 11.02 | 12.18 |

EXAMPLE 3

2-(4-Bromoanilino)-4H-pyrido[3,2-e]-1,3-thiazin-4-one 1) 1-(4-Bromophenyl)-3-(2-chloronicotinoyl)thiourea The reaction procedure of Example 1 (1) was followed except that 8.64 g (54.7 mmol) of 2-chloronicotinic acid, 40 ml of thionyl chloride, 4.16 g of ammonium thiocyanate and >9.42 g of 4-bromoaniline were used. As a result, 19 g of 1-(2-chloronicotinoyl)-3-(4-bromophenyl)thiourea was obtained.

Mass spectrum (m/z): 371 (M⁺)

Nuclear magnetic resonance spectrum (DMSO-$d_6$, TMS internal standard) δ: 7.57 (1H, dd, J=4.9, 8.0 Hz), 7.62 (2H, dd, J=2.5, 6.7 Hz), 7.67 (2H, d, J=8.5 Hz), 8.11 (1H, dd, J=1.8, 7.3 Hz), 8.56 (1H, dd, J=1.8, 4.9 Hz), 12.14 (1H, s), 12.18 (1H, s)

2) 2-(4-Bromoanilino)-4H-pyrido[3,2-e]-1,3-thiazin-4-one

The reaction procedure of Example 1 (2) was followed except that 7.54 g (20 mmol) of 1-(2-chloronicotinoyl)-3-(4-bromophenyl)thiourea was used. As a result, 6.58 g of 2-(4-bromoanilino)-4H-pyrido[3,2-e]-1,3-thiazin-4-one was obtained.

Melting point: 274.5–275° C.

Elementary analysis (for $C_{13}H_8N_3OSBr$):

|  | C (%) | H (%) | N (%) | S (%) | Br (%) |
|---|---|---|---|---|---|
| Calcd.: | 46.73 | 2.41 | 12.58 | 9.59 | 23.91 |
| Found: | 46.58 | 2.34 | 12.58 | 9.56 | 23.60 |

EXAMPLE 4

2-(4-Iodoanilino)-4H-pyrido[3,2-e]-1,3-thiazin-4-one 1) 1-(2-Chloronicotinoyl)-3-(4-iodophenyl)thiourea The reaction procedure of Example 1 (1) was followed except that 8.34 g (52.9 mmol) of 2-chloronicotinic acid, 35 ml of thionyl chloride, 4.10 g of ammonium thiocyanate and 11.59 g of 4-iodoaniline were used. As a result, 20.69 g of 1-(2-chloronicotinoyl)-3-(4-iodophenyl)thiourea was obtained.

Mass spectrum (m/z): 417 (M⁺)

Nuclear magnetic resonance spectrum (DMSO-$d_6$, TMS internal standard) δ: 7.53 (2H, d, J=8.5 Hz), 7.56 (1H, dd, J=4.9, 8.0 Hz), 7.77 (2H, d, J=8.5 Hz), 8.12 (1H, dd, J=1.8, 8.0 Hz), 8.56 (1H, dd, J=1.8, 4.9 Hz)

2) 2-(4-Iodoanilino)-4H-pyrido[3,2-e]-1,3-thiazin-4-one

The reaction procedure of Example 1 (2) was followed except that 10.42 g (24.9 mmol) of 1-(2-chloronicotinoyl)-3-(4-iodophenyl)thiourea was used. As a result, 8.29 g of 2-(4-iodoanilino)-4H-pyrido[3,2-e]-1,3-thiazin-4-one was obtained.

Melting point: 263–264° C.

Elementary analysis (for $C_{13}H_8N_3OSI$):

|  | C (%) | H (%) | N (%) | S (%) | I (%) |
|---|---|---|---|---|---|
| Calcd.: | 40.96 | 2.12 | 11.02 | 8.41 | 33.29 |
| Found: | 40.90 | 2.06 | 10.93 | 8.42 | 33.55 |

EXAMPLE 5

2-Anilino-4H-pyrido[3,2-e]-1,3-thiazin-4-one 1) 1-(2-Chloronicotinoyl)-3-phenylthiourea The reaction procedure of Example 1 (1) was followed except that 5.00 g of chloronicotinic acid, 25 ml of thionyl chloride, 2.42 g of ammonium thiocyanate and 2.96 g of aniline were used. As a result, 8.13 g of 1-(2-chloronicotinoyl)-3-phenylthiourea was obtained.

Mass spectrum (m/z): 292 (M⁺)

Nuclear magnetic resonance spectrum (CDCl₃, TMS internal standard) δ: 7.20–7.83 (m, 6H), 8.16 (1H, dd, J=2.0, 7.7 Hz), 8.60 (1H, dd, J=2.0, 4.6 Hz), 9.4–9.8 (1H, br), 12.0–12.5 (1H, br)

2) 2-Anilino-4H-pyrido[3,2-e]-1,3-thiazin-4-one

The reaction procedure of Example 1 (2) was followed except that 1.50 g of 1-(2-chloronicotinoyl)-3-phenylthiourea in the form of crude product was used. As a result, 1.05 g of 2-anilino-4H-pyrido[3,2-e]-1,3-thiazin-4-one was obtained. Nuclear magnetic resonance spectrum (DMSO-$d_6$, TMS internal standard) δ: 7.00–7.85 (6H, m), 8.48 (1H, dd, J=8.0, 1.8 Hz), 8.62–8.90 (1H, m)

Mass spectrum (m/z): 256 (M⁺+1)

EXAMPLE 6

2-(4-Nitroanilino)-4H-pyrido[3,2-e]thiazin-4-one

A mixture of 8.74 g (55.5 mmol) of 2-chloronicotinic acid, 35 ml of thionyl chloride and two droplets of DMF was heated under reflux in a 200 ml flask for 2 hours. The resulting reaction mixture was allowed to cool, and then concentrated under reduced pressure. The resulting residue was then dissolved in 30 ml of acetone. A mixture of 4.22 g of ammonium thiocyanate and 60 ml of acetone was stirred in another 200 ml flask. To the flask was then connected a dropping funnel which contained the aforementioned acetone solution of chloronicotinoyl chloride. The acetone solution was then added dropwise to the ammonium thiocyanate solution with stirring, followed by further stirring for 15 minutes.

The insoluble matters which had separated out in the reaction mixture were removed by filtration. The filtrate was then put in a 300 ml flask. To the flask was then connected a dropping funnel which contained a solution of 7.66 g of p-nitroaniline in 35 ml of acetone. The aniline solution was then added dropwise to the filtrate with stirring in 5 minutes, followed by further stirring for 15 minutes. The resulting reaction mixture was poured into ice-water in an amount of 20 or more times that of the reaction mixture. The resulting precipitate was collected by filtration, washed with water, and then dried under reduced pressure.

The reaction product thus obtained and 150 ml of toluene were put in a 500 ml flask. To the flask were then connected to a Dean-Stark water separator and a Dimroth condenser. The mixture was then heated under reflux for 18 hours. The reaction mixture was then allowed to cool. The resulting precipitate was collected by filtration, washed with toluene, and then dried under reduced pressure to obtain 15.02 g of 2-(4-nitroanilino)-4H-pyrido[3,2-e]-1,3-thiazin-4-one.

Nuclear magnetic resonance spectrum (DMSO-$d_6$/TFA-d, TMS internal standard) δ: 7.54–7.58 (3H, m), 8.30 (2H, d, J=9.2 Hz), 8.53 (1H, d, J=7.3 Hz), 8.74 (1H, d, J=4.9 Hz)

Elementary analysis (for $C_{13}H_8N_4O_3S$):

|  | C (%) | H (%) | N (%) | S (%) |
|---|---|---|---|---|
| Calcd.: | 52.00 | 2.69 | 18.66 | 10.68 |
| Found: | 51.87 | 2.55 | 18.77 | 10.48 |

EXAMPLE 7

2-(4-Cyanoanilino)-4H-pyrido[3,2-e]-1,3-thiazin-4-one

The reaction procedure of Example 6 was followed except that 3.60 g (30.64 mmol) of 2-chloronicotinic acid, 20 ml of thionyl chloride, 2.33 g of ammonium thiocyanate and 3.55 g of 4-cyanoaniline were used. As a result, 6.85 g of 2-(4-cyanoanilino)-4H-pyrido[3,2-e]-1,3-thiazin-4-one was obtained.

Nuclear magnetic resonance spectrum (DMSO-$d_6$, TMS internal standard, 80° C.) δ: 7.50–7.55 (3H, m), 7.82 (2H, dd, J=1.6, 6.7 Hz), 8.49 (1H, dd, J=1.6, 8.1 Hz), 8.71 (1H, dd, J=1.6, 4.9 Hz)

Elementary analysis (for $C_{14}H_8N_4OS$):

|  | C (%) | H (%) | N (%) | S (%) |
|---|---|---|---|---|
| Calcd.: | 59.99 | 2.88 | 19.99 | 11.44 |
| Found: | 59.65 | 2.88 | 19.81 | 11.23 |

EXAMPLE 8

2-(4-Methoxyanilino)-4H-pyrido[3,2-e]-1,3-thiazin-4-one

The reaction procedure of Example 6 was followed except that 5.00 g of chloronicotinic acid, 25 ml of thionyl chloride, 2.42 g of ammonium thiocyanate and 3.91 g of p-anisidine were used. As a result, 7.31 g of 2-(4-methoxyanilino)-4H-pyrido[3,2-e]-1,3-thiazin-4-one was obtained.

Melting point: 250–251° C.

Elementary analysis (for $C_{14}H_{11}N_3O_2S$):

|  | C (%) | H (%) | N (%) | S (%) |
|---|---|---|---|---|
| Calcd.: | 58.93 | 3.89 | 14.73 | 11.24 |
| Found: | 58.93 | 3.93 | 14.71 | 11.11 |

EXAMPLE 9

2-(4-Trifluoromethylanilino)-4H-pyrido[3,2-e]-1,3-thiazin-4-one

The reaction procedure of Example 6 was followed except that 5.00 g of chloronicotinic acid, 25 ml of thionyl chloride, 2.42 g of ammonium thiocyanate and 5.11 g of 4-aminobenzotrifluoride were used. As a result, 8.16 g of 2-(4-trifluoromethylanilino)-4H-pyrido[3,2-e]-1,3-thiazin-4-one was obtained.

Melting point: 280–283° C.

Elementary analysis (for $C_{14}H_8N_3OSF_3$):

|  | C (%) | H (%) | N (%) | S (%) | F (%) |
|---|---|---|---|---|---|
| Calcd.: | 52.01 | 2.49 | 13.00 | 9.92 | 17.63 |
| Found: | 51.95 | 2.54 | 13.02 | 9.98 | 18.18 |

EXAMPLE 10

Ethyl 4-[(4-oxo-4H-pyrido[3,2-e]-1,3-thiazin-2-yl)amino]benzoate

The reaction procedure of Example 6 was followed except that 5.00 g of chloronicotinic acid, 25 ml of thionyl chloride, 2.42 g of ammonium thiocyanate and 5.24 g of ethyl 4-aminobenzoate were used. As a result, 8.88 g of ethyl 4-[(4-oxo-4H-pyrido[3,2-e]-1,3-thiazin-2-yl)amino]benzoate obtained.

Melting point: 230–233° C.

Elementary analysis (for $C_{16}H_{13}N_3O_3S$):

|  | C (%) | H (%) | N (%) | S (%) |
|---|---|---|---|---|
| Calcd.: | 58.70 | 4.00 | 12.84 | 9.80 |
| Found: | 58.37 | 4.01 | 12.92 | 9.83 |

EXAMPLE 11

2,3-Dihydro-2-[(4-methylphenyl)imino]-3-propyl-4H-pyrido[3,2-e]-1,3-thiazin-4-one and 2-[N-(4-methylphenyl)-N-propylamino]-4H-pyrido[3,2-e]-1,3-thiazin-4-one To a mixture of 900 mg (3.34 mmol) of 2-(4-methylanilino)-4H-pyrido[3,2-e]-1,3-thiazin-4-one and 15 ml of DMF was added 27 mg of lithium hydride in a stream of argon, and it was stirred for 30 minutes at room temperature. To the mixture was then added 568 mg of n-propyl iodide. The mixture was then stirred for 2 hours. After the termination of the reaction, the mixture was concentrated under reduced pressure. To the resulting residue was added water and ethyl acetate, and extracted. The resulting organic phase was separated, washed with water and saturated brine, dried over sodium sulfate, and then concentrated under reduced pressure. The resulting residue was then purified through silica gel column chromatography (eluant: chloroform) to obtain 584 mg of 2,3-dihydro-2-[(4-methylphenyl)imino)-3-propyl-4H-pyrido[3,2-e]-1,3-thiazin-4-one (recrystallized from a mixture of ether and hexane) as a low polarity substance and 179 mg of 2-[N-(4-methylphenyl)-N-propylamino]-4H-pyrido[3,2-e]-1,3-thiazin-4-one (recrystallized from ether) as a high polarity substance.

1) 2,3-Dihydro-2-[(4-methylphenyl)imino]-3-propyl-4H-pyrido[3,2-e]-1,3-thiazin-4-one
  Melting point: 104–104.5° C.
  Elementary analysis (for $C_{17}H_{17}N_3OS$):

|  | C (%) | H (%) | N (%) | S (%) |
|---|---|---|---|---|
| Calcd.: | 65.57 | 5.50 | 13.49 | 10.30 |
| Found: | 65.53 | 5.50 | 13.45 | 10.24 |

2) 2-[N-(4-Methylphenyl)-N-propylamino]-4H-pyrido[3,2-e]-1,3-thiazin-4-one
  Mass spectrum (m/z): 312 (Ma$^+$1)
  Nuclear magnetic resonance spectrum (CDCl$_3$, TMS internal standard) δ: 0.97 (3H, t, J=7.3 Hz), 1.69 (2H, q, J=7.9, 7.3 Hz), 2.45 (3H, s), 4.09 (2H, q, J=7.9 Hz), 7.19 (2H, d, J=7.9 Hz), 7.33 (2H, d, J=7.9 Hz), 7.44 (1H, dd, J=4.5, 7.9 Hz), 8.54 (1H, dd, J=1.8, 4.5 Hz), 8.65 (1H, dd, J=1.8, 7.9 Hz)

EXAMPLE 12

2,3-Dihydro-2-[(4-methylphenyl)imino]-3-(2-isopropyl)-4H-pyrido[3,2-e]-1,3-thiazin-4-one and 2-(N-(4-methylphenyl)-N-(2-isopropyl)amino]-4H-pyrido[3,2-e]-1,3-thiazin-4-one The reaction procedure of Example 11 was followed except that 900 mg (3.34 mmol) of 2-(4-methylanilino)-4H-pyrido[3,2-e]-1,3-thiazin-4-one, 27 mg of lithium hydride and 568 mg of isopropyl iodide were used. The resulting residue was then purified through silica gel column chromatography (eluant: chloroform) to obtain 272 mg of 2,3-dihydro-2-[(4-methylphenyl)imino]-3-(2-isopropyl)-4H-pyrido[3,2-e]-1,3-thiazin-4-one (26%, recrystallized from a mixture of ether and hexane) as a low polarity substance and 248 mg of 2-[N-(4-methylphenyl)-N-(2-isopropyl)amino]-4H-pyrido[3,2-e]-1,3-thiazin-4-one (24%, recrystallized from ether) as a high polarity substance.
1) 2,3-Dihydro-2-[(4-methylphenyl)imino]-3-(2-isopropyl)-4H-pyrido[3,2-e]-1,3-thiazin-4-one
  Melting point: 132–133° C.
  Elementary analysis (for $C_{17}H_{17}N_3OS$):

|  | C (%) | H (%) | N (%) | S (%) |
|---|---|---|---|---|
| Calcd.: | 65.57 | 5.50 | 13.49 | 10.30 |
| Found: | 65.53 | 5.55 | 13.36 | 10.30 |

2) 2-[N-(4-Methylphenyl)-N-(2-isopropyl)amino]-4H-pyrido[3,2-e]-1,3-thiazin-4-one
  Melting point: 179–180° C.
  Elementary analysis (for $C_{17}H_{17}N_3OS$):

|  | C (%) | H (%) | N (%) | S (%) |
|---|---|---|---|---|
| Calcd.: | 65.57 | 5.50 | 13.49 | 10.30 |
| Found: | 65.18 | 5.42 | 13.44 | 10.12 |

EXAMPLE 13

3-Butyl-2,3-dihydro-2-[(4-methylphenyl)imino]-4H-pyrido[3,2-e]-1,3-thiazin-4-one and 2-[N-butyl-N-(4-methylphenyl)amino]-4H-pyrido[3,2-e]-1,3-thiazin-4-one The reaction procedure of Example 11 was followed except that 909 mg (3.38 mmol) of 2-(4-methylanilino)-4H-pyrido[3,2-e]-1,3-thiazin-4-one, 27 mg of lithium hydride and 621 mg of butyl iodide were used. The resulting residue was then purified through silica gel column chromatography (eluant: chloroform) to obtain 571 mg of 3-butyl-2,3-dihydro-2-[(4-methylphenyl)imino]-4H-pyrido[3,2-e]-1,3-thiazin-4-one (52%, recrystallized from a mixture of ether and hexane) as a low polarity substance and 157 mg of 2-[N-butyl-N-(4-methylphenyl)amino]-4H-pyrido[3,2-e]-1,3-thiazin-4-one (recrystallized from ether) as a high polarity substance.
1) 3-Butyl-2,3-dihydro-2-[(4-methylphenyl)imino]-4H-pyrido[3,2-e]-1,3-thiazin-4-one
  Melting point: 67.5–68.5° C.
  Elementary analysis (for $C_{18}H_{19}N_3OS$):

|  | C (%) | H (%) | N (%) | S (%) |
|---|---|---|---|---|
| Calcd.: | 66.43 | 5.58 | 12.91 | 9.85 |
| Found: | 66.39 | 5.83 | 12.85 | 9.88 |

2) 2-[N-Butyl-N-(methylphenyl)amino]-4H-pyrido[3,2-e]-1,3-thiazin-4-one
  Melting point: 128–129° C.
  Elementary analysis (for $C_{18}H_{19}N_3OS$):

|  | C (%) | H (%) | N (%) | S (%) |
|---|---|---|---|---|
| Calcd.: | 66.48 | 5.58 | 12.91 | 9.65 |
| Found: | 66.49 | 5.90 | 12.88 | 9.82 |

EXAMPLE 14

3-Allyl-2,3-dihydro-2-[(4-methylphenyl)imino]-4H-pyrido[3,2-e]-1,3-thiazin-4-one and 2-[N-allyl-N-(4-methylphenyl)amino]-4H-pyrido[3,2-e]-1,3-thiazin-4-one The reaction procedure of Example 11 was followed except that 900 mg (3.34 mmol) of 2-(4-methylanilino)-4H-pyrido[3,2-e]-1,3-thiazin-4-one, 27 mg of lithium hydride and 404 mg of allyl bromide were used. The resulting residue was then purified through silica gel column chromatography (eluant: chloroform) to obtain 539 mg of 3-allyl-2,3-dihydro-2-[(4-methylphenyl)imino]-4H-pyrido[3,2-e]-1,3-thiazin-4-one (recrystallized from a mixture of ether and hexane) as a low polarity substance and 248 mg of 2-[N-allyl-N-(4-methylphenyl)amino]-4H-pyrido[3,2-e]-1,3-thiazin-4-one (recrystallized from ether) as a high polarity substance.
1) 3-Allyl-2,3-dihydro-2-[(4-methylphenyl)imino]-4H-pyrido[3,2-e]-1,3-thiazin-4-one
  Melting point: 102–103° C.
  Elementary analysis (for $C_{17}H_{15}N_3OS$):

|  | C (%) | H (%) | N (%) | S (%) |
|---|---|---|---|---|
| Calcd.: | 66.00 | 4.89 | 13.58 | 10.36 |
| Found: | 66.05 | 4.80 | 13.61 | 10.39 |

2) 2-[N-Allyl-N-(4-methylphenyl)amino]-4H-pyrido[3,2-e]-1,3-thiazin-4-one
  Mass spectrum (m/z): 310 (M$^+$+1)
  Nuclear magnetic resonance spectrum (CDCl$_3$, TMS internal standard) δ: 2.44 (3H, s), 4.71 (2H, d, J=6.7 Hz), 5.15 (1H, d, J=17 Hz), 5.19 (1H, d, J=10 Hz), 5.93–6.02 (1H, m), 7.19 (2H, d, J=8.6 Hz), 7.31 (2H, d, J=8.6 Hz), 7.35 (1H, dd, J=4.9, 7.9 Hz), 8.55 (1H, dd, J=1.8, 4.9 Hz), 8.65 (1H, dd, J=1.8, 7.93 Hz)

EXAMPLE 15

3-Benzyl-2,3-dihydro-2-[(4-methylphenyl)imino]-4H-pyrido[3,2-e]-1,3-thiazin-4-one and 2-[N-benzyl-N-(4-methylphenyl)amino]-4H-pyrido[3,2-e]-1,3-thiazin-4-one The reaction procedure of Example 11 was followed except that 900 mg (3.34 mmol) of 2-(4-methylanilino)-4H-pyrido[3,2-e]-1,3-thiazin-4-one, 27 mg of lithium hydride and 572 mg of benzyl bromide were used. The resulting residue was then purified through silica gel column chromatography (eluant: chloroform) to obtain 631 mg of 3-benzyl-2,3-dihydro-2-[(4-methylphenyl)imino]-4H-pyrido[3,2-e]-1,3-thiazin-4-one (52%, recrystallized from a mixture of ether and hexane) as a low polarity substance and 238 mg of 2-[N-benzyl-N-(4-methylphenyl)amino]-4H-pyrido[3,2-e]-1,3-thiazin-4-one (recrystallized from ether) as a high polarity substance.

1) 3-Benzyl-2,3-dihydro-2-[(4-methylphenyl)imino]-4H-pyrido[3,2-e]-1,3-thiazin-4-one Melting point: 125–126° C.

Elementary analysis (for $C_{21}H_{17}N_3OS$):

|  | C (%) | H (%) | N (%) | S (%) |
| --- | --- | --- | --- | --- |
| Calcd.: | 70.17 | 4.77 | 11.69 | 8.92 |
| Found: | 70.22 | 4.74 | 11.65 | 8.83 |

2) 2-(N-Benzyl-N-4-(methylphenyl)amino]-4H-pyrido[3,2-e]-1,3-thiazin-4-one

Melting point: 154–155° C.

Elementary analysis (for $C_{21}H_{17}N_3OS$):

|  | C (%) | H (%) | N (%) | S (%) |
| --- | --- | --- | --- | --- |
| Calcd.: | 70.17 | 4.77 | 11.69 | 8.92 |
| Found: | 70.32 | 4.79 | 11.70 | 8.86 |

EXAMPLE 16

2-[(4-Bromophenyl)imino]-2,3-dihydro-3-methyl-4H-pyrido[3,2-e]-1,3-thiazin-4-one and 2-[N-(4-bromophenyl)-N-methylamino]-4H-pyrido[3,2-e]-1,3-thiazin-4-one The reaction procedure of Example 11 was followed except that 900 mg (2.69 mmol) of 2-(4-bromoanilino)-4H-pyrido[3,2-e]-1,3-thiazin-4-one, 24 mg of lithium hydride and =420 mg of methyl iodide were used. The resulting residue was then purified through silica gel column chromatography (eluant: chloroform) to obtain 803 mg of 2-[(4-bromophenyl)imino]-2,3-dihydro-3-methyl-4H-pyrido[3,2-e]-1,3-thiazin-4-one (86%, recrystallized from a mixture of ether and hexane) as a low polarity substance and 107 mg of 2-[N-(4-bromophenyl)-N-methylamino]-4H-pyrido[3,2-e]-1,3-thiazin-4-one (recrystallized from ether) as a high polarity substance.

1) 2-[(4-Bromophenyl)imino]-2,3-dihydro-3-methyl-4H-pyrido[3,2-e]-1,3-thiazin-4-one Melting point: 148–149° C.

Elementary analysis (for $C_{14}H_{10}N_3OSBr$):

|  | C (%) | H (%) | N (%) | S (%) | Br (%) |
| --- | --- | --- | --- | --- | --- |
| Calcd.: | 48.29 | 2.89 | 12.07 | 9.21 | 22.95 |
| Found: | 47.95 | 2.78 | 12.00 | 9.31 | 22.57 |

2) 2-[N-(4-Bromophenyl)-N-methylamino]-4H-pyrido[3,2-e]-1,3-thiazin-4-one

Mass spectrum (m/z): 348 (M$^+$+1)

Nuclear magnetic resonance spectrum (CDCl$_3$, TMS internal standard) δ: 3.70 (3H, s), 6.79 (2H, d, J=8.6 Hz), 7.28 (1H, dd, J=4.9, 7.9 Hz), 7.50 (2H, d, J=8.6 Hz), 8.55 (1H, d, J=7.9 Hz), 8.59 (1H, d, J=4.9 Hz)

3) Another method for synthesis of 2-[N-(4-bromophenyl)-N-methylamino]-4H-pyrido[3,2-e]-1,3-thiazin-4-one A mixture of 1.618 g (103 mmol) of 2-chloronicotinic acid, 15 ml of thionyl chloride and two droplets of DMF was heated under reflux in a 100 ml flask for 2 hours. The resulting reaction mixture was allowed to cool, and then concentrated under reduced pressure. The resulting residue was then dissolved in 10 ml of acetone. 798 mg of ammonium thiocyanate and 15 ml of acetone were stirred in a 50 ml flask. To the flask was then connected a dropping funnel which contained the aforementioned acetone solution of 2-chloronicotinoyl chloride. The acetone solution was then added dropwise to the ammonium thiocyanate solution with stirring in 5 minutes. The mixture was then further stirred in a 40° C. oil bath for 5 minutes. After the termination of the reaction, the resulting insoluble matters were removed by filtration. The filtrate was then put in a 100 ml flask. To the flask was then connected a dropping funnel which contained 1.808 g of 4-bromo-N-methylaniline and 10 ml of acetone. The mixture was then added dropwise to the filtrate with stirring in 5 minutes. The reaction mixture was then further stirred for 16 hours. The resulting reaction mixture was poured into 800 ml of ice-water. The resulting precipitate was collected by filtration, washed with water, and then dried under reduced pressure. The resulting crude product was then recrystallized from ethanol to obtain 2.44 g of 2-[N-(4-bromophenyl)-N-methylamino]-4H-pyrido[3,2-e]-1,3-thiazin-4-one.

Melting point: 220.8–221.8° C.

Elementary analysis (for $C_{14}H_{10}N_3OSBr$):

|  | C (%) | H (%) | N (%) | S (%) | Br (%) |
| --- | --- | --- | --- | --- | --- |
| Calcd.: | 48.29 | 2.89 | 12.07 | 9.21 | 22.95 |
| Found: | 48.22 | 2.87 | 12.05 | 9.27 | 23.24 |

EXAMPLE 17

2-[(4-Bromophenyl)imino]-2,3-dihydro-3-propyl-4H-pyrido[3,2-e]-1,3-thiazin-4-one and 2-[N-(4-bromophenyl)-N-propylamino]-4H-pyrido[3,2-e]-1,3-thiazin-4-one The reaction procedure of Example 11 was followed except that 900 mg (2.69 mmol) of 2-(4-bromoanilino)-4H-pyrido[3,2-e]-1,3-thiazin-4-one, 24 mg of lithium hydride and 503 mg of propyl iodide were used. The resulting residue was then purified through silica gel column chromatography (eluant: chloroform) to obtain 811 mg of 2-[(4- bromophenyl)imino]-2,3-dihydro-3-propyl-4H-pyrido[3,2-e]-1,3-thiazin-4-one (recrystallized from a mixture of ether and hexane) as a low polarity substance and 103 mg of 2-[N-(4-bromophenyl)-N-propylamino]-4H-pyrido[3,2-e]-1,3-thiazin-4-one (recrystallized from ether) as a high polarity substance.

1) 2-[(4-Bromophenyl)imino]-2,3-dihydro-3-propyl-4H-pyrido[3,2-e]-1,3-thiazin-4-one Melting point: 89–90° C.

Elementary analysis (for $C_{16}H_{14}N_3OSBr$):

|  | C (%) | H (%) | N (%) | S (%) | Br (%) |
|---|---|---|---|---|---|
| Calcd.: | 51.07 | 3.75 | 11.17 | 8.25 | 21.24 |
| Found: | 51.05 | 3.77 | 11.19 | 8.56 | 21.15 |

2) 2-[N-(4-Bromophenyl)-N-propylamino]-4H-pyrido[3,2-e]-1,3-thiazin-4-one

Mass spectrum (m/z): 376 (M$^+$)

Nuclear magnetic resonance spectrum (CDCl$_3$, TMS internal standard) δ: 0.96 (3H, t, J=7.3 Hz), 1.69 (2H, dt, J=7.3 Hz, 7.9 Hz), 4.08 (2H, t, J=7.9 Hz), 7.21 (2H, d, J=8.6 Hz), 7.37 (1H, dd, J=4.9, 7.9 Hz), 7.68 (2H, d, J=8.6 Hz), 8.57 (1H, dd, J=1.8, 4.9 Hz), 8.65 (1H, dd, J=1.8, 7.9 Hz)

EXAMPLE 18

3-Benzyl-2-[(4-bromophenyl)imino]-2,3-dihydro-4H-pyrido[3,2-e]-1,3-thiazin-4-one and 2-[N-benzyl-N-(4-bromophenyl)amino]-4H-pyrido[3,2-e]-1,3-thiazin-4-one The reaction procedure of Example 11 was followed except that 900 mg (2.69 mmol) of 2-(4-bromoanilino)-4H-pyrido[3,2-e]-1,3-thiazin-4-one, 24 mg of lithium hydride and 507 mg of benzyl bromide were used. The resulting residue was then purified through silica gel column chromatography (eluant: chloroform) to obtain 746 mg of 3-benzyl-2-[(4-bromophenyl)imino]-2,3-dihydro-4H-pyrido[3,2-e]-1,3-thiazin-4-one (recrystallized from a mixture of ether and hexane) as a low polarity substance and 163 mg of 2-[N-benzyl-N-(4-bromophenyl)amino]-4H-pyrido[3,2-e]-1,3-thiazin-4-one (recrystallized from a mixture of ether and ethanol) as a high polarity substance.

1) 3-Benzyl-2-[(4-bromophenyl)imino]-2,3-dihydro-4H-pyrido[3,2-e]-1,3-thiazin-4-one Melting point: 147.5–148.5° C.

Elementary analysis (for $C_{20}H_{14}N_3OSBr$):

|  | C (%) | H (%) | N (%) | S (%) | Br (%) |
|---|---|---|---|---|---|
| Calcd.: | 56.61 | 3.33 | 9.90 | 7.56 | 18.83 |
| Found: | 56.22 | 3.17 | 9.79 | 7.53 | 19.04 |

2) 2-[N-Benzyl-N-(4-bromophenyl)amino]-4H-pyrido[3,2-e]-1,3-thiazin-4-one

Mass spectrum (m/z): 423 (M$^+$)

Nuclear magnetic resonance spectrum (CDCl$_3$, TMS internal standard) δ: 5.33 (2H, s), 6.97 (2H, d, J=8.6 Hz), 7.26–7.28 (5H, bs), 7.35–40 (1H, m), 7.57 (2H, d, J=8.6 Hz), 8.58 (1H, dd, J=1.83, 4.88 Hz), 8.69 (1H, dd, J=1.83, 7.93 Hz)

EXAMPLE 19

2-[(4-Chlorophenyl)imino]-2,3-dihydro-3-ethyl-4H-pyrido[3,2-e]-1,3-thiazin-4-one and 2-[N-(4-chlorophenyl)-N-ethylamino]-4H-pyrido[3,2-e]-1,3-thiazin-4-one The reaction procedure of Example 11 was followed except that 900 mg (3.11 mmol) of 2-(4-chloroanilino)-4H-pyrido[3,2-e]-1,3-thiazin-4-one, 25 mg of lithium hydride and 584 mg of ethyl iodide were used. The resulting residue was then purified through silica gel column chromatography (eluant: chloroform) to obtain 577 mg of 2-[(4-chlorophenyl)imino]-2,3-dihydro-3-ethyl-4H-pyrido[3,2-e]-1,3-thiazin-4-one (58%, recrystallized from a mixture of ether and hexane) as a low polarity substance and 61 mg of 2-[N-(4-chlorophenyl)-N-ethylamino]-4H-pyrido[3,2-e]-1,3-thiazin-4-one (6%, recrystallized from ether) as a high polarity substance.

1) 2-[(4-Chlorophenyl)imino]-2,3-dihydro-3-ethyl-4H-pyrido[3,2-e]-1,3-thiazin-4-one Mass spectrum (m/z): 318 (M$^+$)

Nuclear magnetic resonance spectrum (CDCl$_3$, TMS internal standard) δ: 1.38 (3H, t, J=7.3 Hz), 4.43 (2H, q, J=7.3 Hz), 6.84 (2H, d, J=8.5 Hz), 7.27 (1H, dd, J=4.9, 7.9 Hz), 7.35 (2H, d, J=7.63 Hz), 8.53 (1H, dd, J=1.8, 7.9 Hz), 8.57 (1H, dd, J=1.8, 4.9 Hz)

2) 2-[N-(4-Chlorophenyl)-N-ethylamino]-4H-pyrido[3,2-e]-1,3-thiazin-4-one

Melting point: 151–152° C.

Elementary analysis (for $C_{16}H_{12}N_3OSCl$):

|  | C (%) | H (%) | N (%) | S (%) | Cl (%) |
|---|---|---|---|---|---|
| Calcd.: | 56.69 | 3.81 | 13.22 | 10.09 | 11.16 |
| Found: | 56.38 | 3.79 | 13.23 | 9.88 | 11.39 |

EXAMPLE 20

2-[(4-Chlorophenyl)imino]-2,3-dihydro-3-propyl-4H-pyrido[3,2-e]-1,3-thiazin-4-one and 2-[N-(4-chlorophenyl)-N-propylamino]-4H-pyrido[3,2-e]-1,3-thiazin-4-one The reaction procedure of Example 11 was followed except that 939 mg (3.24 mmol) of 2-(4-chloroanilino)-4H-pyrido[3,2-e]-1,3-thiazin-4-one, 26 mg of lithium hydride and 551 mg of propyl iodide were used. The resulting residue was then purified through silica gel column chromatography (eluant: chloroform) to obtain 669 mg of 2-[(4-chlorophenyl)imino]-2,3-dihydro-3-propyl-4H-pyrido[3,2-e]-1,3-thiazin-4-one (62%, recrystallized from a mixture of ether and hexane) as a low polarity substance and 112 mg of 2-[N-(4-chlorophenyl)-N-propylamino]-4H-pyrido[3,2-e]-1,3-thiazin-4-one (10%, recrystallized from ether) as a high polarity substance.

1) 2-[(4-Chlorophenyl)imino]-2,3-dihydro-3-propyl-4H-pyrido[3,2-e]-1,3-thiazin-4-one Melting point: 94–95° C.

Elementary analysis (for $C_{16}H_{14}N_3OSCl$):

|  | C (%) | H (%) | N (%) | S (%) | Cl (%) |
|---|---|---|---|---|---|
| Calcd.: | 57.91 | 4.25 | 12.66 | 9.66 | 10.68 |
| Found: | 57.91 | 4.14 | 12.69 | 9.66 | 10.50 |

2) 2-[N-(4-Chlorophenyl)-N-propylamino]-4H-pyrido[3,2-e]-1,3-thiazin-4-one

Mass spectrum (m/z): 330 (M$^+$–1)

Nuclear magnetic resonance spectrum (CDCl$_3$, TMS internal standard) δ: 0.96 (3H, t, J=7.6 Hz), 1.65–1.72 (2H, m), 4.08 (2H, t, J=7.6 Hz), 7.28 (2H, d, J=7.56 Hz), 7.37 (1H, dd, J=5.0, 7.9 Hz), 7.52 (2H, d, J=7.6 Hz), 8.56 (1H, dd, J=1.8, 4.9 Hz), 8.65 (1H, dd, J=1.8, 7.9 Hz)

EXAMPLE 21

3-Benzyl-2-[(4-chlorophenyl)imino]-2,3-dihydro-4H-pyrido[3,2-e]-1,3-thiazin-4-one and 2-[N-benzyl-N-(4-chlorophenyl)amino]-4H-pyrido[3,2-e]-1,3-thiazin-4-one The reaction procedure of Example 11 was followed except that 900 mg (2.69 mmol) of 2-(4-chloroanilino)-4H-pyrido[3,2-e]-1,3-thiazin-4-one, 24 mg of lithium hydride and 507 mg of benzyl bromide were used. The resulting residue was then purified through silica gel column chromatography (eluant: chloroform) to obtain 746 mg of 3-benzyl-2-[(4-chlorophenyl)imino]-2,3-dihydro-4H-pyrido[3,2-e]-1,3-thiazin-4-one (65%, recrystallized from a mixture of ether and hexane) as a low polarity substance and 163 mg of 2-[N-benzyl-N-(4-chlorophenyl)amino]-4H-pyrido[3,2-e]-1,3-thiazin-4-one (14%, recrystallized from ether) as a high polarity substance.

1) 3-Benzyl-2-[(4-chlorophenyl)imino]-2,3-dihydro-4H-pyrido[3,2-e]-1,3-thiazin-4-one Melting point: 135–136° C.
Elementary analysis (for $C_{20}H_{14}N_3OSCl$):

|  | C (%) | H (%) | N (%) | S (%) | Cl (%) |
|---|---|---|---|---|---|
| Calcd.: | 63.24 | 3.71 | 11.06 | 8.44 | 9.33 |
| Found: | 63.10 | 3.60 | 11.05 | 8.31 | 9.43 |

2) 2-[N-Benzyl-N-(4-chlorophenyl)amino]-4H-pyrido[3,2-e]-1,3-thiazin-4-one

Mass spectrum (m/z): 379 (M$^+$)

Nuclear magnetic resonance spectrum (CDCl$_3$, TMS internal standard) δ: 5.53 (2H, s), 7.04 (2H, d, J=8.6 Hz), 7.26–7.28 (5H, bs), 7.37–7.42 (1H, m), 7.41 (2H, d, J=8.6 Hz), 8.58 (1H, dd, J=1.8, 4.9 Hz), 8.69 (1H, dd, J=1.8, 8.9 Hz)

EXAMPLE 22

2-[(4-Iodophenyl)imino]-2,3-dihydro-3-propyl-4H-pyrido[3,2-e]-1,3-thiazin-4-one and 2-[N-(4-iodophenyl)-N-propylamino]-4H-pyrido[3,2-e]-1,3-thiazin-4-one The reaction procedure of Example 11 was followed except that 900 mg (2.36 mmol) of 2-(4-iodoanilino)-4H-pyrido(3,2-e]-1,3-thiazin-4-one, 23 mg of lithium hydride and 482 mg of propyl iodide were used. The resulting residue was then purified through silica gel column chromatography (eluant: chloroform) to obtain 653 mg of 2-[(4-iodophenyl)imino]-2,3-dihydro-3-propyl-4H-pyrido[3,2-e]-1,3-thiazin-4-one (65%, recrystallized from a mixture of ether and hexane) as a low polarity substance and 40 mg of 2-[N-(4-iodophenyl)-N-propylamino]-4H-pyrido[3,2-e]-1,3-thiazin-4-one (4%, recrystallized from ether) as a high polarity substance.

1) 2-[(4-Iodophenyl)imino]-2,3-dihydro-3-propyl-4H-pyrido[3,2-e]-1,3-thiazin-4-one Melting point: 104.5–105.5° C.
Elementary analysis (for $C_{16}H_{14}N_3OSI$):

|  | C (%) | H (%) | N (%) | S (%) | I (%) |
|---|---|---|---|---|---|
| Calcd.: | 45.40 | 3.33 | 9.93 | 7.58 | 29.98 |
| Found: | 45.17 | 3.27 | 9.75 | 7.69 | 30.06 |

2) 2-[N-(4-Iodophenyl)-N-propylamino]-4H-pyrido[3,2-e]-1,3-thiazin-4-one

Melting point: 204–205° C.
Elementary analysis (for $C_{16}H_{14}N_3OSI$):

|  | C (%) | H (%) | N (%) | S (%) | I (%) |
|---|---|---|---|---|---|
| Calcd.: | 45.40 | 3.33 | 9.93 | 7.58 | 29.98 |
| Found: | 45.28 | 3.11 | 9.81 | 7.56 | 30.14 |

EXAMPLE 23

2-[(4-Cyanophenyl)imino]-2,3-dihydro-3-propyl-4H-pyrido[3,2-e]-1,3-thiazin-4-one and 2-[N-(4-cyanophenyl)-N-propylamino]-4H-pyrido[3,2-e]-1,3-thiazin-4-one The reaction procedure of Example 11 was followed except that 900 mg (3.21 mmol) of 2-(4-cyanoanilino)-4H-pyrido[3,2-e]-1,3-thiazin-4-one, 42 mg of lithium hydride and 655 mg of propyl iodide were used. The resulting residue was then purified through silica gel column chromatography (eluant: chloroform) to obtain 734 mg of 2-[(4-cyanophenyl)imino]-2,3-dihydro-3-propyl-4H-pyrido[3,2-e]-1,3-thiazin-4-one (71%, recrystallized from a mixture of ether and hexane) as a low polarity substance and 100 mg of 2-[N-(4-cyanophenyl)-N-propylamino]-4H-pyrido[3,2-e]-1,3-thiazin-4-one (10%, recrystallized from ether) as a high polarity substance.

1) 2-[(4-Cyanophenyl)imino]-2,3-dihydro-3-propyl-4H-pyrido[3,2-e]-1,3-thiazin-4-one Melting point: 114–115° C.
Elementary analysis (for $C_{17}H_{14}N_4OS$):

|  | C (%) | H (%) | N (%) | S (%) |
|---|---|---|---|---|
| Calcd.: | 63.34 | 4.38 | 17.38 | 9.95 |
| Found: | 63.14 | 4.29 | 17.33 | 9.87 |

2) 2-[N-(4-Cyanophenyl)-N-propylamino]-4H-pyrido[3,2-e]-1,3-thiazin-4-one

Melting point: 225.5–226.5° C.
Elementary analysis (for $C_{17}H_4N_3OS$):

|  | C (%) | H (%) | N (%) | S (%) |
|---|---|---|---|---|
| Calcd.: | 63.34 | 4.38 | 17.38 | 9.95 |
| Found: | 63.14 | 4.29 | 17.33 | 9.87 |

EXAMPLE 24

3-Benzyl-2-[(4-cyanophenyl)imino]-2,3-dihydro-4H-pyrido[3,2-e]-1,3-thiazin-4-one and 2-[N-benzyl-N-(4-cyanophenyl)amino]-4H-pyrido[3,2-e]-1,3-thiazin-4-one The reaction procedure of Example 11 was followed except that 900 mg (3.21 mmol) of 2-(4-cyanoanilino)-4H- pyrido[3,2-e]-1,3-thiazin-4-one, 28 mg of lithium hydride and 604 mg of benzyl bromide were used. The resulting residue was then purified through silica gel column chromatography (eluant: chloroform) to obtain 834 mg of 3-benzyl-2-[(4-cyanophenyl)imino]-2,3-dihydro-4H-pyrido[3,2-e]-1,3-thiazin-4-one (70%, recrystallized from a mixture of ether and hexane) as a low polarity substance and 103 mg of 2-[N-benzyl-N-(4-cyanophenyl)-N-propylamino]-4H-pyrido[3,2-e]-1,3-thiazin-4-one (10%, recrystallized from ether) as a high polarity substance.

1) 3-Benzyl-2-[(4-cyanophenyl)imino]-2,3-dihydro-4H-pyrido[3,2-e]-1,3-thiazin-4-one Melting point: 137–138° C.

Elementary analysis (for $C_{21}H_{14}N_4OS$):

|  | C (%) | H (%) | N (%) | S (%) |
|---|---|---|---|---|
| Calcd.: | 68.09 | 3.81 | 15.21 | 8.66 |
| Found: | 67.80 | 3.76 | 15.06 | 8.73 |

2) 2-[N-Benzyl-N-(4-cyanophenyl)amino]-4H-pyrido[3,2-e]-1,3-thiazin-4-one

Mass spectrum (m/z): 371 ($M^+$+1)

Nuclear magnetic resonance spectrum ($CDCl_3$, TMS internal standard) δ: 5.37 (2H, s), 7.24–7.28 (5H, m), 7.29 (2H, dd, J=3.1, 6.7 Hz), 7.42 (1H, dd, J=4.6, 7.9 Hz), 7.75 (2H, dd, J=1.8, 6.7 Hz), 8.60 (1H, dd, J=1.8, 4.3 Hz), 8.70 (1H, dd, J=1.8, 7.9 Hz)

EXAMPLE 25

2-[(4-Methoxyphenyl)imino]-3-methyl-2,3-dihydro-4H-pyrido[3,2-e]-1,3-thiazin-4-one and 2-[N-(4-methoxyphenyl)-N-methylamino]-4H-pyrido[3,2-e]-1,3-thiazin-4-one The reaction procedure of Example 11 was followed except that 428 mg of 2-(4-methoxyanilino)-4H-pyrido[3,2-e]-1,3-thiazin-4-one, 14 mg of lithium hydride and 0.094 ml of methyl iodide were used. As a result, 200 mg of 2-[(4-methoxyphenyl)imino]-3-methyl-2,3-dihydro-4H-pyrido[3,2-e]-1,3-thiazin-4-one was obtained as a low polarity substance, and 35 mg of 2-[N-(4-methoxyphenyl)-N-methylamino]-4H-pyrido[3,2-e]-1,3-thiazin-4-one was obtained as a high polarity substance.

1) 2-[(4-Methoxyphenyl)imino]-3-methyl-2,3-dihydro-4H-pyrido[3,2-e]-1,3-thiazin-4-one Melting point: 155–157° C.

Elementary analysis (for $C_{15}H_{13}N_3O_2S$):

|  | C (%) | H (%) | N (%) | S (%) |
|---|---|---|---|---|
| Calcd.: | 60.18 | 4.38 | 14.04 | 10.71 |
| Found: | 60.29 | 4.28 | 14.01 | 10.70 |

2) 2-[N-(4-Methoxyphenyl)-N-methylamino]-4H-pyrido[3,2-e]-1,3-thiazin-4-one

Nuclear magnetic resonance spectrum ($CDCl_3$, TMS internal standard) δ: 3.71 (3H, s), 3.83 (3H, s), 6.85 (2H, d, J=7.9 Hz), 6.93 (2H, d, J=9.2 Hz), 7.26–7.29 (1H, m), 8.51–8.58 (2H, m)

Mass spectrum (m/z): 299 ($M^+$)

EXAMPLE 26

3-Ethyl-2-[(4-methoxyphenyl)imino]-2,3-dihydro-4H-pyrido[3,2-e]-1,3-thiazin-4-one and 2-[N-ethyl-N-(4-methoxyphenyl)amino]-4H-pyrido[3,2-e]-1,3-thiazin-4-one The reaction procedure of Example 11 was followed except that 428 mg of 2-(4-methoxyanilino)-4H-pyrido[3,2-e]-1,3-thiazin-4-one, 14 mg of lithium hydride and 0.12 ml of methyl iodide were used. As a result, 311 mg of 3-ethyl-2-[(4-methoxyphenyl)imino]-2,3-dihydro-4H-pyrido[3,2-e]-1,3-thiazin-4-one was obtained as a low polarity substance, and 40 mg of 2-[N-ethyl-N-(4-methoxyphenyl)amino]-4H-pyrido[3,2-e]-1,3-thiazin-4-one was obtained as a high polarity substance.

1) 3-Ethyl-2-[(4-methoxyphenyl)imino]-2,3-dihydro-4H-pyrido[3,2-e]-1,3-thiazin-4-one Melting point: 114–115° C.

Elementary analysis (for $C_{16}H_{15}N_3O_2S$):

|  | C (%) | H (%) | N (%) | S (%) |
|---|---|---|---|---|
| Calcd.: | 61.32 | 4.82 | 13.41 | 10.23 |
| Found: | 61.48 | 4.76 | 13.47 | 10.15 |

2) 2-[N-Ethyl-N-(4-methoxyphenyl)amino]-4H-pyrido[3,2-e]-1,3-thiazin-4-one

Melting point: 172–174° C.

Elementary analysis (for $C_{16}H1_{15}N_3O_2S$):

|  | C (%) | H (%) | N (%) | S (%) |
|---|---|---|---|---|
| Calcd.: | 61.32 | 4.82 | 13.41 | 10.23 |
| Found: | 61.29 | 4.71 | 13.40 | 10.18 |

EXAMPLE 27

2-[(4-Methoxyphenyl)imino]-3-propyl-2,3-dihydro-4H-pyrido[3,2-e]-1,3-thiazin-4-one and 2-[N-(4-methoxyphenyl)-N-propylamino]-4H-pyrido[3,2-e]-1,3-thiazin-4-one The reaction procedure of Example 11 was followed except that 428 mg of 2-(4-methoxyanilino)-4H-pyrido[3,2-e]-1,3-thiazin-4-one, 14 mg of lithium hydride and 0.15 ml of propyl iodide were used. As a result, 227 mg of 2-[(4-methoxyphenyl)imino]-3-propyl-2,3-dihydro-4H-pyrido[3,2-e]-1,3-thiazin-4-one was obtained as a low polarity substance, and 78 mg of 2-[N-(4-methoxyphenyl)-N-propylamino]-4H-pyrido[3,2-e]-1,3-thiazin-4-one was obtained as a high polarity substance.

1) 2-[(4-Methoxyphenyl)imino]-3-propyl-2,3-dihydro-4H-pyrido[3,2-e]-1,3-thiazin-4-one Melting point: 78–79° C.

Elementary analysis (for $C_{17}H_{17}N_3O_2S$):

|  | C (%) | H (%) | N (%) | S (%) |
|---|---|---|---|---|
| Calcd.: | 62.36 | 5.23 | 12.83 | 9.79 |
| Found: | 62.58 | 5.20 | 12.83 | 9.79 |

2) 2-[N-(4-Methoxyphenyl)-N-propylamino]-4H-pyrido[3,2-e]-1,3-thiazin-4-one

Melting point: 162–164° C.

Elementary analysis (for $C_{17}H_{17}N_3O_2S$):

|  | C (%) | H (%) | N (%) | S (%) |
|---|---|---|---|---|
| Calcd.: | 62.36 | 5.23 | 12.83 | 9.79 |
| Found: | 62.13 | 5.18 | 12.60 | 9.79 |

EXAMPLE 28

3-Isopropyl-2-[(4-methoxyphenyl)imino]-2,3-dihydro-4H-pyrido[3,2-e]-1,3-thiazin-4-one monohydrochloride and 2-[N-isopropyl-N-(4-methoxyphenyl)amino]-4H-pyrido[3,2-e]-1,3-thiazin-4-one The reaction procedure of Example 11 was followed except that 700 mg of 2-(4-methoxyanilino)-4H-pyrido[3,2-e]-1,3-thiazin-4-one, 22 mg of lithium hydride and 0.25 ml of isopropyl iodide were used. As a result, 30 mg of 3-isopropyl-2-[(4-methoxyphenyl)imino]-2,3-dihydro-4H-pyrido[3,2-e]-1,3-thiazin-4-one monohydrochloride was obtained as a low polarity substance, and 198 mg of 2-[N-isopropyl-N-(4-methoxyphenyl)amino]-4H-pyrido[3,2-e]-1,3-thiazin-4-one was obtained as a high polarity substance.

1) 3-Isopropyl-2-[(4-methoxyphenyl)imino]-2,3-dihydro-4H-pyrido[3,2-e]-1,3-thiazin-4-one monohydrochloride Melting point: 78–81° C.

Nuclear magnetic resonance spectrum (CDCl$_3$, TMS internal standard) δ: 1.64 (6H, d, J=6.4 Hz), 3.84 (3H, s), 5.53–5.66 (1H, m), 6.82–6.98 (4H, m), 7.38 (1H, dd, J=4.9, 7.8 Hz), 8.54–8.68 (2H, m)

2) 2-[N-Isopropyl-N-(4-methoxyphenyl)amino]-4H-pyrido[3,2-e]-1,3-thiazin-4-one

Melting point: 188–190° C.

Elementary analysis (for $C_{17}H_{17}N_3O_2S$):

|  | C (%) | H (%) | N (%) | S (%) |
|---|---|---|---|---|
| Calcd.: | 62.36 | 5.23 | 12.83 | 9.79 |
| Found: | 62.20 | 5.12 | 12.78 | 9.82 |

EXAMPLE 29

3-Butyl-2-[(4-methoxyphenyl)imino]-2,3-dihydro-4H-pyrido[3,2-e]-1,3-thiazin-4-one and 2-[N-butyl-N-(4-methoxyphenyl)amino]-4H-pyrido[3,2-e]-1,3-thiazin-4-one The reaction procedure of Example 11 was followed except that 428 mg of 2-(4-methoxyanilino)-4H-pyrido[3,2-e]-1,3-thiazin-4-one, 14 mg of lithium hydride and 0.17 ml of butyl iodide were used. As a result, 295 mg of 3-butyl-2-[(4-methoxyphenyl)imino]-2,3-dihydro-4H-pyrido[3,2-e]-1,3-thiazin-4-one was obtained as a low polarity substance, and 55 mg of 2-[N-butyl-N-(4-methoxyphenyl)amino]-4H-pyrido[3,2-e]-1,3-thiazin-4-one was obtained as a high polarity substance.

1) 3-Butyl-2-[(4-methoxyphenyl)imino]-2,3-dihydro-4H-pyrido[3,2-e]-1,3-thiazin-4-one Melting point: 79–80° C.

Elementary analysis (for $C_{18}H_{19}N_3O_2S$):

|  | C (%) | H (%) | N (%) | S (%) |
|---|---|---|---|---|
| Calcd.: | 63.32 | 5.61 | 12.31 | 9.39 |
| Found: | 63.23 | 5.57 | 12.19 | 9.32 |

2) 2-[N-Butyl-N-(4-methoxyphenyl)amino]-4H-pyrido[3,2-e]-1,3-thiazin-4-one

Nuclear magnetic resonance spectrum (CDCl$_3$, TMS internal standard) δ: 0.92 (3H, t, J=7.3 Hz), 1.34–1.43 (2H, m), 1.60–1.68 (2H, m), 3.89 (3H, s), 4.08–4.16 (2H, m), 7.03 (2H, d, J=8.6 Hz), 7.22 (2H, d, J=9.2 Hz), 7.38–7.43 (1H, m), 8.58 (1H, dd, J=4.9, 1.8 Hz), 8.68–8.75 (1H, m)

Mass spectrum (m/z): 342 (M$^+$+1)

EXAMPLE 30

3-Allyl-2-[(4-methoxyphenyl)imino]-2,3-dihydro-4H-pyrido[3,2-e]-1,3-thiazin-4-one and 2-[N-allyl-N-(4-methoxyphenyl)amino]-4H-pyrido[3,2-e]-1,3-thiazin-4-one The reaction procedure of Example 11 was followed except that 428 mg of 2-(4-methoxyanilino)-4H-pyrido[3,2-e]-1,3-thiazin-4-one, 14 mg of lithium hydride and 0.13 ml of allyl bromide were used. As a result, 213 mg of 3-allyl-2-[(4-methoxyphenyl)imino]-2,3-dihydro-4H-pyrido[3,2-e]-1,3-thiazin-4-one was obtained as a low polarity substance, and 85 mg of 2-[N-allyl-N-(4-methoxyphenyl)amino]-4H-pyrido[3,2-e]-1,3-thiazin-4-one was obtained as a high polarity substance.

1) 3-Allyl-2-[(4-methoxyphenyl)imino]-2,3-dihydro-4H-pyrido[3,2-e]-1,3-thiazin-4-one Melting point: 97–98° C.

Elementary analysis (for $C_{17}H_{15}N_3O_2S$):

|  | C (%) | H (%) | N (%) | S (%) |
|---|---|---|---|---|
| Calcd.: | 62.75 | 4.65 | 12.91 | 9.85 |
| Found: | 62.96 | 4.63 | 12.90 | 9.91 |

2) 2-[N-Allyl-N-(4-methoxyphenyl)amino]-4H-pyrido[3,2-e]-1,3-thiazin-4-one

Melting point: 152–154° C.

Elementary analysis (for $C_{17}H_{15}N_3O_2S$):

|  | C (%) | H (%) | N (%) | S (%) |
|---|---|---|---|---|
| Calcd.: | 62.75 | 4.65 | 12.91 | 9.85 |
| Found: | 62.70 | 4.56 | 12.93 | 9.84 |

EXAMPLE 31

3-Benzyl-2-[(4-methoxyphenyl)imino]-2,3-dihydro-4H-pyrido[3,2-e]-1,3-thiazin-4-one and 2-[N-benzyl-N-(4-methoxyphenyl)amino]-4H-pyrido[3,2-e]-1,3-thiazin-4-one The reaction procedure of Example 11 was followed except that 428 mg of 2-(4-methoxyanilino)-4H-pyrido[3,2- e]-1,3-thiazin-4-one, 14 mg of lithium hydride and 0.18 ml of benzyl bromide were used. As a result, 295 mg of 3-benzyl-2-[(4-methoxyphenyl)imino]-2,3-dihydro-4H-pyrido[3,2-e]-1,3-thiazin-4-one was obtained as a low polarity substance, and 174 mg of 2-[N-benzyl-N-(4-methoxyphenyl)amino]-4H-pyrido[3,2-e]-1,3-thiazin-4-one was obtained as a high polarity substance.

1) 3-Benzyl-2-[(4-methoxyphenyl)imino]-2,3-dihydro-4H-pyrido[3,2-e]-1,3-thiazin-4-one Melting point: 123–126° C.

Elementary analysis (for $C_{21}H_{17}N_3O_2S$):

|  | C (%) | H (%) | N (%) | S (%) |
|---|---|---|---|---|
| Calcd.: | 67.18 | 4.56 | 11.19 | 8.54 |
| Found: | 67.18 | 4.58 | 11.19 | 8.58 |

2) 2-[N-Benzyl-N-(4-methoxyphenyl)amino]-4H-pyrido[3,2-e]-1,3-thiazin-4-one

Melting point: 177–178° C.

Elementary analysis (for $C_{21}H_{17}N_3O_2S$):

|  | C (%) | H (%) | N (%) | S (%) |
|---|---|---|---|---|
| Calcd.: | 67.18 | 4.56 | 11.19 | 8.54 |
| Found: | 67.05 | 4.64 | 10.87 | 8.25 |

EXAMPLE 32

3-(2-Diethylaminoethyl)-2-[(4-methoxyphenyl) imino]-2,3-dihydro-4H-pyrido[3,2-e]-1,3-thiazin-4-one monohydrochloride and 2-[N-(2-diethylaminoethyl)-N-(4-methoxyphenyl)amino]-4H-pyrido[3,2-e]-1,3-thiazin-4-one The reaction procedure of Example 11 was followed except that 500 mg of 2-(4-methoxyanilino)-4H-pyrido[3,2-e]-1,3-thiazin-4-one, 32 mg of lithium hydride and 302 mg of 2-diethylaminoethylchloride hydrochloride were used. As a result, 60 mg of 3-(2-diethylaminoethyl)-2-[(4-methoxphenyl)imino]-2,3-dihydro-4H-pyrido[3,2-e]-1,3-thiazin-4-one monohydrochloride was obtained as a low polarity substance, and 60 mg of 2-[N-(2-diethylaminoethyl)-N-(4-methoxyphenyl)amino]-4H-pyrido[3,2-e]-1,3-thiazin-4-one was obtained as a high polarity substance.

1) 3-(2-Diethylaminoethyl)-2-[(4-methoxyphenyl)imino]-2,3-dihydro-4H-pyrido[3,2-e]-1,3-thiazin-4-one monohydrochloride Nuclear magnetic resonance spectrum (CDCl₃, TMS internal standard) δ: 1.54 (6H, t, J=7.3 Hz), 3.19–3.33 (4H, m), 3.44–3.53 (2H, m), 3.83 (3H, s), 4.73–4.81 (2H, m), 6.86 (2H, d, J=8.6 Hz), 6.94 (2H, d, J=9.2 Hz), 7.30 (1H, dd, J=7.9, 4.9 Hz), 8.50 (1H, d, J=7.9 Hz), 8.58–8.62 (1H, m), 12.51 (1H, bs)

Mass spectrum (m/z): 385 (M⁺+1)

2) 2-[N-(2-Diethylaminoethyl)-N-(4-methoxyphenyl) amino]-4H-pyrido[3,2-e]-1,3-thiazin-4-one Nuclear magnetic resonance spectrum (CDCl₃, TMS internal standard) δ: 0.93–1.02 (6H, m), 2.50–2.59 (4H, m), 2.78 (2H, t, J=6.7 Hz), 3.88 (3H, s), 4.16 (2H, t, J=6.7 Hz), 6.97–7.03 (2H, m), 7.28–7.37 (3H, m), 8.52–8.57 (1H, m), 8.65 (1H, dd, J=7.9, 1.8 Hz)

Mass spectrum (m/z): 384 (M)

EXAMPLE 33

3-Methyl-2-[(4-trifluoromethylphenyl)imino]-2,3-dihydro-4H-pyrido[3,2-e]-1,3-thiazin-4-one and 2-[N-methyl-N-(4-trifluoromethylphenyl)amino]-4H-pyrido[3,2-e]-1,3-thiazin- 4-one The reaction procedure of Example 11 was followed except that 646 mg of 2-(4-trifluoromethylanilino)-4H-pyrido[3,2-e]-1,3-thiazin-4-one, 18 mg of lithium hydride and 0.13 ml of methyl iodide were used. As a result, 565 mg of 3-methyl-2-[(4-trifluoromethylphenyl)imino]-2,3-dihydro-4H-pyrido[3,2-e]-1,3-thiazin-4-one was obtained as a low polarity substance, and 25 mg of 2-[N-methyl-N-(4-trifluoromethylphenyl)amino]-4H-pyrido[3,2-e]-1,3-thiazin-4-one was obtained as a high polarity substance.

1) 3-Methyl-2-[(4-trifluoromethylphenyl)imino]-2,3-dihydro-4H-pyrido[3,2-e]-1,3-thiazin-4-one Nuclear magnetic resonance spectrum (CDCl₃, TMS internal standard) δ: 3.68 (3H, s), 7.40 (1H, dd, J=7.9, 4.9 Hz), 7.52 (2H, d, J=8.6 Hz), 7.82 (2H, d, J=8.5 Hz), 8.60 (1H, dd, J=4.9, 1.8 Hz), 8.68 (1H, dd, J=7.9, 1.8 Hz)

Mass spectrum (m/z): 338 (M+1)

2) 2-[N-Methyl-N-(4-trifluoromethylphenyl)amino]-4H-pyrido[3,2-e]-1,3-thiazin-4-one Melting point: 184–188° C.

Elementary analysis (for $C_{15}H_{10}F_3N_3OS$):

|  | C (%) | H (%) | N (%) | S (%) | F (%) |
|---|---|---|---|---|---|
| Calcd.: | 53.41 | 2.99 | 12.46 | 9.51 | 16.90 |
| Found: | 53.60 | 3.06 | 12.28 | 9.29 | 16.73 |

EXAMPLE 34

Ethyl 4-[(3-benzyl-4-oxo-2,3-dihydro-4H-pyrido[3,2-e]-1,3-thiazin-2-ylidene)amino]benzoate and ethyl 4-[N-benzyl-N-(4-oxo-4H-pyrido[3,2-e]-1,3-thiazin-2-yl)amino]benzoate The reaction procedure of Example 11 was followed except that 1.31 g of ethyl 4-[(4-oxo-4H-pyrido[3,2-e]-1,3-thiazin-2-yl)amino]benzoate, 36 mg of lithium hydride and 0.48 ml of benzyl bromide were used. As a result, 1.28 g of ethyl 4-[(3-benzyl-4-oxo-2,3-dihydro-4H-pyrido[3,2-e]-1,3-thiazin-2-ylidene)amino]benzoate was obtained as a low polarity substance, and 20 mg of ethyl 4-[N-benzyl-N-(4-oxo-4H-pyrido[3,2-e]-1,3-thiazin-2-yl)amino]benzoate was obtained as a high polarity substance.

1) Ethyl 4-[(3-benzyl-4-oxo-2,3-dihydro-4H-pyrido[3,2-e]-1,3-thiazin-2-ylidene)amino]benzoate Melting point: 128–129° C.

Elementary analysis (for $C_{23}H_{19}N_3O_3S$):

|  | C (%) | H (%) | N (%) | S (%) |
|---|---|---|---|---|
| Calcd.: | 66.17 | 4.59 | 10.07 | 7.68 |
| Found: | 65.97 | 4.51 | 9.95 | 7.75 |

2) Ethyl 4-[N-benzyl-N-(4-oxo-4H-pyrido[3,2-e]-1,3-thiazin-2-yl)amino]benzoate

Nuclear magnetic resonance spectrum (CDCl₃, TMS internal standard) δ: 1.41 (3H, t, J=7.2 Hz), 4.41 (2H, q, J=7.1 Hz), 5.37 (2H, s), 7.11–7.49 (8H, m), 8.02–8.20 (2H, m), 8.53–8.77 (2H, m)

Mass spectrum (m/z): 418 (M+1)

EXAMPLE 35

2,3-Dihydro-3-methyl-2-[(4-methylphenyl)imino]-4H-pyrido[3,2-e]-1,3-thiazin-4-one The reaction procedure of Example 11 was followed except that 949 mg (3.52 mmol) of 2-(4-methylanilino)-4H-pyrido[3,2-e]-1,3-thiazin-4-one, 28 mg of lithium hydride and 500 mg of methyl iodide were used. The resulting residue was then purified through silica gel column chromatography (eluant: chloroform) to obtain 698 mg of 2,3-dihydro-3-methyl-2-[(4-methylphenyl)imino]-4H-pyrido[3,2-e]-1,3-thiazin-4-one (70%, recrystallized from a mixture of ether and hexane).

Melting point: 143.5–144.5° C.

Elementary analysis (for $C_{15}H_{13}N_3OS$):

|        | C (%)  | H (%) | N (%)  | S (%)  |
|--------|--------|-------|--------|--------|
| Calcd.: | 63.58 | 4.62  | 14.83  | 11.32  |
| Found:  | 63.59 | 4.66  | 14.89  | 11.26  |

EXAMPLE 36

2,3-Dihydro-3-ethyl-2-[(4-methylphenyl)imino]-4H-pyrido[3,2-e]-1,3-thiazin-4-one The reaction procedure of Example 11 was followed except that 900 mg (3.52 mmol) of 2-(4-methylanilino)-4H-pyrido[3,2-e]-1,3-thiazin-4-one, 28 mg of lithium hydride and 603 mg of ethyl iodide were used. The resulting residue was then purified through silica gel column chromatography (eluant: chloroform) to obtain 603 mg of 2,3-dihydro-3-ethyl-2-[(4-ethylphenyl)imino]-4H-pyrido[3,2-e]-1,3-thiazin-4-one (58%, recrystallized from a mixture of ether and hexane).

Melting point: 148–149° C.

Elementary analysis (for $C_{16}H_{15}N_3OS$):

|        | C (%)  | H (%) | N (%)  | S (%)  |
|--------|--------|-------|--------|--------|
| Calcd.: | 64.62 | 5.08  | 14.13  | 10.78  |
| Found:  | 64.75 | 5.06  | 14.14  | 10.71  |

EXAMPLE 37

2-[(4-Chlorophenyl)imino]-2,3-dihydro-3-methyl-4H-pyrido[3,2-e]-1,3-thiazin-4-one The reaction procedure of Example 11 was followed except that 900 mg (3.11 mmol) of 2-(4-chloroanilino)-4H-pyrido[3,2-e]-1,3-thiazin-4-one, 25 mg of lithium hydride and 440 mg of methyl iodide were used. The resulting residue was then purified through silica gel column chromatography (eluant: chloroform) to obtain 554 mg of 2-[(4-chlorophenyl)imino]-2,3-dihydro-3-methyl-4H-pyrido[3,2-e]-1,3-thiazin-4-one (59%, recrystallized from a mixture of ether and hexane).

Melting point: 142–143° C.

Elementary analysis (for $C_{14}H_{10}N_3OSCl$):

|        | C (%)  | H (%) | N (%)  | S (%)  | Cl (%) |
|--------|--------|-------|--------|--------|--------|
| Calcd.: | 55.36 | 3.32  | 13.83  | 10.56  | 11.67  |
| Found:  | 55.29 | 3.26  | 13.86  | 10.51  | 11.53  |

EXAMPLE 38

2-[(4-Iodophenyl)imino]-2,3-dihydro-3-methyl-4H-pyrido[3,2-e]-1,3-thiazin-4-one

The reaction procedure of Example 11 was followed except that 900 mg (2.36 mmol) of 2-(4-iodoanilino)-4H-pyrido[3,2-e]-1,3-thiazin-4-one, 23 mg of lithium hydride and 402 mg of methyl iodide were used. The resulting residue was then purified through silica gel column chromatography (eluant: chloroform) to obtain 580 mg of 2-[(4-iodophenyl)imino]-2,3-dihydro-3-methyl-4H-pyrido[3,2-e]-1,3-thiazin-4-one (62%, recrystallized from a mixture of ether and hexane).

Melting point: 144.5–145.5° C.

Elementary analysis (for $C_{14}H_{10}N_3OSI$)

|        | C (%)  | H (%) | N (%) | S (%) | I (%)  |
|--------|--------|-------|-------|-------|--------|
| Calcd.: | 45.40 | 3.33  | 9.93  | 7.58  | 29.98  |
| Found   | 45.17 | 3.27  | 9.75  | 7.69  | 30.06  |

EXAMPLE 39

2-[(4-Cyanophenyl)imino]-2,3-dihydro-3-methyl-4H-pyrido[3,2-e]-1,3-thiazin-4-one The reaction procedure of Example 11 was followed except that 900 mg (3.21 mmol) of 2-(4-cyanoanilino)-4H-pyrido[3,2-e]-1,3-thiazin-4-one, 42 mg of lithium hydride and 547 mg of methyl iodide were used. The resulting residue was then purified through silica gel column chromatography (eluant: chloroform) to obtain 762 mg of 2-[(4-cyanophenyl)imino]-2,3-dihydro-3-methyl-4H-pyrido[3,2-e]-1,3-thiazin-4-one (81%, recrystallized from a mixture of ether and hexane).

Melting point: 176–177° C.

Elementary analysis (for $C_{15}H_{10}N_4OS$):

|        | C (%)  | H (%) | N (%)  | S (%)  |
|--------|--------|-------|--------|--------|
| Calcd.: | 61.25 | 3.42  | 19.03  | 10.89  |
| Found:  | 61.14 | 3.35  | 19.33  | 10.85  |

EXAMPLE 40

2,3-Dihydro-3-methyl-2-[(4-nitrophenyl)imino]-4H-pyrido[3,2-e]-1,3-thiazin-4-one The reaction procedure of Example 11 was followed except that 901 mg (3.0 mmol) of 2-(4-nitroanilino)-4H-pyrido[3,2-e]-1,3-thiazin-4-one, 30 mg of lithium hydride and 511 mg of methyl iodide were used. The resulting residue was then purified through silica gel chromatography (eluant: chloroform) to obtain 756 mg of 2,3-dihydro-3-methyl-2-[(4-nitrophenyl)imino]-4H-pyrido[3,2-e]-1,3-thiazin-4-one (80%, recrystallized from a mixture of ether and ethanol).

Melting point: 186–187° C.

Elementary analysis (for $C_{14}H_{10}N_4O_3S$)

|  | C (%) | H (%) | N (%) | S (%) |
|---|---|---|---|---|
| Calcd.: | 53.50 | 3.21 | 17.82 | 10.20 |
| Found: | 53.60 | 3.27 | 17.72 | 10.24 |

EXAMPLE 41

2,3-Dihydro-2-[(4-nitrophenyl)imino]-3-propyl-4H-pyrido[3,2-e]-1,3-thiazin-4-one The reaction procedure of Example 11 was followed except that 901 mg (3.0 mmol) of 2-(4-nitroanilino)-4H-pyrido[3,2-e]-1,3-thiazin-4-one, 30 mg of lithium hydride and 612 mg of propyl iodide were used. The resulting residue was then purified through silica gel column chromatography (eluant: chloroform) to obtain 603 mg of 2,3-dihydro-2-[(4-nitrophenyl)imino]-3-propyl-4H-pyrido[3,2-e]-1,3-thiazin-4-one (59%, recrystallized from a mixture of ether and ethanol).

Melting point: 112–113° C. Elementary analysis (for $C_{16}H_{14}N_4O_3S$):

|  | C (%) | H (%) | N (%) | S (%) |
|---|---|---|---|---|
| Calcd.: | 56.13 | 4.12 | 16.36 | 9.37 |
| Found: | 56.15 | 4.08 | 16.36 | 9.37 |

EXAMPLE 42

3-Benzyl-2,3-dihydro-2-[(4-nitrophenyl)imino]-4H-pyrido[3,2-e]-1,3-thiazin-4-one The reaction procedure of Example 11 was followed except that 901 mg (3.0 mmol) of 2-(4-nitroanilino)-4H-pyrido[3,2-e]-1,3-thiazin-4-one, 30 mg of lithium hydride and 616 mg of benzyl bromide were used. The resulting residue was then purified through silica gel column chromatography (eluant: chloroform) to obtain 880 mg of 3-benzyl-2,3-dihydro-2-[(4-nitrophenyl)imino]-4H-pyrido[3,2-e]-1,3-thiazin-4-one (75%, recrystallized from a mixture of ether and hexane).

Melting point: 162.5–163.5° C.

Elementary analysis (for $C_{20}H_{15}N_4O_3S$):

|  | C (%) | H (%) | N (%) | S (%) |
|---|---|---|---|---|
| Calcd.: | 61.37 | 3.86 | 14.31 | 8.19 |
| Found: | 61.54 | 3.63 | 14.35 | 8.28 |

EXAMPLE 43

3-Benzyl-2,3-dihydro-2-[(4-iodophenyl)imino]-4H-pyrido[3,2-e]-1,3-thiazin-4-one

The reaction procedure of Example 11 was followed except that 901 mg (2.36 mmol) of 2-(4-iodoanilino)-4H-pyrido[3,2-e]-1,3-thiazin-4-one, 23 mg of lithium hydride and 458 mg of benzyl bromide were used. The resulting residue was then purified through silica gel column chromatography (eluant: chloroform) to obtain 678 mg of 3-benzyl-2,3-dihydro-2-[(4-iodophenyl)imino]-4H-pyrido[3,2-e]-1,3-thiazin-4-one (61%, recrystallized from a mixture of ether and hexane).

Melting point: 162.5–163.5° C.

Elementary analysis (for $C_{20}H_{15}N_4OSI$):

|  | C (%) | H (%) | N (%) | S (%) | I (%) |
|---|---|---|---|---|---|
| Calcd.: | 50.97 | 2.99 | 8.29 | 6.80 | 26.93 |
| Found: | 50.74 | 2.89 | 8.78 | 6.81 | 26.97 |

EXAMPLE 44

3-Methyl-2-phenylimino-2,3-dihydro-4H-pyrido[3,2-e]-1,3-thiazin-4-one

The reaction procedure of Example 11 was followed except that 255 mg of 2-anilino-4H-pyrido[3,2-e]-1,3-thiazin-4-one, 9 mg of lithium hydride and 0.063 ml of methyl iodide were used. As a result, 113 mg of 3-methyl-2-phenylimino-2,3-dihydro-4H-pyrido[3,2-e]-1,3-thiazin-4-one was obtained.

Melting point: 189–190° C.

Elementary analysis (for $C_{14}H_{11}N_3OS$):

|  | C (%) | H (%) | N (%) | S (%) |
|---|---|---|---|---|
| Calcd.: | 62.43 | 4.12 | 15.60 | 11.91 |
| Found: | 62.40 | 4.11 | 15.63 | 12.01 |

EXAMPLE 45

3-Ethyl-2-phenylimino-2,3-dihydro-4H-pyrido[3,2-e]-1,3-thiazin-4-one

The reaction procedure of Example 11 was followed except that 255 mg of 2-anilino-4H-pyrido[3,2-e]-1,3-thiazin-4-one, 9 mg of lithium hydride and 0.081 ml of ethyl iodide were used. As a result, 204 mg of 3-ethyl-2-phenylimino-2,3-dihydro-4H-pyrido[3,2-e]-1,3-thiazin-4-one was obtained.

Melting point: 117–118° C.

Elementary analysis (for $C_{15}H_{13}N_3OS$):

|  | C (%) | H (%) | N (%) | S (%) |
|---|---|---|---|---|
| Calcd.: | 63.58 | 4.62 | 14.83 | 11.32 |
| Found: | 63.38 | 4.54 | 14.77 | 11.43 |

EXAMPLE 46

3-Phenylimino-3-propyl-2,3-dihydro-4H-pyrido[3,2-e]-1,3-thiazin-4-one

The reaction procedure of Example 11 was followed except that 255 mg of 2-anilino-4H-pyrido[3,2-e]-1,3-thiazin-4-one, 9 mg of lithium hydride and 0.098 ml of propyl iodide were used. As a result, 212 mg of 2-phenylimino-3-propyl-2,3-dihydro-4H-pyrido[3,2-e]-1,3-thiazin-4-one was obtained.

Melting point: 94–95° C.

Elementary analysis (for $C_{16}H_{15}N_3OS$):

|  | C (%) | H (%) | N (%) | S (%) |
| --- | --- | --- | --- | --- |
| Calcd.: | 64.62 | 5.08 | 14.13 | 10.78 |
| Found: | 64.76 | 5.09 | 14.24 | 10.97 |

EXAMPLE 47

3-Isopropyl-2-phenylimino-2,3-dihydro-4H-pyrido[3,2-e]-1,3-thiazin-4-one

The reaction procedure of Example 11 was followed except that 383 mg of 2-anilino-4H-pyrido[3,2-e]-1,3-thiazin-4-one, 14 mg of lithium hydride and 0.15 ml of isopropyl iodide were used. As a result, 144 mg of 3-isopropyl-2-phenylimino-2,3-dihydro-4H-pyrido[3,2-e]-1,3-thiazin-4-one was obtained.

Melting point: 85–86° C.

Elementary analysis (for $C_{16}H_{15}N_3OS$):

|  | C (%) | H (%) | N (%) | S (%) |
| --- | --- | --- | --- | --- |
| Calcd.: | 64.62 | 5.08 | 14.13 | 10.78 |
| Found: | 64.65 | 5.07 | 14.12 | 10.72 |

EXAMPLE 48

3-Butyl-2-phenylimino-2,3-dihydro-4H-pyrido[3,2-e]-1,3-thiazin-4-one

The reaction procedure of Example 11 was followed except that 383 mg of 2-anilino-4H-pyrido[3,2-e]-1,3-thiazin-4-one, 14 mg of lithium hydride and 0.17 ml of butyl iodide were used. As a result, 280 mg of 3-butyl-2-phenylimino-2,3-dihydro-4H-pyrido[3,2-e]-1,3-thiazin-4-one was obtained.

Melting point: 68–69° C.

Elementary analysis (for $C_{17}H_{17}N_3OS$):

|  | C (%) | H (%) | N (%) | S (%) |
| --- | --- | --- | --- | --- |
| Calcd.: | 65.57 | 5.50 | 13.49 | 10.30 |
| Found: | 65.80 | 5.48 | 13.62 | 10.35 |

EXAMPLE 49

3-Allyl-2-phenylimino-2,3-dihydro-4H-pyrido[3,2-e]-1,3-thiazin-4-one

The reaction procedure of Example 11 was followed except that 383 mg of 2-anilino-4H-pyrido[3,2-e]-1,3-thiazin-4-one, 14 mg of lithium hydride and 0.13 ml of allyl bromide were used. As a result, 297 mg of 3-allyl-2-phenylimino-2,3-dihydro-4H-pyrido[3,2-e]-1,3-thiazin-4-one was obtained.

Melting point: 94–95° C.

Elementary analysis (for $C_{16}H_{13}N_3OS$):

|  | C (%) | H (%) | N (%) | S (%) |
| --- | --- | --- | --- | --- |
| Calcd.: | 65.06 | 4.44 | 14.23 | 10.86 |
| Found: | 65.29 | 4.39 | 14.24 | 11.05 |

EXAMPLE 50

3-Benzyl-2-phenylimino-2,3-dihydro-4H-pyrido[3,2-e]-1,3-thiazin-4-one

The reaction procedure of Example 11 was followed except that 150 mg of 2-anilino-4H-pyrido[3,2-e]-1,3-thiazin-4-one, 6 mg of lithium hydride and 0.070 ml of benzyl bromide were used. As a result, 130 mg of 3-benzyl-2-phenylimino-2,3-dihydro-4H-pyrido[3,2-e]-1,3-thiazin-4-one was obtained.

Melting point: 105–106° C.

Elementary analysis (for $C_{20}H_{15}N_3OS$):

|  | C (%) | H (%) | N (%) | S (%) |
| --- | --- | --- | --- | --- |
| Calcd.: | 69.54 | 4.38 | 12.16 | 9.28 |
| Found: | 69.74 | 4.43 | 12.22 | 9.10 |

EXAMPLE 51

3-(2-Diethylaminoethyl)-2,3-dihydro-2-[(4-methylphenyl)imino]-4H-pyrido[3,2-e]-1,3-thiazin-4-one monohydrochloride The reaction procedure of Example 11 was followed except that 900 mg (3.34 mmol) of 2-(4-methylanilino)-4H-pyrido[3,2-e]-1,3-thiazin-4-one, 54 mg of lithium hydride and 633 mg of 2-diethylaminoethylchloride hydrochloride were used. The resulting residue was then purified through silica gel column chromatography (eluant: chloroform-3% methanol). The resulting compound was then recrystallized from a mixture of ether and hexane containing 4 N hydrogen hydride in dioxane to obtain 556 mg of 3-(2-diethylaminoethyl)-2,3-dihydro-2-[(4-methylphenyl)imino]-4H-pyrido[3,2-e]-1,3-thiazin-4-one monohydrochloride.

Mass spectrum (m/z): 369 ($M^+$)

Nuclear magnetic resonance spectrum (DMSO-$d_6$, TMS internal standard) δ: 1.27 (6H, t, J=7.1 Hz), 2.33 (3H, s), 3.20–3.30 (4H, m), 3.40–3.41 (2H, m), 4.60 (2H, t, J=6.8 Hz), 6.88 (2H, d, J=8.3 Hz), 7.25 (2H, d, J=8.3 Hz), 7.51 (1H, dd, J=4.9, 7.8 Hz), 8.50 (1H, dd, J=2.0, 7.8 Hz), 8.70 (1H, dd, J=2.0, 4.1 Hz)

EXAMPLE 52

3-(2-Diethylaminoethyl)-2-phenylimino-2,3-dihydro-4H-pyrido[3,2-e]-1,3-thiazin-4-one The reaction procedure of Example 11 was followed except that 383 mg of 2-anilino-4H-pyrido[3,2-e]-1,3-thiazin-4-one, 14 mg of lithium hydride and 259 mg of 2-diethylaminoethylchloride hydrochloride were used. As a result, 254 mg of 3-(2-diethylaminoethyl)-2-phenylimino-2,3-dihydro-4H-pyrido[3,2-e]-1,3-thiazin-4-one was obtained.

Melting point: 61–62° C.

Elementary analysis (for $C_{19}H_{22}N_4OS$):

|  | C (%) | H (%) | N (%) | S (%) |
|---|---|---|---|---|
| Calcd.: | 64.38 | 6.26 | 15.81 | 9.05 |
| Found: | 64.36 | 6.21 | 15.83 | 9.08 |

EXAMPLE 53

3-Propyl-2-[(4-trifluoromethylphenyl)imino]-2,3-dihydro-4H-pyrido[3,2-e]-1,3-thiazin-4-one The reaction procedure of Example 11 was followed except that 646 mg of 2-(4-trifluoromethylanilino)-4H-pyrido[3,2-e]-1,3-thiazin-4-one, 18 mg of lithium hydride and 0.19 ml of propyl iodide were used. As a result, 546 mg of 3-propyl-2-[(4-trifluoromethylphenyl)imino]-2,3-dihydro-4H-pyrido[3,2-e]-1,3-thiazin-4-one was obtained.

Melting point: 114–116° C.

Elementary analysis (for $C_{17}H_{14}F_3N_3OS$):

|  | C (%) | H (%) | N (%) | S (%) | F (%) |
|---|---|---|---|---|---|
| Calcd.: | 55.88 | 3.86 | 11.50 | 8.78 | 15.60 |
| Found: | 55.87 | 3.81 | 11.50 | 8.75 | 15.82 |

EXAMPLE 54

3-Benzyl-2-[(4-trifluoromethylphenyl)imino]-2,3-dihydro-4H-pyrido[3,2-e]-1,3-thiazin-4-one The reaction procedure of Example 11 was followed except that 646 mg of 2-(4-trifluoromethylanilino)-4H-pyrido[3,2-e]-1,3-thiazin-4-one, 18 mg of lithium hydride and 0.24 ml of benzyl bromide were used. As a result, 630 mg of 3-benzyl-2-[(4-trifluoromethylphenyl)imino]-2,3-dihydro-4H-pyrido[3,2-e]-1,3-thiazin-4-one was obtained.

Melting point: 126–128° C.

Elementary analysis (for $C_{21}H_{14}F_3N_3OS$):

|  | C (%) | H (%) | N (%) | S (%) | F (%) |
|---|---|---|---|---|---|
| Calcd.: | 61.01 | 3.41 | 10.16 | 7.76 | 13.79 |
| Found: | 60.97 | 3.42 | 10.29 | 7.72 | 14.06 |

EXAMPLE 55

Ethyl 4-[(3-methyl-4-oxo-2,3-dihydro-4H-pyrido[3,2-e]-1,3-thiazin-2-ylidene)amino]benzoate The reaction procedure of Example 11 was followed except that 1.31 g of ethyl 4-[(4-oxo-4H-pyrido[3,2-e]-1,3-thiazin-2-yl)amino]benzoate, 36 mg of lithium hydride and 0.25 ml of methyl iodide were used. As a result, 656 mg of ethyl 4-[(3-methyl-4-oxo-2,3-dihydro-4H-pyrido[3,2-e]-1,3-thiazin-2-ylidene)amino]benzoate was obtained.

Melting point: 182–184° C.

Elementary analysis (for $C_{17}H_{15}N_3O_3S$):

|  | C (%) | H (%) | N (%) | S (%) |
|---|---|---|---|---|
| Calcd.: | 59.81 | 4.43 | 12.31 | 9.39 |
| Found: | 59.63 | 4.43 | 12.23 | 9.53 |

EXAMPLE 56

Ethyl 4-[(4-oxo-3-propyl-2,3-dihydro-4H-pyrido[3,2-e]-1,3-thiazin-2-ylidene)amino]benzoate The reaction procedure of Example 11 was followed except that 1.31 g of ethyl 4-[(4-oxo-4H-pyrido[3,2-e]-1,3-thiazin-2-yl)amino]benzoate, 36 mg of lithium hydride and 0.39 ml of methyl iodide were used. As a result, 934 mg of ethyl 4-[(4-oxo-3-propyl-2,3-dihydro-4H-pyrido[3,2-e]-1,3-thiazin-2-ylidene)amino]benzoate was obtained.

Melting point: 115–117° C.

Elementary analysis (for $C_{19}H_{19}N_3O_3S$):

|  | C (%) | H (%) | N (%) | S (%) |
|---|---|---|---|---|
| Calcd.: | 61.77 | 5.18 | 11.37 | 8.68 |
| Found: | 61.70 | 5.15 | 11.34 | 8.70 |

EXAMPLE 57

2-[N-Ethyl-N-(4-methylphenyl)amino]-4H-pyrido[3,2-e]-1,3-thiazin-4-one

In a 100 ml flask, 1.595 g of 2-chloronicotinic acid, 15 ml of thionyl chloride and two droplets of DMF were heated under reflux for 2 hours. The resulting reaction mixture was allowed to cool, and then concentrated under reduced pressure. The resulting residue was then dissolved in 5 ml of acetone. In a 50 ml flask, 770 mg of ammonium thiocyanate and 15 ml of acetone were stirred to make a solution. To the flask was then connected a dropping funnel which contained the aforementioned acetone solution of 2-chloronicotinoyl chloride. The acetone solution was then added dropwise to the ammonium thiocyanate solution. The mixture was then stirred for 15 minutes. The insoluable matters which had thus separated out were removed by filtration. The filtrate was then put in a 50 ml flask. To the flask was then connected a dropping funnel which contained a mixture of 1.37 g of N-ethyl-p-toluidine and 10 ml of acetone. The toluidine solution was then added dropwise to the acyl isothiocyanate solution with stirring. The mixture was then further stirred for 1 hour. The resulting reaction mixture was poured into ice-water. The resulting precipitate was collected by filtration, washed with water, and then dried under reduced pressure. The resulting crude product was then recrystallized from ethanol to obtain 2.66 g of 2-[N-ethyl-N-(4-methylphenyl)amino]-4H-pyrido[3,2-e]-1,3-thiazin-4-one.

Melting point: 157.5–158.5° C.
Elementary analysis (for $C_{16}H_{15}N_3OS$):

|         | C (%) | H (%) | N (%) | S (%) |
|---------|-------|-------|-------|-------|
| Calcd.: | 64.62 | 5.08  | 14.13 | 10.78 |
| Found:  | 64.29 | 4.99  | 14.00 | 10.69 |

EXAMPLE 58

2-(N-Methyl-N-phenylamino)-4H-pyrido[3,2-e]-1,3-thiazin-4-one

The reaction procedure of Example 57 was followed except that 1.757 g (11.2 mmol) of 2-chloronicotinic acid, 15 ml of thionyl chloride, two droplets of DMF, 891 mg of ammonium thiocyanate, 15 ml of acetone, 1.26 g of N-methylaniline and 10 ml of acetone were used. The product was then recrystallized from ethanol to obtain 2.37 g of 2-(N-ethyl-N-phenylamino)-4H-pyrido[3,2-e]-1,3-thiazin-4-one.

Melting point: 174–175° C.
Elementary analysis (for $C_{14}H_{11}N_3OS$):

|         | C (%) | H (%) | N (%) | S (%)  |
|---------|-------|-------|-------|--------|
| Calcd.: | 62.43 | 4.12  | 15.60 | 11.91  |
| Found:  | 62.44 | 4.14  | 15.61 | 131.96 |

EXAMPLE 59

2-(N-Phenyl-N-propylamino)-4H-pyrido[3,2-e]-1,3-thiazin-4-one

The reaction procedure of Example 57 was followed except that 1.763 g (11.2 mmol) of 2-chloronicotinic acid, 15 ml of thionyl chloride, two droplets of DMF, 894 mg of ammonium thiocyanate, 15 ml of acetone, 1.59 g of N-propylaniline and 10 ml of acetone were used. The product was then recrystallized from ethanol to obtain 2.68 g of 2-(N-phenyl-N-propylamino)-4H-pyrido[3,2-e]-1,3-thiazin-4-one.

Melting point: 141–142° C.
Elementary analysis (for $C_{16}H_{15}N_3OS$):

|         | C (%) | H (%) | N (%) | S (%) |
|---------|-------|-------|-------|-------|
| Calcd.: | 64.62 | 5.08  | 14.13 | 10.78 |
| Found:  | 64.47 | 5.11  | 14.03 | 11.08 |

EXAMPLE 60

2-(N-Phenyl-N-(2-propyl)amino)-4H-pyrido[3,2-e]-1,3-thiazin-4-one

The reaction procedure of Example 57 was followed except that 1.753 g (11.1 mmol) of 2-chloronicotinic acid, 15 ml of thionyl chloride, two droplets of DMF, 894 mg of ammonium thiocyanate, 15 ml of acetone, 1.59 g of N-(2-propyl)aniline and 10 ml of acetone were used. The product was then recrystallized from ethanol to obtain 2.75 g of 2-(N-phenyl-N-(2-propyl)amino)-4H-pyrido[3,2-e]-1,3-thiazin-4-one.

Melting point: 175–176° C.
Elementary analysis (for $C_{16}H_{15}N_3OS$):

|         | C (%) | H (%) | N (%) | S (%) |
|---------|-------|-------|-------|-------|
| Calcd.: | 64.62 | 5.08  | 14.13 | 10.78 |
| Found:  | 64.50 | 5.10  | 14.03 | 10.74 |

EXAMPLE 61

2-(N-Benzyl-N-phenylamino)-4H-pyrido[3,2-e]-1,3-thiazin-4-one

The reaction procedure of Example 57 was followed except that 1.757 g (11.2 mmol) of 2-chloronicotinic acid, 15 ml of thionyl chloride, two droplets of DMF, 891 mg of ammonium thiocyanate, 15 ml of acetone, 2.15 g of N-benzylaniline and 10 ml of acetone were used. The product was then recrystallized from ethanol to obtain 2.84 g of 2-(N-benzyl-N-phenylamino)-4H-pyrido[3,2-e]-1,3-thiazin-4-one.

Melting point: 137–138° C.
Elementary analysis (for $C_{20}H_{15}N_3OS$):

|         | C (%) | H (%) | N (%) | S (%) |
|---------|-------|-------|-------|-------|
| Calcd.: | 69.54 | 4.38  | 12.16 | 9.28  |
| Found:  | 69.29 | 4.45  | 12.07 | 9.38  |

EXAMPLE 62

2-[N-(4-Bromophenyl)-N-ethylamino)-4H-pyrido[3,2-e]-1,3-thiazin-4-one

The reaction procedure of Example 57 was followed except that 1.203 g (7.63 mmol) of 2-chloronicotinic acid, 15 ml of thionyl chloride, two droplets of DMF, 639 mg of ammonium thiocyanate, 15 ml of acetone, 1.53 g of N-ethyl-4-bromoaniline and 10 ml of acetone were used. The product was then recrystallized from ethanol to obtain 2.08 g of 2-[N-(4-bromophenyl)-N-ethylamino)-4H-pyrido[3,2-e]-1,3-thiazin-4-one.

Melting point: 166–167° C.
Elementary analysis (for $C_{15}H_{12}N_3OSBr$):

|         | C (%) | H (%) | N (%) | S (%) | Br (%) |
|---------|-------|-------|-------|-------|--------|
| Calcd.: | 49.73 | 3.34  | 11.60 | 8.85  | 22.06  |
| Found:  | 49.63 | 3.25  | 11.46 | 8.81  | 22.15  |

EXAMPLE 63

2-[N-Methyl-N-(4-nitrophenyl)amino]-4H-pyrido[3,2-e]-1,3-thiazin-4-one

The reaction procedure of Example 57 was followed except that 1.757 g (11.2 mmol) of 2-chloronicotinic acid, 15 ml of thionyl chloride, two droplets of DMF, 891 mg of ammonium thiocyanate, 15 ml of acetone, 1.78 g of N-methyl-4-nitroaniline and 10 ml of acetone were used. The product was then recrystallized from ethanol to obtain 2.85 g of 2-[N-methyl-N-(4-nitrophenyl)amino]-4H-pyrido[3,2-e]-1,3-thiazin-4-one.

Melting point: 223–224° C.

Elementary analysis (for $C_{14}H_{10}N_4O_3S$):

|        | C (%) | H (%) | N (%) | S (%) |
|--------|-------|-------|-------|-------|
| Calcd.: | 53.50 | 3.21  | 17.82 | 10.20 |
| Found:  | 53.28 | 3.19  | 17.84 | 10.21 |

EXAMPLE 64

2-[N-(4-Chlorophenyl)-N-methylamino]-4H pyrido[3,2-e]-1,3-thiazin-4-one 1.757 g (11.2 mmol) of 2-chloronicotinic acid, 15 ml of thionyl chloride and two droplets of DMF were heated under reflux for 2 hours. The resulting reaction solution was allowed to cool, and then concentrated under reduced pressure. 2-chloronicotinoyl chloride thus obtained was dissolved in 10 ml of acetone, and then packed into a dropping funnel. 891 mg of ammonium thiocyanate was then dissolved in 15 ml of acetone. The aforementioned acetone solution of acid chloride was then added dropwise to the ammonium thiocyanate solution with stirring in 5 minutes. The reaction solution was then heated to a temperature of 40° C. for 5 minutes. The resulting insoluble matters were then removed by filtration. To the acetone solution of 2-chloronicotinoyl isothiocyanate was then added dropwise a mixture of 1.66 g of 4-chloro-N-methylaniline and 10 ml of acetone with stirring in 5 minutes. After the termination of dropwise addition, the reaction mixture was further stirred for 15 hours. The resulting reaction mixture was poured into an about 1,000 ml of ice-water. The compound thus precipitated was collected by filtration, washed with water, and then dried under reduced pressure. The resulting crude product was then recrystallized from ethanol to obtain 2.95 g of 2-[N-(4-chlorophenyl)-N-methylamino]-4H-pyrido[3,2-e]-1,3-thiazin-4-one.

Melting point: 189–190° C.

Nuclear magnetic resonance spectrum (CDCl$_3$, TMS internal standard) δ: 3.63 (3H, s), 7.31 (2H, d, J=8.6 Hz), 7.39 (1H, dd, J=4.9, 7.9 Hz), 7.52 (2H, d, J=8.6 Hz), 8.59 (1H, dd, J=1.8, 4.9 Hz), 8.67 (1H, dd, J=1.8, 7.9 Hz)

EXAMPLE 65

2-[N-Propyl-N-(4-trifluoromethylphenyl)amino]-4H-pyrido[3,2-e]-1,3-thiazin-4-one The reaction procedure of Example 57 was followed except that 158 mg of 2-chloronicotinoyl chloride, 68 mg of ammonium thiocyanate and 185 mg of 4-(propylamino)benzotrifluoride were used. As a result, 106 mg of 2-[N-propyl-N-(4-trifluoromethylphenyl)amino]-4H-pyrido[3,2-e]-1,3-thiazin-4-one was obtained.

Melting point: 216–217° C.

Elementary analysis (for $C_{17}H_{14}F_3N_3OS$):

|        | C (%) | H (%) | N (%) | S (%) | F (%) |
|--------|-------|-------|-------|-------|-------|
| Calcd.: | 55.88 | 3.86  | 11.50 | 8.78  | 15.60 |
| Found:  | 55.79 | 3.84  | 11.49 | 8.79  | 15.65 |

EXAMPLE 66

2-[N-Benzyl-N-(4-trifluoromethylphenyl)amino]-4H-pyrido[3,2-e]-1,3-thiazin-4-one The reaction procedure of Example 57 was followed except that 190 mg of 2-chloronicotinoyl chloride, 83 mg of ammonium thiocyanate and 271 mg of 4-(benzylamino)benzotrifluoride were used. As a result, 252 mg of 2-[N-benzyl-N-(4-trifluoromethylphenyl)amino]-4H-pyrido[3,2-e]-1,3-thiazin-4-one was obtained.

Melting point: 171–173° C.

Elementary analysis (for $C_{21}H_{14}F_3N_3OS$):

|        | C (%) | H (%) | N (%) | S (%) | F (%) |
|--------|-------|-------|-------|-------|-------|
| Calcd.: | 61.01 | 3.41  | 10.16 | 7.76  | 13.79 |
| Found:  | 61.01 | 3.36  | 10.13 | 7.78  | 13.84 |

EXAMPLE 67

Ethyl 4-[N-methyl-N-(4-oxo-4H-pyrido[3,2-e]-1,3-thiazin-2-yl)amino]benzoate The reaction procedure of Example 57 was followed except that 162 mg of 2-chloronicotinoyl chloride, 72 mg of ammonium thiocyanate and 169 mg of ethyl 4-(methylamino)benzoate were used. As a result, 279 mg of ethyl 4-[N-methyl-N-(4-oxo-4H-pyrido[3,2-e]-1,3-thiazin-2-yl)amino]benzoate was obtained.

Nuclear magnetic resonance spectrum (CDCl$_3$, TMS internal standard) δ: 1.40–1.48 (3H, m), 3.67 (3H, s), 4.40–4.48 (2H, m), 7.39 (1H, dd, J=7.9, 4.9 Hz), 7.45 (2H, d, J=7.9 Hz), 8.22 (2H, d, J=7.9 Hz), 8.56–8.61 (1H, m), 8.67 (1H, dd, J=7.9, 1.8 Hz)

Mass spectrum (m/z): 342 (M$^+$+1)

EXAMPLE 68

Ethyl 4-[N-(4-oxo-4H-pyrido[3,2-e]-1,3-thiazin-2-yl)-N-propylamino]benzoate The reaction procedure of Example 57 was followed except that 230 mg of 2-chloronicotinoyl chloride, 100 mg of ammonium thiocyanate and 270 mg of ethyl 4-(propylamino)benzoate were used. As a result, 418 mg of ethyl 4-[N-(4-oxo-4H-pyrido[3,2-e]-1,3-thiazin-2-yl)-N-propylamino)benzoate was obtained.

Melting point: 155–157° C.

Elementary analysis (for $C_{19}H_{19}N_3O_3S$):

|  | C (%) | H (%) | N (%) | S (%) |
|---|---|---|---|---|
| Calcd.: | 61.77 | 5.18 | 11.37 | 8.68 |
| Found: | 61.54 | 5.09 | 11.29 | 8.79 |

EXAMPLE 69

2-(1,2,3,4-Tetrahydroquinolin-1-yl)-4H-pyrido[3,2-e]-1,3-thiazin-4-one

The reaction procedure of Example 57 was followed except that 1.595 mg (10.12 mmol) of 2-chloronicotinic acid, 15 ml of thionyl chloride, two droplets of DMF, 770 mg of ammonium thiocyanate, 15 ml of acetone, 1.35 g of 1,2,3,4-tetrahydroquinoline and 10 ml of acetone were used. As a result, 2.18 g of 2-(1,2,3,4-tetrahydroquinolin-1-yl)-4H-pyrido[3,2-e]-1,3-thiazin-4-one was obtained.

Melting point: 174–175° C.

Elementary analysis (for $C_{16}H_{13}N_3OS$):

|  | C (%) | H (%) | N (%) | S (%) |
|---|---|---|---|---|
| Calcd.: | 65.06 | 4.44 | 14.23 | 10.86 |
| Found: | 64.71 | 4.54 | 14.09 | 10.84 |

EXAMPLE 70

2-(Indolin-1-yl)-4H-pyrido[3,2-e]-1,3-thiazin-4-one

The reaction procedure of Example 57 was followed except that 1.728 mg (10.97 mmol) of 2-chloronicotinic acid, 15 ml of thionyl chloride, two droplets of DMF, 913 mg of ammonium thiocyanate, 15 ml of acetone, 1.31 g of indoline and 10 ml of acetone were used. As a result, 2.45 g of 2-(indolin-1-yl)-4H-pyrido[3,2-e]-1,3-thiazin-4-one was obtained.

Melting point: 249–250° C.

Elementary analysis (for $C_{15}H_{11}N_3OS$):

|  | C (%) | H (%) | N (%) | S (%) |
|---|---|---|---|---|
| Calcd.: | 64.04 | 3.94 | 14.94 | 11.40 |
| Found: | 64.07 | 3.99 | 14.90 | 11.53 |

EXAMPLE 71

2-(2-Methylindolin-1-yl)-4H-pyrido[3,2-e]-1,3-thiazin-4-one

The reaction procedure of Example 57 was followed except that 1.757 g (11.2 mmol) of 2-chloronicotinic acid, 15 ml of thionyl chloride, two droplets of DMF, 891 mg of ammonium thiocyanate, 15 ml of acetone, 1.26 g of N-methylaniline and 10 ml of acetone were used. As a result, 2.37 g of 2-(2-methylindolin-1-yl)-4H-pyrido[3,2-e]-1,3-thiazin-4-one was obtained.

Melting point: 178.7–179.7° C.

Elementary analysis (for $C_{16}H_{13}N_3OS$):

|  | C (%) | H (%) | N (%) | S (%) |
|---|---|---|---|---|
| Calcd.: | 65.06 | 4.44 | 14.23 | 10.86 |
| Found: | 65.11 | 4.37 | 14.21 | 10.92 |

EXAMPLE 72

2-[N-Methyl-N-(3-methylphenyl)amino]-4H-pyrido[3,2-e]-1,3-thiazin-4-one 1.588 g (10.08 mmol) of 2-chloroniconitic acid, 15 ml of thionyl chloride and two droplets of DMF were heated under reflux for 2 hours. The resulting reaction solution was allowed to cool, and then concentrated under reduced pressure. Then, 2-chloronicotinoyl chloride thus obtained was dissolved in 10 ml of acetone. 844 mg of ammonium thiocyanate was then dissolved in 15 ml of acetone. The aforementioned acetone solution of acid chloride was then added dropwise to the ammonium isothiocyanate solution with stirring in 5 minutes. The reaction mixture was then heated to a temperature of 40° C. for 5 minutes, and the resulting insoluble matters were removed by filtration. To the acetone solution of 2-chloronicotinoyl isothiocyanate thus obtained was then added dropwise a mixture of 1.28 g of N-methyl-m-toluidine and 10 ml of acetone at room temperature with stirring in 5 minutes. After the termination of dropwise addition, the reaction mixture was further stirred for 3 hours, and then poured into about 1,000 ml of ice-water. The resulting crude product was collected by filtration, washed with water, and then dried under reduced pressure. The resulting crude product was then recrystallized from ethanol to obtain 2.43 g of 2-[N-methyl-N-(3-methylphenyl)amino]-4H-pyrido[3,2-e]-1,3-thiazin-4-one.

Melting point: 176–170° C.

Nuclear magnetic resonance spectrum (CDCl$_3$, TMS internal standard) δ: 2.43 (3H, s), 3.66 (3H, s), 7.13 (1H, s), 7.15 (1H, s), 7.33 (1H, d, J=8 Hz), 7.37 (1H, dd, J=4.9, 7.9 Hz), 7.42 (1H, t, J=7.8 Hz), 8.57 (1H, dd, J=1.8, 4.9 Hz), 8.67 (1H, dd, J=1.8, 7.9 Hz)

EXAMPLE 73

2-(N-Methyl-N-(2-methylphenyl)amino]-4H-pyrido[3,2-e]-1,3-thiazin-4-one

The reaction procedure of Example 57 was followed except that 1.613 mg (10.24 mmol) of 2-chloronicotinic acid, 15 ml of thionyl chloride, two droplets of DMF, 780 mg of ammonium thiocyanate, 15 ml of acetone, 1.21 g of N-methyl-o-toluidine and 10 ml of acetone were used. The resulting crude product was then recrystallized from ethanol to obtain 2.28 g of 2-(N-methyl-N-(2-methylphenyl)amino)-4H-pyrido[3,2-e]-1,3-thiazin-4-one.

Melting point: 208–209° C.

Elementary analysis (for $C_{15}H_{13}N_3OS$):

|  | C (%) | H (%) | N (%) | S (%) |
|---|---|---|---|---|
| Calcd.: | 63.58 | 4.62 | 14.83 | 11.32 |
| Found: | 63.62 | 4.59 | 14.78 | 11.34 |

EXAMPLE 74

2-(N-Ethyl-N-(3,4-methylenedioxyphenyl)amino]-4H-pyrido[3,2-e]-1,3-thiazin-4-one The reaction procedure of Example 57 was followed except that 1.585 mg (10.08 mmol) of 2-chloronicotinic acid, 15 ml of thionyl chloride, two droplets of DMF, 844 mg of ammonium thiocyanate, 15 ml of acetone, 1.83 g of N-ethyl-3,4-methylenedioxyaniline and 10 ml of acetone were used. The resulting crude product was then recrystallized from a mixture of ethanol and ether to obtain 1.91 g of 2-[N-ethyl-N-(3,4-methylenedioxyphenyl)amino]-4H-pyrido[3,2-e]-1,3-thiazin-4-one.

Melting point: 184–185° C.

Elementary analysis (for $C_{16}H_{13}N_3O_3S$):

|  | C (%) | H (%) | N (%) | S (%) |
|---|---|---|---|---|
| Calcd.: | 58.70 | 4.00 | 12.84 | 9.80 |
| Found: | 58.62 | 4.02 | 12.80 | 9.85 |

EXAMPLE 75

2-[N-Methyl-N-(4-trifluoromethoxylphenyl)amino]-4H-pyrido[3,2-e]-1,3-thiazin-4-one The reaction procedure of Example 57 was followed except that 824 mg (5.23 mmol) of 2-chloronicotinoyl chloride, 10 ml of thionyl chloride, two droplets off DMF, 400 mg of ammonium thiocyanate, 10 ml of acetone, 1.0 g of N-methyl-4-trifluoromethoxyaniline and 10 ml of acetone were used. The resulting crude product was then recrystallized from ethanol to obtain 1.49 g of 2-[N-methyl-N-(4-trifluoromethoxylphenyl)amino]-4H-pyrido[3,2-e]-1,3-thiazin-4-one.

Melting point: 176–177° C.

Elementary analysis (for $C_{15}H_{10}N_3O_2SF_3$):

|  | C (%) | H (%) | N (%) | S (%) | F (%) |
|---|---|---|---|---|---|
| Calcd.: | 50.99 | 2.85 | 11.89 | 9.08 | 16.13 |
| Found: | 50.91 | 2.89 | 11.98 | 9.15 | 16.35 |

EXAMPLE 76

2-(1,2,3,4-Tetrahydroisoquinolin-2-yl)-4H-pyrido[3,2-e]-1,3-thiazin-4-one

The reaction procedure of Example 57 was followed except that 1.718 g (10.90 mmol) of 2-chloronicotinic acid, 15 ml of thionyl chloride, two droplets of DMF, 872 mg of ammonium thiocyanate, 15 ml of acetone, 1.52 g of 1,2,3,4-tetrahydroisoquinoline and 15 ml of acetone were used. The resulting crude product was then recrystallized from ethanol to obtain 1.58 g of 2-(1,2,3,4-tetrahydroisoquinolin-2-yl)-4H-pyrido[3,2-e]-1,3-thiazin-4-one.

Melting point: 159–160° C.

Elementary analysis (for $C_{16}H_{13}N_3OS$):

|  | C (%) | H (%) | N (%) | S (%) |
|---|---|---|---|---|
| Calcd.: | 65.06 | 4.44 | 14.23 | 10.86 |
| Found: | 65.12 | 4.41 | 13.97 | 10.80 |

EXAMPLE 77

2-(N-Benzyl-N-methylamino)-4H-pyrido[3,2-e]-1,3-thiazin-4-one

The reaction procedure of Example 57 was followed except that 1.757 g (11.2 mmol) of 2-chloronicotinic acid, 15 ml of thionyl chloride, two droplets of DMF, 891 mg of ammonium thiocyanate, 15 ml of acetone, 1.42 g of N-methylbenzylamine and 10 ml of acetone were used. The resulting crude product was then recrystallized from a mixture of ethanol and ether to obtain 1.53 g of 2-(N-benzyl-N-methylamino)-4H-pyrido[3,2-e]-1,3-thiazin-4-one.

Melting point: 112.5–113° C.

Elementary analysis (for $C_{15}H_{13}N_3OS$):

|  | C (%) | H (%) | N (%) | S (%) |
|---|---|---|---|---|
| Calcd.: | 63.58 | 4.62 | 14.83 | 11.32 |
| Found: | 63.62 | 4.53 | 14.92 | 11.48 |

EXAMPLE 78

2-(N-Methyl-N-phenethylamino)-4H-pyrido[3,2-e]-1,3-thiazin-4-one

The reaction procedure of Example 57 was followed except that 1.792 g (11.37 mmol) of 2-chloronicotinic acid, 15 ml of thionyl chloride, two droplets of DMF, 909 mg of ammonium thiocyanate, 15 ml of acetone, 1.61 g of N-methylphenethylamine and 10 ml of acetone were used. The product was then recrystallized from ethanol to obtain 1.91 g of 2-(N-methyl-N-phenethylamino)-4H-pyrido[3,2-e]-1,3-thiazin-4-one.

Melting point: 115–116° C.

Elementary analysis (for $C_{16}H_{15}N_3OS$):

|  | C (%) | H (%) | N (%) | S (%) |
|---|---|---|---|---|
| Calcd.: | 64.62 | 5.08 | 14.13 | 10.78 |
| Found: | 64.83 | 5.07 | 14.18 | 11.01 |

EXAMPLE 79

2-(N-Cyclohexyl-N-methylamino)-4H-pyrido[3,2-e]-1,3-thiazin-4-one

The reaction procedure of Example 57 was followed except that 1.749 g (11.10 mmol) of 2-chloronicotinic acid, 15 ml of thionyl chloride, two droplets of DMF, 888 mg of ammonium thiocyanate, 15 ml of acetone, 1.32 g of N-methylcyclohexylamine and 10 ml of acetone were used. The resulting crude product was then recrystallized from ethanol to obtain 1.43 g of 2-(N-cyclohexyl-N-methylamino)-4H-pyrido[3,2-e]-1,3-thiazin-4-one.

Melting point: 134–135° C.

Elementary analysis (for $C_{14}H_{17}N_3OS$):

|  | C (%) | H (%) | N (%) | S (%) |
|---|---|---|---|---|
| Calcd.: | 61.06 | 6.22 | 15.26 | 11.64 |
| Found: | 61.02 | 6.23 | 15.39 | 11.79 |

EXAMPLE 80

2-(4-Methylpiperazin-1-yl)-4H-pyrido[3,2-e]-1,3-thiazin-4-one monohydrochloride

The reaction procedure of Example 57 was followed except that 1.595 g (10.12 mmol) of 2-chloronicotinic acid, 15 ml of thionyl chloride, two droplets of DMF, 770 mg of ammonium thiocyanate, 15 ml of acetone, 1.22 g of N-methylpiperazine and 10 ml of acetone were used. The resulting crude product was then recrystallized from a mixture of ethyl acetate, ether and hexane. The product was then subjected to salt forming with 4 N hydrochloric acid and ethyl acetate to obtain 1.14 g of 2-(4-methylpiperazin-1-yl)-4H-pyrido[3,2-e]-1,3-thiazin-4-one monohydrochloride.

Melting point: 167–168° C.

Elementary analysis (for $C_{12}H_{14}N_4OS \cdot HCl$):

|  | C (%) | H (%) | N (%) | S (%) | Cl (%) |
|---|---|---|---|---|---|
| Calcd. | 48.24 | 5.06 | 18.75 | 10.73 | 11.87 |
| Found: | 48.01 | 5.13 | 18.67 | 10.71 | 11.69 |

EXAMPLE 81

2-[(±)-Exo-norbornan-2-yl]amino-4H-pyrido[3,2-e]-1,3-thiazin-4-one 1.595 g (10.12 mmol) of 2-chloronicotinic acid, 15 ml of thionyl chloride and two droplets of DMF were heated under reflux in a 100 ml flask for 2 hours. The reaction mixture was allowed to cool to room temperature, and then concentrated under reduced pressure.

A mixture of 770 mg of ammonium thiocyanate and 15 ml of acetone was then stirred in a 50 ml flask. To the mixture was then added dropwise a solution of the acid chloride obtained by the aforementioned reaction in 5 ml of acetone. After the termination of the reaction, the reaction mixture was stirred for 10 minute. The resulting insoluble matters were then removed by filtration. The resulting filtrate was then put in another 100 ml flask.

A dropping funnel which contained 1.13 g of (±)-exo-2-norbornylamine and 15 ml of acetone was then attached to the aforementioned flask. The amine solution was then added dropwise to the filtrate with stirring. After the termination of dropwise addition, the mixture was stirred for 5 hours, and then concentrated under reduced pressure. To the resulting residue was then added 20 ml of toluene. The mixture was then heated under reflux for 2 hours. The reaction mixture was allowed to cool, and then concentrated under reduced pressure. To the resulting residue was then added ethyl acetate. The reside was washed with water and then with saturated brine. The material was dried over anhydrous sodium sulfate, and then concentrated under reduced pressure. The resulting crude product was purified through silica gel column chromatography (eluant: chloroform), and then recrystallized from a mixture of ether and hexane to obtain 1,200 mg of 2-[(+)-exo-norbornan-2-yl]amino-4H-pyrido[3,2-e]-1,3-thiazin-4-one.

Melting point: 219–220° C.

Elementary analysis (for $C_{14}H_{15}N_3OS$):

|  | C (%) | H (%) | N (%) | S (%) |
|---|---|---|---|---|
| Calcd.: | 61.51 | 5.53 | 15.37 | 11.73 |
| Found: | 61.50 | 5.45 | 15.52 | 11.76 |

EXAMPLE 82

2-[N-(4-Chlorophenyl)-N-methylamino)-7-methyl-4H-pyrido[3,2-e]-1,3-thiazin-4-one The reaction procedure of Example 57 was followed except that 2.175 g (12.68 mmol) of 2-chloro-6-methylnicotinic acid, 15 ml of thionyl chloride, two droplets of DMF, 1.01 g of ammonium thiocyanate, 15 ml of acetone, 1.81 g of N-methyl-4-chloroaniline and 10 ml of acetone were used. The resulting crude product was then recrystallized from ethanol to obtain 1.58 g of 2-[N-(4-chlorophenyl)-N-methylamino)-7-methyl-4H-pyrido[3,2-e]-1,3-thiazin-4-one.

Melting point: 196–197° C.

Elementary analysis (for $C_{15}H_{12}N_3OSCl$):

|  | C (%) | H (%) | N (%) | S (%) | Cl (%) |
|---|---|---|---|---|---|
| Calcd.: | 56.69 | 3.81 | 13.22 | 10.09 | 11.16 |
| Found: | 56.57 | 3.78 | 13.08 | 10.17 | 11.03 |

EXAMPLE 83

2-(6-Bromo-1,2,3,4-tetrahydroquinolin-1-yl)-4H-pyrido[3,2-e]-1,3-thiazin-4-one

The reaction procedure of Example 57 was followed except that 1.829 g (11.61 mmol) of 2-chloronicotinic acid, 15 ml of thionyl chloride, two droplets of DMF, 972 mg of ammonium thiocyanate, 15 ml of acetone, 2.462 g of 6-bromo-1,2,3,4-tetrahydroquinoline and 10 ml of acetone were used. The resulting crude product was then recrystallized from a mixture of ethanol, ether and hexane to obtain 2.350 g of 2-(5-bromo-1,2,3,4-tetrahydroquinolin-1-yl)-4H-pyrido[3,2-e]-1,3-thiazin-4-one.

Melting point: 173–174° C.

Elementary analysis (for $C_{15}H_{12}N_3OSBr$):

|  | C (%) | H (%) | N (%) | S (%) | Br (%) |
|---|---|---|---|---|---|
| Calcd.: | 51.35 | 3.23 | 11.23 | 8.57 | 21.35 |
| Found: | 51.39 | 3.13 | 11.20 | 8.62 | 21.26 |

EXAMPLE 84

2-(6,8-Dibromo-1,2,3,4-tetrahydroquinolin-1-yl)-4H-pyrido[3,2-e]-1,3-thiazin-4-one monohydrate The reaction procedure of Example 57 was followed except that 1.339 g (8.5 mmol) of 2-chloronicotinic acid, 13 ml of thionyl chloride, two droplets of DMF, 680 mg of ammonium isothiocyanate, 13 ml of acetone, 2.473 g of 6,8-dibromo-1,2,3,4-tetrahydroquinoline and 8 ml of acetone were used. The product was then recrystallized from a mixture of ethanol and hexane to obtain 2.244 g of 2-(1,2,3,4-tetrahydroquinolin-1-yl)-4H-pyrido[3,2-e]-1,3-thiazin-4-one monohydrate.

Melting point: >110° C. (decomposition)

Elementary analysis (for $C_{16}H_{11}N_3OSBr \cdot H_2O$):

|  | C (%) | H (%) | N (%) | S (%) | Br (%) |
|---|---|---|---|---|---|
| Calcd.: | 40.79 | 2.78 | 8.92 | 6.81 | 33.92 |
| Found: | 40.70 | 2.60 | 8.90 | 6.92 | 34.16 |
| Mass spectrum (m/z): 453 (M⁺) | | | | | |

EXAMPLE 85

2-[N-(2,3-Dihydro-1,4-benzodioxan-6-yl]-N-ethylamino-4H-pyrido[3,2-e]-1,3-thiazin-4-one 1.891 g (12.0 mmol) of 2-chloronicotinic acid, 15 ml of thionyl chloride and two droplets of DMF were heated under reflux for 2 hours. The reaction mixture was allowed to cool, and then concentrated under reduced pressure. 2-Chloronicotinoyl chloride thus obtained was then dissolved in 10 ml of acetone. 770 mg of ammonium thiocyanate was it then dissolved in 15 ml of acetone with stirring. To the solution thus obtained was then added dropwise the acetone solution of 2-chloronicotinoyl chloride in 5 minutes. The mixture was then stirred. The mixture was then stirred over a 40° C. oil bath for 5 minutes. The insoluble matters thus precipitated were then removed by filtration to obtain an acetone solution of 2-chloronicotinoyl isothiocyanate. To the solution thus obtained was then added dropwise a mixture of 2.151 g of N-ethyl-3,4-ethylenedioxyaniline and 10 ml of acetone with stirring at room temperature in 5 minutes. The reaction mixture was stirred at room temperature for 16 hours, and then poured into about 1,000 ml of ice-water. The resulting crystal was collected by filtration, washed with water, and then dried under reduced pressure. The resulting product was then recrystallized from ethanol to obtain 2.18 g of 2-[N-(2,3-dihydro-1,4-benzodioxan-6-yl]-N-ethylamino-4H-pyrido[3,2-e]-1,3-thiazin-4-one.

Melting point: 192–193° C.

Nuclear magnetic resonance spectrum (CDCl$_3$, TMS internal standard) δ: 1.27 (3H, t, J=7.0 Hz), 4.14 (2H, q, J=7.0 Hz), 4.32 (2H, d, J=8.6 Hz), 4.34 (2H, d, J=8.6 Hz), 6.78 (1H, dd, J=2.4, 8.5 Hz), 6.82 (1H, d, J=2.4 Hz), 7.00 (1H, d, J=8.5 Hz), 7.35 (1H, dd, J=4.9, 7.9 Hz), 8.56 (1H, dd, J=1.8, 4.9 Hz), 8.65 (1H, dd, J=1.8, 7.9 Hz)

EXAMPLE 86

2-[N-(3,4-Dimethoxyphenyl)-N-ethylamino]-4H-pyrido[3,2-e]-1,3-thiazin-4-one

The reaction procedure of Example 85 was followed except that 1.733 g (11 mmol) of 2-chloronicotinic acid, 15 ml of thionyl chloride, two droplets of DMF, 880 mg of ammonium isothiocyanate, 15 ml of acetone, 1.993 g of 3,4-dimethoxy-N-ethylaniline and 10 ml of acetone were used. The product was then recrystallized from ethanol to obtain 3.388 g of 2-[N-(3,4-dimethoxyphenyl)-N-ethylaminoj-4H-pyrido[3,2-e]-1,3-thiazin-4-one.

Melting point: 209–210° C.

Elementary analysis (for C$_{17}$H$_{17}$N$_3$O$_3$S):

|  | C (%) | H (%) | N (%) | S (%) |
|---|---|---|---|---|
| Calcd.: | 59.46 | 4.99 | 12.24 | 9.34 |
| Found: | 59.27 | 4.93 | 12.15 | 9.35 |

EXAMPLE 87

2-[N-Ethyl-N-(3-methoxyphenyl)amino]-4H-pyrido[3,2-e]-1,3-thiazin-4-one

The reaction procedure of Example 85 was followed except that 1.891 g (12 mmol) of 2-chloronicotinic acid, 15 ml of thionyl chloride, two droplets of DMF, 960 mg of ammonium thiocyanate, 15 ml of acetone, 1.815 g of 3-methoxy-N-ethylaniline and 10 ml of acetone were used. The resulting crude product was then recrystallized from ethanol to obtain 3.107 g of 2-[N-(3-methoxyphenyl)-N-ethylamino]-4H-pyrido[3,2-e]-1,3-thiazin-4-one.

Melting point: 135.5–136.5° C.

Elementary analysis (for C$_{16}$H$_{15}$N$_3$O$_2$S):

|  | C (%) | H (%) | N (%) | S (%) |
|---|---|---|---|---|
| Calcd.: | 61.32 | 4.82 | 13.41 | 10.23 |
| Found: | 61.39 | 4.79 | 13.42 | 10.40 |

EXAMPLE 88

2-[N-Ethyl-N-(4-isopropylphenyl)amino]-4H-pyrido[3,2-e]-1,3-thiazin-4-one

The reaction procedure of Example 85 was followed except that 2.347 g (15.1 mmol) of 2-chloronicotinic acid, 30 ml of thionyl chloride, three droplets of DMF, 1.262 g of ammonium thiocyanate, 15 ml of acetone, 2.583 g of N-ethyl-4-isopropylaniline and 10 ml of acetone were used. The resulting crude product was then recrystallized from a mixture of ethanol, ether and hexane to obtain 3.388 g of 2-[N-ethyl-N-(4-isopropylphenyl)amino]-4H-pyrido[3,2-e]-1,3-thiazin-4-one.

Mass spectrum (m/z): 326 (M$^+$+1)

Nuclear magnetic resonance spectrum (CDCl$_3$, TMS internal standard) δ: 1.26–1.32 (9H, m), 3.00 (1H, qq, J=7.2 Hz), 4.18 (2H, q, J=7.2 Hz), 7.22 (2H, d, J=8.0 Hz), 7.35 (1H, dd, J=4.4, 7.6 Hz), 7.38 (2H, d, J=8.0 Hz), 8.55 (1H, dd, J=2.0, 4.4 Hz), 8.66 (1H, dd, J=2.0, 7.6 Hz)

EXAMPLE 89

2-[N-Ethyl-N-(4-acetylphenyl)amino]-4H-pyrido[3,2-e]-1,3-thiazin-4-one

The reaction procedure of Example 85 was followed except that 1.576 g (10 mmol) of 2-chloronicotinic acid, 10 ml of thionyl chloride, two droplets of DMF, 837 mg of ammonium thiocyanate, 10 ml of acetone, 3.986 g of 4-acetyl-N-ethylaniline and 10 ml of acetone were used. The resulting crude product was then recrystallized from ethanol to obtain 2.729 g of 2-[N-ethyl-N-(4-acetylphenyl)amino]-4H-pyrido[3,2-e]-1,3-thiazin-4-one.

Melting point: 203.5–204.5° C.

Elementary analysis (for C$_{17}$H$_{15}$N$_3$O$_2$S):

|  | C (%) | H (%) | N (%) | S (%) |
|---|---|---|---|---|
| Calcd.: | 62.75 | 4.65 | 12.91 | 9.85 |
| Found: | 62.57 | 4.66 | 12.80 | 9.82 |

EXAMPLE 90

2-[N-Ethyl-N-(1H-1-methylbenzimidazol-5-yl)amino]-4H-pyrido[3,2-e]-1,3-thiazin-4-one hydrochloride A mixture of 1.512 g (9.5 mmol) of 2-chloronicotinic acid, 15 ml of thionyl chloride and two droplets of DMF was heated under reflux for 2 hours. The reaction mixture was allowed to cool, and then concentrated under reduced pressure. The resulting residue was then dissolved in 10 ml of acetone to obtain an acetone solution of 2-chloronicotinoyl chloride. 804 mg of ammonium thiocyanate was then dissolved in 15 ml of acetone. To the solution thus obtained was then added dropwise the acetone solution of 2-chloronicotinoyl chloride with stirring in 5 minutes. The reaction mixture was then stirred over a 40° C. oil bath for 5 minutes. The resulting insoluble matters were then removed by filtration to obtain an acetone solution of 2-chloronicotinoyl isothiocyanate. To the solution thus obtained was then added dropwise a mixture of 1.685 g of 5-(N-ethylamino)-1-methyl-1H-benzimidazole and 10 ml of acetone with stirring in 5 minutes. The reaction mixture was further stirred for 6 hours, and then poured into about 1,000 ml of ice-water. The resulting crystal was collected by filtration, washed with water, and then dried under reduced pressure. The compound thus obtained was suspended in 30 ml of toluene, and then heated under reflux for 2 hours. After allowed to cool, the reaction mixture was collected by filtration, and then recrystallized from a mixture of ethanol and ether to obtain 1.171 g of 2-[N-ethyl-N-(1H-1-methylbenzimidazol-5-yl)amino]-4H-pyrido[3,2-e]-1,3-thiazin-4-one hydrochloride.

Mass spectrum (m/z): 338 ($M^+$+1)

Nuclear magnetic resonance spectrum (CDCl$_3$, TMS internal standard) δ: 1.20 (3H, t, J=7.3 Hz), 4.05 (3H, s), 4.13 (2H, q, J=7.3 Hz), 7.55 (1H, dd, J=4.6, 7.9 Hz), 7.64 (1H, d, J=6.7 Hz), 8.05 (1H, d, J=6.7 Hz), 8.07 (1H, s), 8.51 (1H, dd, J=1.8, 7.9 Hz), 8.66 (1H, dd, J=1.8, 4.6 Hz)

EXAMPLE 91

2-(1H-2,3,4,5-Tetrahydro-1-benzazepin-1-yl)-4H-pyrido[3,2-e]-1,3-thiazin-4-one

The reaction procedure of Example 85 was followed except that 1.576 g (10 mmol) of 2-chloronicotinic acid, 13 ml of thionyl chloride, three droplets of DMF, 837 mg of ammonium thiocyanate, 13 ml of acetone, 1.549 g of 1H-2,3,4,5-tetrahydro-1-benzazepine and 12 ml of acetone were used. The product was then recrystallized from ethanol to obtain 2.565 g of 2-(1H-2,3,4,5-tetrahydro-1-benzazepin-1-yl)-4H-pyrido[3,2-e]-1,3-thiazin-4-one.

Melting point: 235–236° C.

Elementary analysis (for $C_{17}H_{15}N_3OS$):

|  | C (%) | H (%) | N (%) | S (%) |
|---|---|---|---|---|
| Calcd.: | 66.00 | 4.89 | 13.58 | 10.36 |
| Found: | 65.91 | 4.91 | 13.43 | 10.29 |

EXAMPLE 92

2-[N-(4-Chlorophenyl)-N-methylamino]-7-phenyl-4H-pyrido[3,2-e]-1,3-thiazin-4-one A mixture of 2.150 g (10 mmol) of 2-hydroxy-6-phenylnicotinic acid, 30 ml of thionyl chloride and two droplets of DMF was heated under reflux for 5 days. The reaction mixture was allowed to cool to room temperature, and then concentrated under reduced pressure. The resulting residue was then dissolved in 20 ml of THF. The solution thus obtained was then added dropwise to a mixture of 840 mg of ammonium thiocyanate, 15 ml of THF and 10 ml of acetone with stirring in 5 minutes. The reaction mixture was then stirred over a 40° C. oil bath for 5 minutes. The resulting insoluble matters were then removed by filtration. To the resulting filtrate was then added dropwise a mixture of 1.416 g of N-methyl-4-chloroaniline and 10 ml of THF with stirring in 5 minutes. The reaction mixture was stirred at room temperature for 17 hours, and then concentrated under reduced pressure. To the resulting residue was then added 15 ml of THF. The residue was then heated under reflux for 4 hours. The reaction mixture was then allowed to cool. The resulting crystal was collected by filtration, washed with THF and then with ethanol, and then dried under reduced pressure. The compound thus obtained was washed with hot ethanol, and then dried under reduced pressure to obtain 918 mg of 2-[N-(4-chlorophenyl)-N-methylamino]-7-phenyl-4H-pyrido[3,2-e]-1,3-thiazin-4-one.

Melting point: 279.2–280.2° C.

Elementary analysis (for $C_{20}H_{14}N_3OSCl$):

|  | C (%) | H (%) | N (%) | S (%) | Cl (%) |
|---|---|---|---|---|---|
| Calcd.: | 63.24 | 3.71 | 11.06 | 8.44 | 9.33 |
| Found: | 63.17 | 3.59 | 11.08 | 8.19 | 9.43 |

EXAMPLE 93

2-[N-(4-Hydroxyaminophenyl)-N-methylamino]-4H-pyrido[3,2-e]-1,3-thiazin-4-one

A mixture of 1.181 g (3.76 mmol) of 2-[N-methyl-N-(4-nitrophenyl)amino]-4H-pyrido[3,2-e]-1,3-thiazin-4-one obtained in Example 63, 100 ml of DMF and 250 mg of 10% Pd on carbon was stirred in an atmosphere of hydrogen for 6 days. The reaction mixture was then heated so that the compound thus precipitated was dissolved. The insoluble matters were hot-removed by filtration. The solution thus obtained was then allowed to cool to room temperature. The resulting crystal was collected by filtration, washed with THF and then with ethanol, and then dried under reduced pressure to obtain 77 mg of 2-[N-(4-hydroxyaminophenyl)-N-methylamino]-4H-pyrido[3,2-e]-1,3-thiazin-4-one.

Mass spectrum (m/z): 301 ($M^+$+1)

Nuclear magnetic resonance spectrum (CDCl$_3$, TMS internal standard) δ: 3.48 (3H, s), 6.97 (2H, d, J=8.8 Hz), 7.30 (2H, d, J=8.8 Hz), 7.53 (1H, dd, J=4.8, 8.0 Hz), 8.49 (1H, dd, J=1.6, 8.0 Hz), 8.57 (1H, d, J=1.6 Hz), 8.66 (1H, dd, J=1.6, 4.8 Hz), 8.70 (1H, bs)

EXAMPLE 94

2-[N-(4-Aminophenyl)-N-methylamino]-4H-pyrido[3,2-e]-1,3-thiazin-4-one

A mixture of 1.505 g (4.79 mmol) of 2-[N-methyl-N-(4-nitrophenyl)amino]-4H-pyrido[3,2-e]-1,3-thiazin-4-one obtained in Example 63, 50 ml of DMF and about 1.5 g of Raney nickel was stirred in an atmosphere of hydrogen for 5 hours. The resulting insoluble matters were then removed by filtration. The resulting filtrate was then concentrated under reduced pressure. The residue was then recrystallized from ethanol to obtain 984 mg of 2-[N-(4-aminophenyl)-N-methylamino]-4H-pyrido[3,2-e]-1,3-thiazin-4-one.

Melting point: 249.5–250.5° C.
Elementary analysis (for $C_{14}H_{12}N_4OS$):

|  | C (%) | H (%) | N (%) | S (%) |
|---|---|---|---|---|
| Calcd.: | 59.14 | 4.25 | 19.70 | 11.28 |
| Found: | 58.98 | 4.32 | 19.42 | 11.51 |

EXAMPLE 95

2-[N-(4-Chlorophenyl)-N-methylamino]-4H-pyrido[4,3-e]-1,3-thiazin-4-one 1) 1-(4-Chlorophenyl)-3-(3-fluoroisonicotinoyl)-1-methylthiourea A mixture of 1.658 g (11.75 mmol) of 3-fluoroisonicotinic acid, 15 ml of thionyl chloride and three droplets of DMF was heated under reflux for 2 hours. The reaction mixture was allowed to cool, and then concentrated under reduced pressure to obtain 3-fluoroisonicotinoyl chloride. The compound thus obtained was then dissolved in 10 ml of acetone. The solution thus obtained was then added dropwise to a solution of 984 mg of ammonium thiocyanate in 15 ml of acetone with stirring in 5 minutes. After the termination of dropwise addition, the reaction mixture was heated to a temperature of 40° C. with stirring for 5 minutes. The resulting insoluble matters were then removed by filtration to obtain an acetone solution of 3-fluoroisonicotinoyl isothiocyanate. To the solution thus obtained was then added dropwise a solution of 1.55 g of 4-chloro-N-methylaniline in 10 ml of acetone with stirring for 5 minutes. The reaction mixture was stirred at room temperature for 17 hours, and then poured into about 1,000 ml of ice-water. The resulting crystal was collected by filtration, washed with water, and then dried under reduced pressure. The resulting crude product was then purified through silica gel column chromatography (eluant: $CHCl_3$+2% methanol) to obtain 1.452 g of 1-(4-chlorophenyl)-3-(3-fluoroisonicotinoyl)-1-methylthiourea.

Mass spectrum (m/z): 324 ($M^+$+1)

Nuclear magnetic resonance spectrum ($CDCl_3$, TMS internal standard) δ: 3.72 (3H, s), 7.26 (2H, d, J=8.8 Hz), 7.39 (2H, d, J=8.8 Hz), 7.64 (1H, bs), 8.50–8.55 (2H, m), 8.73 (1H, bs)

2) 2-[N-(4-Chlorophenyl)-N-methylamino]-4H-pyrido[4,3-e]-1,3-thiazin-4-one

In an atmosphere of argon, a suspension of 167 mg of sodium hydride (60% oil suspension) in 1 ml of THF was added to a mixture of 1.230 g (3.80 mmol) of 1-(4-chlorophenyl)-3-(3-fluoroisonicotinoyl)-1-methylthiourea and 10 ml of DMF while being cooled over a water bath. The mixture was stirred for 10 minutes, and then stirred over a 110° C. oil bath for 5 hours. The reaction mixture was allowed to cool, and then concentrated under reduced pressure. The resulting residue was then poured into ice-water. The resulting precipitate was collected by filtration, washed with water, and then dried under reduced pressure. The resulting crude product was then recrystallized from ethanol to obtain 802 mg of 2-[N-(4-chlorophenyl)-N-methylamino]-4H-pyrido[4,3-e]-1,3-thiazin-4-one.

Melting point: 255–256° C.

Nuclear magnetic resonance spectrum (DMSO-$d_6$, TMS internal standard) δ: 3.51 (3H, s), 7.63 (2H, d, J=8.8 Hz), 7.70 (2H, d, J=8.8 Hz), 8.02 (1H, d, J=4.8 Hz), 8.66 (1H, d, J=4.8 Hz), 8.83 (1H, s)

EXAMPLE 96

2-[N-(4-Chlorophenyl)-N-methylamino]-4H-pyrido[3,4-e]-1,3-thiazin-4-one

A mixture of 1.416 g (8.99 mmol) of 4-chloronicotinic acid, 15 ml of thionyl chloride and two droplets of DMF was heated under reflux for 2 hours. The reaction mixture was allowed to cool, and then concentrated under reduced pressure to obtain 4-chloronicotinoyl chloride. The compound thus obtained was then suspended in a mixture of 10 ml of acetone and 10 ml of THF. The suspension thus obtained was then added dropwise to a solution of 753 mg of ammonium thiocyanate in 15 ml of acetone with stirring in 5 minutes. After the termination of dropwise addition, the reaction mixture was heated to a temperature of 40° C. with stirring for 6 minutes to obtain a mixture containing 4-chloronicotinoyl isothiocyanate. To the mixture thus obtained was then added dropwise a solution of 1.55 g of 4-chloro-N-methylaniline in 10 ml of acetone with stirring in 5 minutes. The reaction mixture was stirred at room temperature for 17 hours, concentrated to half the initial volume under reduced pressure, and then poured into about 500 ml of ice-water. The resulting crystal was collected by filtration, washed with water, and then dried under reduced pressure. The resulting crude product was purified through silica gel column chromatography (eluant: $CHCl_3$+1 to 3% methanol), and then recrystallized from ethanol to obtain 717 mg of 2-[N-(4-chlorophenyl)-N-methylamino]-4H-pyrido[3,4-e]-1,3-thiazin-4-one.

Melting point: 238–239° C.

Nuclear magnetic resonance spectrum (DMSO-$d_6$, TMS internal standard) δ: 3.61 (3H, s), 7.07 (1H, d, J=5.2 Hz), 7.31 (2H, d, J=8.8 Hz), 7.54 (2H, d, J=8.8 Hz), 8.57 (1H, d, J=5.2 Hz), 9.26 (1H, s)

EXAMPLE 97

2-(N-Methyl-N-(l-methyl-4-piperidinyl)amino]-4H-pyrido[3,2-e]-1,3-thiazin-4-one hydrochloride A mixture of 2.437 g (15.47 mmol) of 2-chloronicotinic acid, 15 ml of thionyl chloride and two droplets of DMF was heated under reflux for two hours. The reaction solution was allowed to cool, and then concentrated under reduced pressure to obtain 2-chloronicotinoyl chloride. The compound thus obtained was then dissolved in 10 ml of acetone. The solution thus obtained was then added dropwise to a solution of 1.30 g of ammonium thiocyanate in 15 ml of acetone with stirring in 5 minutes. After the termination of dropwise addition, the reaction mixture was heated to a temperature of 40° C. with stirring for 6 minutes. The resulting insoluble matters were then removed by filtration to obtain a solution of 2-chloronicotinoyl isothiocyanate. To the solution was then added dropwise a solution of 1.98 g of 1-methyl-4-(methylamino)piperidine in 10 ml of THF with stirring in 5 minutes. The reaction mixture was stirred at room temperature for 17 hours, and then concentrated under reduced pressure. The resulting residue was then purified through silica gel column chromatography (eluant: 20:1:0.1 to 10:1:0.1 mixture of $CHCl_3$, methanol and 30% aqueous ammonia) to obtain 3.98 g of 1-(1-methyl-4-piperidyl)-3-(2-chloronicotinoyl)-1-methylthiourea.

The compound thus obtained was then dissolved in 30 ml of DMF. The solution thus obtained was heated over a 140° C. oil bath, and then stirred for 5 hours. The reaction mixture was allowed to cool, and then condensed under reduced pressure. The resulting residue was purified through silica gel column chromatography (eluant: 20:1:0.1 to 10:1:0.1 mixture of $CHCl_3$, methanol and 30% aqueous ammonia), subjected to salt formation with a 4 N ethyl acetate solution of hydrogen chloride, and then recrystallized from iPrOH to obtain 2.448 g of 2-[N-methyl-N-(1-methyl-4-piperidinyl)amino]-4H-pyrido[3,2-e]-1,3-thiazin-one hydrochloride.

Mass spectrum (m/z): 291 (M$^+$+1)

Nuclear magnetic resonance spectrum (DMSO-d$_6$, TMS internal standard) δ: 1.8–2.0 (2H, m), 2.34–2.37 (2H, m), 2.74 (3H, d, J=4.4 Hz), 3.12 (3H, s), 3.12–3.25 (2H, m), 3.4–3.53 (3H, m), 7.60 (1H, dd, J=4.8, 8.0 Hz), 8.51 (1H, d, J=8.0 Hz), 8.76 (1H, d, J=4.8 Hz)

EXAMPLE 98

2-[N-(2-Hydroxyethyl)-N-phenylamino]-4H-pyrido[3,2-e]-1,3-thiazin-4-one

A mixture of 2.565 g (16.28 mmol) of 2-chloronicotinic acid, 20 ml of thionyl chloride and two droplets of DMF was heated under reflux for 2 hours. The resulting reaction solution was allowed to cool, and then concentrated under reduced pressure to obtain 2-chloronicotinoyl chloride. The compound thus obtained was dissolved in 15 ml of acetone. The solution thus obtained was then added dropwise to a solution of 1.363 g of ammonium thiocyanate in 15 ml of acetone with stirring in 5 minutes. After the termination of dropwise addition, the reaction mixture was heated to a temperature of 40° C. with stirring for 5 minutes to obtain a solution of 4-chloronicotinoyl isothiocyanate. To the solution thus obtained was then added dropwise a solution of 1.363 g of N-(2-hydroxyethyl)aniline in 15 ml of THF with stirring in 5 minutes. The reaction mixture was stirred at room temperature for 17 hours, and then poured into about 1,000 ml of ice-water. The resulting crystal was collected by filtration, washed with water, and then dried under reduced pressure. The resulting crude product was then recrystallized from ethanol to obtain 777 mg of 2-[N-(2-hydroxyethyl)-N-phenylamino]-4H-pyrido[3,2-e]-1,3-thiazin-4-one.

Melting point: 168–169° C.

Elementary analysis (for $C_{15}H_{13}N_4O_4S$)

|  | C (%) | H (%) | N (%) | S (%) |
|---|---|---|---|---|
| Calcd.: | 60.18 | 4.38 | 14.04 | 10.71 |
| Found: | 59.87 | 4.26 | 13.92 | 10.53 |

EXAMPLE 99

2-(3-Pyridylamino)-4H-pyrido[3,2-e]-1,3-thiazin-4-one hydrochloride 1) 1-(2-Chloroniconinoyl)-3-(3-pyridyl)thiourea A mixture of 3.635 g (23.07 mmol) of 2-chloronicotinic acid, 20 ml of thionyl chloride and three droplets of DMF was heated under reflux for 3 hours. The reaction solution was allowed to cool, and then concentrated under reduced pressure to obtain 2-chloronicotinoyl chloride. The compound thus obtained was then dissolved in 10 ml of acetone. The solution thus obtained was then added dropwise to a solution of 1.931 g of ammonium thiocyanate in 20 ml of acetone with stirring in 5 minutes. After the termination of dropwise addition, the reaction mixture was heated to a temperature of 40° C. with stirring for 5 minutes. The resulting insoluble matters were then removed by filtration to obtain an acetone solution of 2-chloronicotinoyl isothiocyanate. To the solution thus obtained was then added dropwise a solution of 2.171 g of 3-aminopyridine in 20 ml of acetone with stirring for 5 minutes. The reaction mixture was stirred at room temperature for 17 hours, and then poured into about 1,000 ml of ice-water. The resulting crystal was collected by filtration, washed with water, and then dried under reduced pressure to obtain 3.881 g of 1-(2-chloroniconinoyl)-3-(3-pyridyl)thiourea Mass spectrum (m/z): 293 (M$^+$+1)

Nuclear magnetic resonance spectrum (DMSO-d$_6$, TMS internal standard) δ: 7.48 (1H, dd, J=4.8, 8.0 Hz), 7.58 (1H, d, J=4.8, 7.6 Hz), 8.11 (1H, ddd, J=1.6, 1.6, 8.0 Hz), 8.14 (1H, dd, J=1.6, 7.6 Hz), 8.48 (1H, dd, J=1.6, 4.8 Hz), 5 8.57 (1H, dd, J=1.6, 4.8 Hz), 8.75 (1H, d, J=2.0 Hz)

2) 2-(3-Pyridylamino)-4H-pyrido[3,2-e]-1,3-thiazin-4-one hydrochloride

A mixture of 1.104 g (3.77 mmol) of 1-(2-chloronicotinoyl)-3-(3-pyridyl)thiourea and 10 ml of DMF was heated over a 140° C. oil bath. The mixture was stirred for 1 hour. The reaction mixture was allowed to cool, and then diluted with THF. The resulting crystal was collected by filtration, washed with THF, and then dried under reduced pressure to obtain to obtain 759 mg of 2-(3-pyridylamino)-4H-pyrido[3,2-e]-1,3-thiazin-4-one hydrochloride.

Melting point: 257–258° C.

Nuclear magnetic resonance spectrum (DMSO-d$_6$, TMS internal standard) δ: 7.58 (1H, dd, J=4.8, 7.6 Hz), 7.96 (1H, dd, J=5.2, 8.0 Hz), 8.30–8.50 (1H, m), 8.53 (1H, dd, J=1.6, 8.0 Hz), 8.65 (1H, d, J=5.2 Hz), 8.76 (1H, dd, J=1.6, 8.0 Hz), 8.75–8.90 (1H, m), 12.0–13.0 (1H, m)

EXAMPLE 100

2-[N-Methyl-N-(3-pyridyl)amino]-4H-pyrido[3,2-e]-1,3-thiazin-4-one hydrochloride A mixture of 2.486 g (15.78 mmol) of 2-chloronicotinic acid, 15 ml of thionyl chloride and two droplets of DMF was heated under reflux for 2 hours. The resulting reaction solution was allowed to cool, and then concentrated under reduced pressure to obtain 2-chloronicotinoyl chloride. The compound thus obtained was dissolved in 10 ml of acetone. The solution thus obtained was then added dropwise to a solution of 1.32 g of ammonium thiocyanate in 15 ml of acetone with stirring in 5 minutes. After the termination of dropwise addition, the reaction mixture was heated to a temperature of 40° C. with stirring for 6 minutes to obtain a solution of 2-chloronicotinoyl isothiocyanate. To the solution thus obtained was then added dropwise a solution of 1.706 g of 3-(N-methylamino)pyridine in 10 ml of acetone with stirring in 5 minutes. The reaction mixture was stirred at room temperature for 17 hours, and then poured into about 1,000 ml of ice-water. The resulting crystal was collected by filtration, washed with water, and then dried under reduced pressure. The resulting crude product was recrystallized from ethanol in the presence of a 4 N ethyl acetate solution of hydrogen chloride, and then recrystallized from ethanol to obtain 2.956 g of 2-[N-methyl-N-( 3-pyridyl)amino]-4H-pyrido[3,2-e]-1,3-thiazin-4-one hydrochloride.

Mass spectrum (m/z): 271 (M$^+$)

Nuclear magnetic resonance spectrum (DMSO-d$_6$, TMS internal standard) δ: 3.60 (3H, s), 7.61 (1H, dd, J=4.8, 8.0 Hz), 7.88 (1H, dd, J=5.2, 8.4 Hz), 8.35 (1H, d, J=8.4 Hz), 8.53 (1H, dd, J=1.6, 8.4 Hz), 8.85 (1H, dd, J=1.6, 4.0 Hz), 8.58 (1H, d, J=4.8 Hz), 8.99 (1H, s)

EXAMPLE 101

2,3-Dihydro-3-methyl-2-(3-pyridylimino)-4H-pyrido[3,2-e]-1,3-thiazin-4-one 566 mg (1.93 mmol) of 2-(3-pyridylamino)-4H-pyrido[3,2-e]-1,3-thiazin-4-one was dissolved in 12 ml of DMF. To the solution thus obtained was then added dropwise a suspension of 162 mg (60% oil suspension, 2.1 eq) in 1 ml THF with stirring. The reaction mixture was then heated with stirring over a 60° C. oil bath for 30 minutes. To the reaction mixture was then added 301 mg of methyl iodide. The reaction mixture was then stirred for 4 hours. After the termination of reaction, the reaction solution was allowed to cool, and then concentrated under reduced pressure. The resulting residue was then purified through silica gel column chromatography (eluant: $CHCl_3$+1 to 2% methanol) to obtain 724 mg of an amorphous compound. The compound thus obtained was then recrystallized from ethanol to obtain 372 mg of 2,3-dihydro-3-methyl-2-(3-pyridylimino)-4H-pyrido[3,2-e]-1,3-thiazin-4-one.

Melting point: 159.5–160.5° C.

Elementary analysis (for $C_{13}H_{10}N_4OS$):

|  | C (%) | H (%) | N (%) | S (%) |
|---|---|---|---|---|
| Calcd.: | 57.76 | 3.73 | 20.73 | 11.86 |
| Found: | 57.53 | 3.63 | 20.58 | 11.85 |

EXAMPLE 102

2-[N-(4-Fluorophenyl)-N-methylamino]-4H-pyrido[3,2-e]-1,3-thiazin-4-one

A mixture of 2.226 g (14.36 mmol) of 2-chloronicotinic acid, 15 ml of thionyl chloride and two droplets of DMF was heated under reflux for 2 hours. The resulting reaction solution was allowed to cool, and then concentrated under reduced pressure to obtain 2-chloronicotinoyl chloride. The compound thus obtained was dissolved in 10 ml of acetone. The solution thus obtained was then added dropwise to a solution of 1.21 of ammonium thiocyanate in 15 ml of acetone with stirring in 5 minutes. After the termination of dropwise addition, the reaction mixture was heated to a temperature of 40° C. with stirring for 6 minutes. The resulting insoluble matters were then removed by filtration to obtain a solution of 2-chloronicotinoyl isothiocyanate. To the solution thus obtained was then added dropwise a solution of 1.80 g of 4-fluoro-N-methylaniline in 10 ml of acetone with stirring in 5 minutes. The reaction mixture was stirred at room temperature for 15 hours, and then poured into about 1,000 ml of ice-water. The resulting crystal was collected by filtration, washed with water, dried under reduced pressure, and then recrystallized from ethanol to obtain 2.99 g of 2-[N-(4-fluorophenyl)-N-methylamino]-4H-pyrido[3,2-e]-1,3-thiazin-4-one.

Melting point: 184–185° C.

Nuclear magnetic resonance spectrum (DMSO-$d_6$, TMS internal standard) δ: 3.64 (3H, s), 7.21–7.27 (2H, m), 7.33–7.37 (2H, m), 7.38 (1H, dd, J=4.8, 8.0 Hz), 8.58 (1H, dd, J=2.0, 4.8 Hz), 8.67 (1H, dd, J=2.0, 8.0 Hz)

EXAMPLE 103

2-(4-Chlorophenylimino)-2,3-dihydro-3-(3-methoxybenzyl)-4H-pyrido[3,2-e]-1,3-thiazin-4-one and 2-[N-(4-chlorophenyl)-N-(3-methoxybenzyl)amino]-4H-pyrido[3, 2-e]-1,3-thiazin-4-one The reaction procedure of Example 11 was followed except that 2.681 g (9.25 mmol) of 2-(4-chloroanilino)-4H-pyrido[3,2-e]-1,3-thiazin-4-one, 162 mg of lithium hydride, 1.50 g of 3-methoxybenzyl chloride and 40 ml of DMF were used. The resulting residue was then purified through silica gel column chromatography (eluant: chloroform). As a result, 2.288 of 2-[N-(4-chlorophenylimino)-2,3-dihydro-4H-3-(3-methoxybenzyl)pyrido[3,2-e]-1,3-thiazin-4-one (recrystallized from ethanol) was obtained as a low polarity substance, and 843 mg of 2-[N-(4-chlorophenyl)-N-(3-methoxybenzyl)amino]-4H-pyrido[3,2-e]-1,3-thiazin-4-one (recrystallized from a mixture of ethyl acetate and diisopropyl ether) was obtained as a high polarity substance.

1) 2-(4-Chlorophenylimino)-2,3-dihydro-3-(3-methoxybenzyl)pyrido[3,2-e]-1,3-thiazin-4-one Melting point: 137–138° C.

Elementary analysis (for $C_{21}H_{16}N_3O_2SCl$):

|  | C (%) | H (%) | N (%) | S (%) | Cl (%) |
|---|---|---|---|---|---|
| Calcd.: | 61.54 | 3.93 | 10.25 | 7.82 | 8.65 |
| Found: | 61.46 | 3.76 | 10.22 | 7.87 | 8.86 |

2) 2-[N-(4-Chlorophenyl)-N-(3-methoxybenzyl)amino]-4H-pyrido[3,2-e]-1,3-thiazin-4-one Melting point: 129.5–130.5° C.

Elementary analysis (for $C_{21}H_{16}N_3O_2SCl$):

|  | C (%) | H (%) | N (%) | S (%) | Cl (%) |
|---|---|---|---|---|---|
| Calcd: | 61.54 | 3.93 | 10.25 | 7.82 | 8.65 |
| Found: | 61.33 | 3.89 | 10.24 | 7.79 | 8.70 |

EXAMPLE 104

2-(4-Chlorophenylimino)-3-(5-chloro-2-thenyl)-2,3-dihydro-4H-pyrido[3,2-e]-1,3-thiazin-4-one and 2-[N-(4-chlorophenyl)-N-(5-chloro-2-thenyl)amino]-4H-pyrido[3,2-e]-1,3-thiazin-4-one The reaction procedure of Example 11 was followed except that 2.536 g (8.75 mmol) of 2-(4-chloroanilino)-4H-pyrido[3,2-e]-1,3-thiazin-4-one, 154 mg of lithium hydride, 1.462 g of 5-chloro-2-thenyl chloride and 40 ml of DMF were used. The resulting residue was then purified through silica gel column chromatography (eluant: chloroform). As a result, 2.643 of 2-(4-chlorophenylimino)-3-(5-chloro-2-thenyl)-2,3-dihydro-4H-pyrido[3,2-e]-1,3-thiazin-4-one (recrystallized from ethanol) was obtained as a low polarity substance, and 263 mg of 2-[N-(4-chlorophenyl)-N-(5-chloro-2-thenyl)amino]-4H-pyrido[3,2-e]-1,3-thiazin-4-one (recrystallized from a mixture of ethyl acetate and diisopropyl ether) was obtained as a high polarity substance.

1) 2-(4-Chlorophenylimino)-3-(5-chloro-2-thenyl)-2,3-dihydro-4H-pyrido[3,2-e]-1,3-thiazin-4-one Melting point: 153–154° C.

Elementary analysis (for $C_{18}H_{11}N_3OS_2Cl_2$):

|  | C (%) | H (%) | N (%) | S (%) | Cl (%) |
|---|---|---|---|---|---|
| Calcd.: | 51.43 | 2.64 | 10.00 | 15.26 | 6.87 |
| Found: | 51.24 | 2.71 | 10.01 | 15.08 | 6.89 |

2) 2-[N-(4-Chlorophenyl)-N-(5-chloro-2-thenyl)amino]-4H-pyrido[3,2-e]-1,3-thiazin-4-one Melting point: 187.5–188.5° C.

Elementary analysis (for $C_{18}H_{11}N_3OS_2Cl_2$):

|  | C (%) | H (%) | N (%) | S (%) | Cl (%) |
|---|---|---|---|---|---|
| Calcd.: | 51.43 | 2.64 | 10.00 | 15.26 | 6.87 |
| Found: | 51.41 | 2.52 | 10.01 | 15.32 | 7.15 |

EXAMPLE 105

2-(4-Chlorophenylimino)-2,3-dihydro-3-(2-propynyl)-4H-pyrido[3,2-e]-1,3-thiazin-4-one and 2-[N-(4-chlorophenyl)-N-(2-propynyl)amino]-4H-pyrido[3,2-e]-1,3-thiazin-4-one A mixture of 1.615 g (5.57 mmol) of 2-(4-chloroanilino)-4H-pyrido[3,2-e]-1,3-thiazin-4-one and 30 ml of DMF was heated to make a homogeneous solution. To the solution thus obtained was then added 98 mg of lithium hydride with stirring in an atmosphere of argon over a 60° C. oil bath. The reaction mixture was then stirred for 30 minutes. To the reaction mixture was then added 804 mg of 3-bromopropyne. The reaction mixture was then stirred at the same temperature for 4 hours. The reaction mixture was allowed to cool to room temperature, and then concentrated under reduced pressure. The resulting residue was then purified through silica gel column chromatography (eluant: chloroform). As a result, 2.643 g of 2-(4-chlorophenylimino)-2,3-dihydro-3-(2-propynyl)-4H-pyrido[3,2-e]-1,3-thiazin-4-one (recrystallized from ethanol) was obtained as a low polarity substance, and 263 mg of 2-[N-(4-chlorophenyl)-N-(2-propynyl)amino]-4H-pyrido[3,2-e]-1,3-thiazin-4-one (recrystallized from a mixture of ethyl acetate and diisopropyl ether) was obtained as a high polarity substance.

1) 2-(4-Chlorophenylimino)-2,3-dihydro-3-(2-propynyl)-4H-pyrido[3,2-e]-1,3-thiazin-4-one Melting point: >143° C. (decomposition)

Mass spectrum (m/z): 328 (M$^+$+1)

Nuclear magnetic resonance spectrum (CDCl$_3$, TMS internal standard) δ: 2.22 (1H, t, J=2.4 Hz), 5.14 (2H, d, J=2.4 Hz), 6.88 (2H, d, J=7.8 Hz), 7.31 (1H, dd, J=4.8, 8.4 Hz), 7.36 (2H, d, J=7.8 Hz), 8.57 (1H, dd, J=2.0, 8.4 Hz), 8.60 (1H, dd, J=2.0, 4.8 Hz)

2) 2-[N-(4-Chlorophenyl)-N-(2-propynyl)amino]-4H-pyrido[3,2-e]-1,3-thiazin-4-one Melting point: 164–165° C.

Nuclear magnetic resonance spectrum (CDCl$_3$, TMS internal standard) δ: 2.31 (1H, t, J=2.4 Hz), 4.93 (2H, d, J=2.4 Hz), 7.40 (1H, dd, J=4.0, 8.0 Hz), 7.40 (1H, d, J=8.4 Hz), 7.54 (1H, d, J=7.4 Hz), 8.59 (1H, dd, J=2.0, 4.4 Hz), 8.66 (1H, dd, J=2.0, 8.0 Hz), 6.88 (2H, d, J=8.4 Hz)

EXAMPLE 106

2-[4-(2-Methoxyphenyl)-1-piperazinyl]-4H-pyrido[3,2-e]-1,3-thiazin-4-one 1.0 g of 2-chloronicotinic acid and 10 ml of thionyl chloride were mixed. To the mixture was then added two droplets of DMF. The reaction mixture was then heated under reflux for 2 hours. The reaction mixture was allowed to cool, and then concentrated under reduced pressure. The resulting residue was then dissolved in 10 ml of acetone.

Separately, 531 mg of ammonium thiocyanate was dissolved in 10 ml of acetone. To the solution thus obtained was then added dropwise the acetone solution of residue. The mixture was then heated to a temperature of 40° C. The mixture was then stirred at room temperature for 30 minutes. The resulting insoluble matters were removed by filtration. To the resulting filtrate was then added a solution of 1.22 g of 1-(2-methoxyphenyl)piperazine in 10 ml of acetone. The mixture was then stirred at room temperature overnight.

The reaction solution was then concentrated. To the resulting residue was then added an aqueous solution of sodium hydrogencarbonate. The reaction mixture was then extracted with ethyl acetate. The resulting organic phase was washed with water and with saturated brine, dried over anhydrous magnesium sulfate, and then concentrated under reduced pressure. The resulting residue was subjected to separation through silica gel column chromatography (eluant: 1:1 mixture of benzene and ethyl acetate), and then washed with hot ethanol to obtain 733 mg of 2-[4-(2-methoxyphenyl)-1-piperazinyl]-4H-pyrido[3,2-e]-1,3-thiazine-4-one.

Melting point: 224–228° C.

Elementary analysis (for $C_{18}H_{18}N_4O_2S$):

|  | C (%) | H (%) | N (%) | S (%) |
|---|---|---|---|---|
| Calcd.: | 61.00 | 5.12 | 15.81 | 9.05 |
| Found: | 61.04 | 4.98 | 15.50 | 8.94 |

EXAMPLE 107

Ethyl 1-(4-oxo-4H-pyrido[3,2-e]-1,3-thiazin-2-yl)piperazin-4-carboxylate

The reaction procedure of Example 106 was followed except that 1.0 g of 2-chloronicotinic acid, 10 ml of thionyl chloride, 531 mg of ammonium thiocyanate and 998 mg of ethyl isopecotinate were used. The product was subjected to separation through silica gel column chromatography (eluant: 50:1 mixture of chloroform and methanol), and then recrystallized from a mixture of isopropyl ether and isopropanol to obtain 365 mg of ethyl 1-(4-oxo-4H-pyrido[3,2-e]-1,3-thiazin-2-yl)piperazin-4-carboxylate.

Melting point: 139–140° C.

Elementary analysis (for $C_{15}H_{17}N_3O_3S$):

|  | C (%) | H (%) | N (%) | S (%) |
|---|---|---|---|---|
| Calcd.: | 56.41 | 5.37 | 13.16 | 10.04 |
| Found: | 56.42 | 5.24 | 13.08 | 10.06 |

EXAMPLE 108

2-(4-Hydroxypiperidino)-4H-pyrido[3,2-e]-1,3-thiazin-4-one

The reaction procedure of Example 106 was followed except that 1.0 g of 2-chloronicotinic acid, 10 ml of thionyl chloride, 531 mg of ammonium thiocyanate and 642 mg of 4-hydroxypiperidine were used. The product was subjected to separation through silica gel column chromatography (eluant: 50:1:0.1 mixture of chloroform, methanol and aqueous ammonia), and then crystallized from isopropanol to obtain 320 mg of 2-(4-hydroxypiperidino)-4H-pyrido[3,2-e]-1,3-thiazin-4-one.

Melting point: 206–207° C.

Elementary analysis (for $C_{12}H_{13}N_3O_2S$):

|  | C (%) | H (%) | N (%) | S (%) |
|---|---|---|---|---|
| Calcd.: | 54.74 | 4.98 | 15.96 | 12.18 |
| Found: | 54.55 | 4.83 | 15.92 | 12.09 |

EXAMPLE 109

2-(3-Hydroxypiperidino)-4H-pyrido[3,2-e]-1,3-thiazin-4-one

The reaction procedure of Example 106 was followed except that 1.0 g of 2-chloronicotinic acid, 10 ml of thionyl chloride, 531 mg of ammonium thiocyanate and 642 mg of 3-hydroxypiperidine were used. The product was subjected to separation through silica gel column chromatography (eluant: 50:1:0.1 mixture of chloroform, methanol and aqueous ammonia), and then recrystallized from a mixture of isopropyl ether and isopropanol to obtain 285 mg of 2-(3-hydroxypiperidino)-4H-pyrido[3,2-e]-1,3-thiazin-4-one.

Melting point: 208–211° C.

Elementary analysis (for $C_{12}H_{13}N_3O_2S$):

|  | C (%) | H (%) | N (%) | S (%) |
|---|---|---|---|---|
| Calcd.: | 54.74 | 4.98 | 15.96 | 12.18 |
| Found: | 54.37 | 4.85 | 15.86 | 11.89 |

EXAMPLE 110

2-(3-Phenyl-1,2,5,6-tetrahydropyridin-1-yl)-4H-pyrido[3,2-e]-1,3-thiazin-4-one 455 mg of 2-chloronicotinic acid was dissolved in 15 ml of methylene chloride. To the solution thus obtained was then added 440 mg of oxalyl chloride and two droplets of DMF. The reaction mixture was then stirred at room temperature for 2 hours. The reaction mixture was concentrated under reduced pressure, and then dissolved in 10 ml of acetone. To the solution was then added 242 mg of ammonium thiocyanate. The reaction mixture was then stirred at room temperature for 1 hour. The resulting insoluble matters were removed by filtration. The resulting filtrate was then cooled to a temperature of −10° C. To the filtrate was then added a solution of 460 mg g of 3-phenyl-1,2,5,6-tetrahydropyridine in 5 ml of acetone. The mixture was stirred at a temperature of -10° C. for 30 minutes, heated to room temperature, and then stirred for 14 hours.

To the mixture were then added water and ethyl acetate. The mixture was then subjected to separation. The resulting organic phase was washed with saturated brine, dried over anhydrous magnesium sulfate, and then concentrated under reduced pressure. The resulting residue was then subjected to separation through silica gel column chromatography (eluant: 2:1 mixture of benzene and ethyl acetate), and then recrystallized from ethanol to obtain 276 mg of 2-(3-phenyl-1,2,5,6-tetrahydropyridin-1-yl)-4H-pyrido[3,2-e]-1,3-thiazin-4-one.

Melting point: 167–169° C.

Elementary analysis (for $C_{18}H_{15}N_3OS$):

|  | C (%) | H (%) | N (%) | S (%) |
|---|---|---|---|---|
| Calcd.: | 67.27 | 4.70 | 13.07 | 9.98 |
| Found: | 67.08 | 4.58 | 12.95 | 10.05 |

EXAMPLE 111

2-(4-Oxo-1-piperidinyl)-4H-pyrido[3,2-e]-1,3-thiazin-4-one 120 mg of 2-(4-hydroxypiperidino)-4H-pyrido[3,2-e]-1,3-thiazin-4-one (compound of Example 108), 250 mg of crushed molecular sieve (3A) and 7.2 ml of methylene chloride were mixed. To the mixture was then added 196 mg of pyridinium chlorochromate (PCC). The mixture was then stirred at room temperature for 1.5 hours. The reaction mixture was immediately filtered through 10 g of a silica gel layer, and then eluted with a 50:1:0.1 mixture of chloroform, methanol and aqueous ammonia. The resulting filtrate and elute were concentrated, subjected to separation through silica gel column chromatography (eluant: 50:1:0.1 mixture of chloroform, methanol and aqueous ammonia), and then washed with hot acetonitrile to obtain 72 mg of 2-(4-oxo-1-piperidinyl)-4H-pyrido[3,2-e]-1,3-thiazin-4-one.

Melting point: 222–225° C.

Elementary analysis (for $C_{12}H_{11}N_3O_2S$):

|  | C (%) | H (%) | N (%) | S (%) |
|---|---|---|---|---|
| Calcd.: | 55.16 | 4.24 | 16.08 | 12.27 |
| Found: | 55.08 | 4.26 | 16.35 | 11.93 |

EXAMPLE 112

2-[N-(4-Cyclohexylphenyl)-N-methylamino)-4H-pyrido[3,2-e]-1,3-thiazin-4-one

The reaction procedure of Example 102 was followed except that 279 mg of 2-chloronicotinoyl chloride, one droplet of DMF, 121 mg of ammonium thiocyanate, 300 mg of 4-cyclohexyl-N-methylaniline and 5 ml of acetone were used.

The product was then recrystallized from ethanol to obtain 270 mg of 2-[N-(4-cyclohexylphenyl)-N-methylamino]-4H- pyrido[3,2-e]-1,3-thiazin-4-one.

Melting point: 192–195° C.

Elementary analysis (for $C_{20}H_{21}N_3OS$)

|  | C (%) | H (%) | N (%) | S (%) |
|---|---|---|---|---|
| Calcd.: | 68.35 | 6.02 | 11.96 | 9.12 |
| Found: | 68.43 | 6.08 | 11.89 | 9.21 |

EXAMPLE 113

2-(N-(4-biphenyl)-N-methylamino]-4H-pyrido[3,2-e]-1,3-thiazin-4-one

The reaction procedure of Example 102 was followed except that 288 mg of 2-chloronicotinoyl chloride, one droplet of DMF, 125 mg of ammonium thiocyanate, 300 mg of 4-(methylamino)biphenyl and 5 ml of acetone were used. The resulting crude product was then recrystallized from a mixture of ethanol and chloroform to obtain 280 mg of 2-[N-(4-biphenyl)-N-methylamino]-4H-pyrido[3,2-e]-1,3-thiazin-4-one.

Melting point: 256–258° C.

Elementary analysis (for $C_{20}H_{15}N_3OS$):

|  | C (%) | H (%) | N (%) | S (%) |
|---|---|---|---|---|
| Calcd.: | 69.54 | 4.38 | 12.16 | 9.28 |
| Found: | 69.61 | 4.44 | 12.18 | 9.27 |

EXAMPLE 114

[4-[N-Methyl-N-(4-oxo-4H-pyrido[3,2-e]-1,3-thiazin-2-yl)amino]phenyl]acetonitrile The reaction procedure of Example 102 was followed except that 362 mg of 2-chloronicotinoyl chloride, 156 mg of ammonium thiocyanate, 300 mg of [4-(methylamino) phenyl]acetonitrile and 7 ml of acetone were used. The product was then recrystallized from a mixture of ethanol and chloroform to obtain 347 mg of [4-[N-methyl-N-(4-oxo-4H-pyrido[3,2-e]-1,3-thiazin-2-yl)amino]phenyl] acetonitrile.

Melting point: 190–192° C.

Elementary analysis (for $C_{16}H_{12}N_4OS$):

|  | C (%) | H (%) | N (%) | S (%) |
|---|---|---|---|---|
| Calcd.: | 62.32 | 3.92 | 18.17 | 10.40 |
| Found: | 62.40 | 3.83 | 18.15 | 10.38 |

EXAMPLE 115

Ethyl [4-[N-methyl-N-(4-oxo-4H-pyrido[3,2-e]-1,3-thiazin-2-yl)amino]phenyl]acetate The reaction procedure of Example 102 was followed except that 1.256 g of 2-chloronicotinoyl chloride, 543 mg of ammonium thiocyanate, 1.379 g of ethyl [4-(methylamino)phenyl]acetate and 24 ml of acetone were used. The product was then recrystallized from ethanol to obtain 1.26 g of ethyl [4-[N-methyl-N-(4-oxo-4H-pyrido[3,2-e]-1,3-thiazin-2-yl)amino]phenyl]acetate.

Melting point: 156–159° C.

Elementary analysis (for $C_{18}H_{17}N_3O_3S$):

|  | C (%) | H (%) | N (%) | S (%) |
|---|---|---|---|---|
| Calcd.: | 60.83 | 4.82 | 11.82 | 9.02 |
| Found: | 60.86 | 4.77 | 11.80 | 9.05 |

EXAMPLE 116

[4-[N-Methyl-N-(4-oxo-4H-pyrido[3,2-e]-1,3-thiazin-2-yl)amino]phenyl]acetic acid To a mixture of 250 mg of ethyl [4-[N-methyl-N-(4-oxo-4H-pyrido[3,2-e]-1,3-thiazin-2-yl)amino)phenyl]acetate and 1.55 ml of ethanol was added 1.55 ml of a 0.5 N aqueous solution of sodium hydroxide under cooling with ice. The mixture was then stirred at room temperature for 4 hours. The reaction mixture was diluted with 5 ml of water, and then adjusted with a 0.5 N hydrochloric acid to pH 1. The resulting crystal was collected by filtration, washed with water and then with diethyl ether, and then dried under reduced pressure to obtain 227 mg of [4-[N-methyl-N-(4-oxo-4H-pyrido[3,2-e]-1,3-thiazin-2-yl)amino]phenyl]acetic acid. Nuclear magnetic resonance spectrum ($CDCl_3$, TMS internal standard) δ: 3.64 (3H, s), 3.77 (2H, s), 7.33 (2H, d, J=7.6 Hz), 7.38 (1H, dd, J=8.0, 4.8 Hz), 7.49 (2H, d, J=7.6 Hz), 8.54–8.60 (1H, m), 8.67 (1H, d, J=8.0 Hz)

Mass spectrum (M/Z): 328 ($M^+$+1)

EXAMPLE 117

4-[N-Methyl-N-(4-oxo-4H-pyrido[3,2-e]-1,3-thiazin-2-yl)amino]benzoic acid

The reaction procedure of Example 116 was followed except that 70 mg g of ethyl 4-[N-methyl-N-(4-oxo-4H-pyrido[3,2-e]-1,3-thiazin-2-yl)amino]benzoate, 0.9 ml of ethanol and 0.9 ml of a 0.25 N aqueous solution of sodium hydroxide were used. As a result, 61 mg of 4-(N-methyl-N-(4-oxo-4H-pyrido[3,2-e]-1,3-thiazin-2-yl)amino]benzoic acid was obtained.

Nuclear magnetic resonance spectrum ($CDCl_3$, TMS internal standard) δ: 3.67 (3H, s), 7.39–7.47 (3H, m), 8.22 (2H, d, J=8.4 Hz), 8.57–8.68 (2H, m)

Mass spectrum (M/Z): 314 ($M^+$+1)

EXAMPLE 118

2-[N-(Indan-5-yl)-N-methylamino]-4H-pyrido[3,2-e]-1,3-thiazin-4-one 359 mg of 2-chloronicotinoyl chloride was dissolved in 2 ml of acetone. The solution was then added dropwise to a mixture of 156 mg of ammonium thiocyanate and 2 ml of acetone. The reaction mixture was then stirred at a temperature of 40° C. for 5 minutes. The resulting insoluble matters were removed by filtration. To the resulting filtrate was then added dropwise a mixture of 300 mg of 5-(methylamino) indane and 3 ml of acetone. The mixture was then stirred at room temperature for 15 hours. The mixture was then heated under reflux with stirring for 5 minutes. The mixture was allowed to cool. Water was then added to the mixture. The mixture was then extracted with chloroform.

The extract was washed with water and then with saturated brine, dried over magnesium sulfate, and then concentrated under reduced pressure. The resulting residue was purified through silica gel column chromatography (eluant: chloroform), recrystallized from ethanol, and then dried under reduced pressure to obtain 361 mg of 2-[N-(indan-5-yl)-N-methylamino]-4H-pyrido[3,2-e]-1,3-thiazin-4-one.

Melting point: 157–160° C.

Nuclear magnetic resonance spectrum ($CDCl_3$, TMS internal standard) δ: 2.17 (2H, quintet, J=7.6 Hz), 2.94–3.02 (4H, m), 3.64 (3H, s), 7.05–7.10 (1H, m), 7.16 (1H, s), 7.33–7.38 (2H, m), 8.56 (1H, dd, J=4.8, 2.0 Hz), 8.67 (1H, dd, J=8.0, 2.0 Hz)

EXAMPLE 119

2-[N-Methyl-N-(2-naphthyl)amino]-4H-pyrido[3,2-e]-1,3-thiazin-4-one

The reaction procedure of Example 102 was followed except that 336 mg g of 2-chloronicotinoyl chloride, 145 mg of ammonium thiocyanate, 300 mg of 2-(methylamino) naphthalene and 7 ml of acetone were used. The product was then recrystallized from a mixture of ethanol and chloroform to obtain 321 mg of 2-[N-methyl-N-(2-naphthyl)amino]-4H-pyrido[3,2-e]-1,3-thiazin-4-one.

Melting point: 230–232° C.

Elementary analysis (for $C_{18}H_{13}N_3OS$):

|  | C (%) | H (%) | N (%) | S (%) |
|---|---|---|---|---|
| Calcd.: | 67.69 | 4.10 | 13.16 | 10.04 |
| Found: | 67.73 | 4.02 | 13.19 | 9.99 |

EXAMPLE 120

2-[N-Methyl-N-(3-thienyl)amino]-4H-pyrido[3,2-e]-1,3-thiazin-4-one

The reaction procedure of Example 102 was followed except that 560 mg of 2-chloronicotinoyl chloride, 242 mg of ammonium thiocyanate, 360 mg of 3-(methylamino) thiophene and 10 ml of acetone were used. The product was then recrystallized from a mixture of ethanol and chloroform to obtain 230 mg of 2-[N-methyl-N-(3-thienyl)amino)-4H-pyrido[3,2-e]-1,3-thiazin-4-one.

Melting point: 231–232° C.

Elementary analysis (for $C_{12}H_9N_3OS_2$):

|  | C (%) | H (%) | N (%) | S (%) |
|---|---|---|---|---|
| Calcd.: | 52.34 | 3.29 | 15.26 | 23.29 |
| Found: | 52.57 | 3.24 | 15.53 | 23.37 |

EXAMPLE 121

2-[N-(Benzo(b]thiophen-5-yl)-N-methylamino]-4H-pyrido[3,2-e]-1,3-thiazin-4-one

The reaction procedure of Example 102 was followed except that 1.669 g of 2-chloronicotinoyl chloride, 722 mg of ammonium thiocyanate, 1.55 g of 5-(methylamino)benzo[b]thiophene and 35 ml of acetone were used. The product was then recrystallized from a mixture of ethanol and ethyl acetate to obtain 546 mg of 2-[N-(benzo[b]thiophen-5-yl)-N-methylamino]-4H-pyrido[3,2-e]-1,3-thiazin-4-one.

Melting point: 214–216° C.

Elementary analysis (for $C_{16}H_{11}N_3OS_2$):

|  | C (%) | H (%) | N (%) | S (%) |
|---|---|---|---|---|
| Calcd.: | 59.06 | 3.41 | 12.91 | 19.71 |
| Found: | 59.03 | 3.23 | 12.79 | 19.48 |

EXAMPLE 122

2-[N-Methyl-N-(quinolin-6-yl)amino]-4H-pyrido[3,2-e]-1,3-thiazin-4-one hydrochloride The reaction procedure of Example 102 was followed except that 334 mg of 2-chloronicotinoyl chloride, 145 mg of ammonium thiocyanate, 300 m of 6-(methylamino) quinoline and 7 ml of acetone were used. The resulting crude product was then washed with hot ethanol to obtain 324 mg of 2-[N-methyl-N-(quinolin-6-yl)amino]-4H-pyrido[3,2-e]-1,3-thiazin-4-one hydrochloride.

Melting point: 217–221° C.

Nuclear magnetic resonance spectrum ($CDCl_3$, TMS internal standard) δ: 3.66 (3H, s), 7.54–7.61 (1H, m), 7.78–7.85 (1H, m), 8.00–8.06 (1H, m), 8.30–8.41 (2H, m), 8.50–8.55 (1H, m), 8.65–8.72 (2H, m), 9.13–9.19 (1H, m)

EXAMPLE 123

2,3-Dihydro-2-[(4-chlorophenyl)imino]-3-(2-hydroxyethyl)-4H-pyrido[3,2-e]-1,3-thiazin-4-one and 2-[N-(4-chlorophenyl)-N-(2-hydroxyethyl) amino]-4H-pyrido[3,2-e]-1,3-thiazin-4-one In an atmosphere of argon, a mixture of 60 mg (7.6 mmol) of lithium hydride and 10 ml of DMF was put in a 100 ml flask. To the flask was then connected a dropping funnel which contained 1,600 mg (5.5 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 2 hours. To the mixture was then added a mixture of 1,034 mg of 2-bromoethanol and 4 ml of DMF. The mixture was then stirred for 22 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane). As a result, 1.48 g of 2,3-dihydro-2-[(4-chlorophenyl)imino]-3-(2-hydroxyethyl)-4H-pyrido[3,2-e]-1,3-thiazin-4-one was obtained as a low polarity substance, and 220 mg of 2-[N-(4-chlorophenyl)-N-(2-hydroxyethyl)amino]-4H-pyrido[3,2-e]-1,3-thiazin-4-one was obtained as a high polarity substance.

1) 2,3-Dihydro-2-[(4-chlorophenyl)imino-3-(2-hydroxyethyl)-4H-pyrido[3,2-e]-1,3-thiazin-4-one Melting point: 148° C.

Nuclear magnetic resonance spectrum (DMSO-$d_6$, TMS internal standard) δ: 3.70 (2H, dt, J=6.0, 7.6 Hz), 4.38 (2H, t, J=7.6 Hz), 4.87 (1H, t, J=6.0 Hz), 6.95 (2H, d, J=8.8 Hz), 7.47 (2H, d, J=8.8 Hz), 7.50 (1H, dd, J=4.8, 8.0 Hz), 8.49 (1H, dd, J=1.6, 8.0 Hz), 8.69 (1H, dd, J=1.6, 4.8 Hz)

2) 2-[N-(4-Chlorophenyl)-N-(2-hydroxyethyl)amino]-4H-pyrido[3,2-e]-1,3-thiazin-4-one Melting point: 177–178° C.

Nuclear magnetic resonance spectrum (DMSO-$d_6$, TMS internal standard) δ: 3.66 (2H, dt, J=5.6, 6.0 Hz), 4.07 (2H, t, J=6.0 Hz), 4.92 (1H, t, J=5.6 Hz), 7.56 (1H, dd, J=4.8, 8.0 Hz), 7.62 (2H, d, J=8.8 Hz), 7.68 (2H, d, J=8.8 Hz), 8.50 (1H, dd, J=0.9, 8.0 Hz), 8.69 (1H, dd, J=0.9, 4.8 Hz)

EXAMPLE 124

2,3-Dihydro-2-[(4-chlorophenyl)imino]-3-(2-methoxyethyl)-4H-pyrido[3,2-e]-1,3-thiazin-4-one and 2-[N-(4-chlorophenyl)-N-(2-methoxyethyl) amino]-4H-pyrido[3,2-e]-1,3-thiazin-4-one In an atmosphere of argon, a mixture of 26 mg (3.3 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 4 minutes. The mixture was further stirred for 50 minutes. To the mixture was then added a mixture of 576 mg of 2-bromoethyl methyl ether and 2 ml of DMF. The mixture was then stirred for 21 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/2 mixture of ethyl acetate and normal hexane). As a result, 261 mg of 2-[(4-chlorophenyl)imino]-2,3-dihydro-3-(2-methoxyethyl)-4H-pyrido[3,2-e]-1,3-thiazin-4-one was obtained as a low polarity substance, and 79 mg of 2-[N-(4-chlorophenyl)-N-(2-methoxyethyl)amino]-4H-pyrido[3,2-e]-1,3-thiazin-4-one was obtained as a high polarity substance.

1) 2-[(4-Chlorophenyl)imino]-2,3-dihydro-3-(2-methoxyethyl)-4H-pyrido[3,2-e]-1,3-thiazin-4-one Melting point: 108–109° C.

Nuclear magnetic resonance spectrum (DMSO-$d_6$, TMS internal standard) δ: 3.30 (3H, s), 3.67 (2H, t, J=6.0 Hz), 4.48 (2H, t, J=6.0 Hz), 6.96 (2H, d, J=8.4 Hz), 7.47 (2H, d, J=8.4 Hz), 7.51 (1H, dd, J=4.8, 8.0 Hz), 8.50 (1H, dd, J=1.6, 8.0 Hz), 8.70 (1H, dd, J=1.6, 4.8 Hz)

2) 2-[N-(4-Chlorophenyl)-N-(2-methoxyethyl)amino]-4H-pyrido[3,2-e]-1,3-thiazin-4-one Melting point: 124–126° C.

Nuclear magnetic resonance spectrum (DMSO-$d_6$, TMS internal standard) δ: 3.22 (3H, s), 3.57 (2H, t, J=5.6 Hz), 4.19 (2H, t, J=5.6 Hz), 7.56 (1H, dd, J=4.8, 7.6 Hz), .0 7.58 (2H, d, J=8.8 Hz), 7.69 (2H, d, J=8.8 Hz), 8.51 (1H, dd, J=2.0, 7.6 Hz), 8.69 (1H, dd, J=2.0, 4.8 Hz)

EXAMPLE 125

Ethyl 2-[2-(4-chlorophenyl)imino-4-oxo-2,3-dihydro-4H-pyrido[3,2-e]-1,3-thiazin-3-yl]acetate and ethyl 2-[N-(4-chlorophenyl)-N-(4-oxo-4H-pyrido[3,2-e]-1,3-thiazin-2-yl)amino]acetate 0.5 fumarate In an atmosphere of argon, a mixture of 34 mg (4.3 mmol) of lithium hydride and 5 ml of DMF was put in a 100 ml flask. To the flask was then connected a dropping funnel which contained 804 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 50 minutes. To the mixture was then added a mixture of 704 mg of 2-bromoethyl acetate and 1 ml of DMF. The mixture was then stirred for 22 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane). As a result, 708 mg of ethyl 2-[2-(4-chlorophenyl)imino-4-oxo-2,3-dihydro-4H-pyrido[3,2-e]-1,3-thiazin-3-yl]acetate was obtained as a low polarity substance, and 96 mg of ethyl 2-[N-(4-chlorophenyl)-N-(4-oxo-4H-pyrido[3,2-e]-1,3-thiazin-2-yl)amino]acetate was obtained as a high polarity substance. To a mixture of 89 mg of ethyl 2-[N-(4-chlorophenyl)-N-(4-oxo-4H-pyrido[3,2-e]-1,3-thiazin-2-yl)amino]acetate and 5 ml of ethanol was then added 14 mg of fumaric acid. The mixture was then stirred at room temperature for 1 hour. After the termination of reaction, the reaction was concentrated under reduced pressure, and then recrystallized from ethanol to obtain 104 mg of ethyl 2-[N-(4-chlorophenyl)-N-(4-oxo-4H-pyrido[3,2-e]-1,3-thiazin-2-yl)amino]acetate 0.5 fumarate.

1) Ethyl 2-[2-(4-chlorophenyl)imino-4-oxo-2,3-dihydro-4H-pyrido[3,2-e]-1,3-thiazin-3-yl]acetate Melting point: 151–152° C.

Nuclear magnetic resonance spectrum (DMSO-$d_6$, TMS internal standard) δ: 1.97 (3H, s), 4.39 (2H, t, J=5.6 Hz), 4.55 (2H, t, J=5.6 Hz), 6.96 (2H, d, J=8.8 Hz), 7.48 (2H, d, J=8.8 Hz), 7.51 (1H, dd, J=4.8, 8.0 Hz), 8.51 (1H, dd, J=1.6, 8.0 Hz), 8.70 (1H, dd, J=1.6, 4.8 Hz)

2) Ethyl 2-[N-(4-chlorophenyl)-N-(4-oxo-4H-pyrido[3,2-e]-1,3-thiazin-2-yl)amino]acetate 0.5 fumarate Melting point: 108–109° C.

Nuclear magnetic resonance spectrum (DMSO-$d_6$, TMS internal standard) δ: 1.94 (3H, s), 4.28 (4H, m), 6.63 (1H, s), 7.57 (1H, dd, J=4.8, 8.0 Hz), 7.63 (2H, d, J=8.8 Hz), 7.71 (2H, d, J=8.8 Hz), 8.52 (1H, dd, J=1.6, 8.0 Hz), 8.70 (1H, dd, J=1.6, 4.8 Hz), 13.11 (1H, bs)

EXAMPLE 126

2-[(4-Chlorophenyl)imino]-2,3-dihydro-3-(2-oxopropyl)-4H-pyrido[3,2-e]-1,3-thiazin-4-one and 2-[N-(4-chlorophenyl)-N-(2-oxopropyl)amino]-4H-pyrido[3,2-e]-1,3-thiazin-4-one In an atmosphere of argon, a mixture of 26 mg (3.3 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 3 minutes. The mixture was further stirred for 30 minutes. To the mixture was then added a mixture of 332 mg of chloroacetone and 2 ml of DMF. The mixture was then stirred for 8 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane). As a result, 487 mg of 2-[(4-chlorophenyl)imino]-2,3-dihydro-3-(2-oxopropyl)-4H-pyrido[3,2-e]-1,3-thiazin-4-one was obtained as a low polarity substance, and 267 mg of 2-[N-(4-chlorophenyl)-N-(2-oxopropyl)amino]-4H-pyrido[3,2-e]-1,3-thiazin-4-one was obtained as a high polarity substance. 1) 2-[(4-Chlorophenyl)imino]-2,3-dihydro-3-(2-oxopropyl)-4H-pyrido[3,2-e]-1,3-thiazin-4-one Melting point: 160–161° C.

Nuclear magnetic resonance spectrum (DMSO-$d_6$, TMS internal standard) δ: 2.25 (3H, s), 5.14 (2H, s), 6.88 (2H, d, J=8.4 Hz), 7.46 (2H, d, J=8.4 Hz), 7.54 (1H, dd, J=4.8, 8.0 Hz), 8.50 (1H, dd, J=1.6, 8.0 Hz), 8.74 (1H, dd, J=1.6, 4.8 Hz)

2) 2-[N-(4-Chlorophenyl)-N-(2-oxopropyl)amino]-4H-pyrido[3,2-e]-1,3-thiazin-4-one Melting point: 197° C.

Nuclear magnetic resonance spectrum (DMSO-$d_6$, TMS internal standard) δ: 2.20 (3H, s), 4.91 (2H, s), 7.57 (2H, d, J=8.8 Hz), 7.59 (1H, dd, J=4.4, 8.0 Hz), 7.68 (2H, d, J=8.8 Hz), 8.50 (1H, dd, J=2.0, 8.0 Hz), 8.71 (1H, dd, J=2.0, 4.4 Hz)

EXAMPLE 127

Ethyl 2-[2-[(4-chlorophenyl)imino]-2,3-dihydro-4-oxo-4H-pyrido[3,2-e]-1,3-thiazin-3-yl]acetate and ethyl 2-[N-(4-chlorophenyl)-N-(4-oxo-4H-pyrido[3,2-e]-1,3-thiazin-2-yl)amino]acetate In an atmosphere of argon, a mixture of 32 mg (4.0 mmol) of lithium hydride and 7 ml of DMF was put in a 100 ml flask. To the flask was then connected a dropping funnel which contained 1.0 g (3.5 mmol) of 2-(4-chloroanilino)-4H-pyrido[3,2-e]-1,3-thiazin-4-one and 12 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 20 minutes. To the mixture was then added a mixture of 605 mg of ethyl bromoacetate and 4 ml of DMF. The mixture was then stirred for 11 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane). As a result, 830 mg of ethyl 2-[2-[(4-chlorophenyl)imino]-2,3-dihydro-4-oxo-4H-pyrido[3,2-e]-1,3-thiazin-3-yl]acetate was obtained as a low polarity substance, and 350 mg of ethyl 2-[N-(4-chlorophenyl)-N-(4-oxo-4H-pyrido[3,2-e]-1,3-thiazin-2-yl)amino]acetate was obtained as a high polarity substance.

1) Ethyl 2-[2-[(4-chlorophenyl)imino]-2,3-dihydro-4-oxo-4H-pyrido[3,2-e]-1,3-thiazin-3-yl]acetate Melting point: 131–133° C.

Nuclear magnetic resonance spectrum (DMSO-$d_6$, TMS internal standard) δ: 1.21 (3H, t, J=7.2 Hz), 4.19 (2H, q, J=7.2 Hz), 5.01 (2H, s), 6.90 (2H, d, J=8.8 Hz), 7.48 (2H, d, J=8.8 Hz), 7.55 (1H, dd, J=4.8, 8.0 Hz), 8.53 (1H, dd, J=2.0, 8.0 Hz), 8.75 (1H, dd, J=2.0, 4.8 Hz)

2) Ethyl 2-[N-(4-chlorophenyl)-N-(4-oxo-4H-pyrido[3,2-e]-1,3-thiazin-2-yl)amino]acetate Melting point: 178–179° C.

Nuclear magnetic resonance spectrum (DMSO-$d_6$, TMS internal standard) δ: 1.22 (3H, t, J=7.2 Hz), 4.18 (2H, q, J=7.2 Hz), 4.77 (2H, s), 7.60 (1H, dd, J=4.8, 8.0 Hz), 7.63 (2H, d, J=8.8 Hz), 7.70 (2H, d, J=8.8 Hz), 8.52 (1H, dd, J=1.6, 8.0 Hz), 8.72 (1H, dd, J=1.6, 4.8 Hz)

EXAMPLE 128

2-[2-[(4-Chlorophenyl)imino-4-oxo-2,3-dihydro-4H-pyrido[3,2-e]-1,3-thiazin-3-yl]acetamide and 2-[N-(4-chlorophenyl)-N-(4-oxo-4H-pyrido[3,2-e]-1,3-thiazin-2-yl)amino]acetamide In an atmosphere of argon, a mixture of 34 mg (4.3 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 5 ml of DMF. The solution of 2-(4-chloroanilino)-4H-pyrido[3,2-e]-1,3-thiazin-4-one was then added dropwise to the aforementioned mixture with stirring in 4 minutes. The mixture was further stirred for 40 minutes. To the mixture was then added a mixture of 571 mg of 2-bromoacetamide and 2 ml of DMF. The mixture was then stirred for 23 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 3/1 mixture of ethyl acetate and normal hexane). As a result, 144 mg of 2-[2-[(4-chlorophenyl)imino-4-oxo-2,3-dihydro-4H-pyrido[3,2-e]-1,3-thiazin-3-yl]acetamide was obtained as a low polarity substance, and 67 mg of 2-[N-(4-chlorophenyl)-N-(4-oxo-4H-pyrido[3,2-e]-1,3-thiazin-2-yl)amino]acetamide was obtained as a high polarity substance.

1) 2-[2-[(4-Chlorophenyl)imino-4-oxo-2,3-dihydro-4H-1:5 pyrido[3,2-e]-1,3-thiazin-3-yl]acetamide Melting point: 213–215° C.

Nuclear magnetic resonance spectrum (DMSO-$d_6$, TMS internal standard) δ: 4.80 (2H, s), 6.88 (2H, d, J=8.4 Hz), 7.15 (1H, bs), 7.47 (2H, d, J=8.4 Hz), 7.53 (1H, dd, J=4.8, 7.6 Hz), 7.65 (1H, bs), 8.51 (1H, dd, J=1.6, 7.6 Hz), 8.72 (1H, dd, J=1.6, 4.8 Hz)

2) 2-[N-(4-Chlorophenyl)-N-(4-oxo-4H-pyrido[3,2-e]-1,3-thiazin-2-yl)amino]acetamide Melting point: 249–251° C.

Nuclear magnetic resonance spectrum (DMSO-$d_6$, TMS internal standard) δ: 4.58 (2H, bs), 6.88 (2H, d, J=8.8 Hz), 7.25 (1H, bs), 7.47 (2H, d, J=8.8 Hz), 7.58 (1H, d, J=4.8, 7.6 Hz), 7.68 (1H, bs), 8.51 (1H, dd, J=2.0, 7.6 Hz), 8.70 (1H, dd, J=2.0, 4.8 Hz)

EXAMPLE 129

[2-[(4-Chlorophenyl)imino]-2,3-dihydro-4-oxo-4H-pyrido[3,2-e]-1,3-thiazin-3-yl]acetonitrile and 2-[N-(4-chlorophenyl)-N-(4-oxo-4H-pyrido[3,2-e]-1,3-thiazin-2-yl)amino]acetonitrile In an atmosphere of argon, a mixture of 26 mg (3.3 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 3 minutes. The mixture was further stirred for 1 hour. To the mixture was then added a mixture of 313 mg of chloroacetonitrile and 1 ml of DMF. The mixture was then stirred for 3 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane). As a result, 805 mg of [2-[(4-chlorophenyl)imino]-2,3-dihydro-4-oxo-4H-pyrido[3,2-e]-1,3-thiazin-3-yl]acetonitrile was obtained as a low polarity substance, and 70 mg of 2-[N-(4-chlorophenyl)-N-(4-oxo-4H-pyrido[3,2-e]-1,3-thiazin-2-yl)amino]acetonitrile was obtained as a high polarity substance.

1) [2-[(4-Chlorophenyl)imino]-2,3-dihydro-4-oxo-4H-pyrido[3,2-e]-1,3-thiazin-3-yl]acetonitrile Melting point: 146° C.

Nuclear magnetic resonance spectrum (DMSO-$d_6$, TMS internal standard) δ: 5.22 (2H, s), 7.00 (2H, d, J=8.8 Hz), 7.51 (2H, d, J=8.8 Hz), 7.55 (1H, dd, J=4.8, 8.0 Hz), 8.54 (1H, dd, J=1.6, 8.0 Hz), 8.74 (1H, dd, J=1.6, 4.8 Hz)

2) 2-[N-(4-chlorophenyl)-N-(4-oxo-4H-pyrido[3,2-e]-1,3-thiazin-2-yl)amino]acetonitrile Melting point: 209–210° C.

Nuclear magnetic resonance spectrum (DMSO-$d_6$, TMS internal standard) δ: 5.16 (2H, s), 7.62 (1H, dd, J=4.4, 8.0 Hz), 7.67 (2H, d, J=8.8 Hz), 7.76 (2H, d, J=8.8 Hz), 8.56 (1H, dd, J=1.6, 8.0 Hz), 8.74 (1H, dd, J=1.6, 4.4 Hz)

EXAMPLE 130

[2-[(4-Chlorophenyl)imino]-2,3-dihydro-3-(1H-tetrazol-5-ylmethyl)-4H-pyrido[3,2-e]-1,3-thiazin-4-one A mixture of 658 mg (2 mmol) of [2-[(4-chlorophenyl)imino]-2,3-dihydro-4-oxo-4H-pyrido[3,2-e]-1,3-thiazin-3-yl]acetonitrile and 8 ml of DMF was put in a 50 ml flask. To the mixture were then added 1.30 g of sodium azide and 1.07 g of ammonium chloride with stirring. The mixture was then stirred at a temperature of 120° C. for 4 hours. The resulting reaction mixture was allowed to cool, poured into water, and then extracted with ethyl acetate. The resulting organic phase was separated, washed with water and saturated brine, and then dried over sodium sulfate. The drying agent was then removed by filtration. The filtrate was then concentrated under reduced pressure. The resulting residue was then washed with cold ethanol to obtain 512 mg of 2,3-dihydro-[2-((4-chlorophenyl)imino]-3-(1H-tetrazol-5-ylmethyl)-4H-pyrido[3,2-e]-1,3-thiazin-4-one.

Nuclear magnetic resonance spectrum (DMSO-$d_6$, TMS internal standard) δ: 5.74 (2H, s), 6.83 (2H, d, J=8.8 Hz), 7.46 (2H, d, J=8.8 Hz), 7.56 (1H, dd, J=4.8, 8.0 Hz), 8.54 (1H, dd, J=1.6, 8.0 Hz), 8.76 (1H, dd, J=1.6, 4.8 Hz)

Mass spectrum (m/z): 372.4 ($M^+$)

EXAMPLE 131

2-[N-(4-Chlorophenyl)-N-(1H-tetrazol-5-ylmethyl)amino]-4H-pyrido[3,2-e]-1,3-thiazin-4-one A mixture of 74 mg (0.23 mmol) of 2-[N-(4-chlorophenyl)-N-(4-oxo-4H-pyrido[3,2-e]-1,3-thiazin-2-yl]amino]acetonitrile and 1 ml of DMF was put in a 20 ml flask. To the mixture were then added 146 mg of sodium azide and 120 mg of ammonium chloride with stirring. The mixture was then stirred at a temperature of 120° C. for 4 hours. The resulting reaction mixture was allowed to cool, poured into water, and then extracted with ethyl acetate. The resulting organic phase was separated, washed with water and saturated brine, and then dried over sodium sulfate. The drying agent was then removed by filtration. The filtrate was then concentrated under reduced pressure. The resulting residue was then washed with cold ethanol to obtain 30 mg of 2-[N-(4-chlorophenyl)-N-(1H-tetrazol-5-ylmethyl)amino]-4H-pyrido[3,2-e]-1,3-thiazin-4-one.

Melting point: 258–259° C.

Nuclear magnetic resonance spectrum (DMSO-$d_6$, TMS internal standard) δ: 5.53 (2H, bs), 7.60 (1H, dd, J=4.8, 8.0 Hz), 7.67 (4H, m), 8.51 (1H, dd, J=1.6, 8.0 Hz), 8.72 (1H, dd, J=1.6, 4.8 Hz)

EXAMPLE 132

[2-[(4-Chlorophenyl)imino]-2,3-dihydro-3-(3-pyridylmethyl)]-4H-pyrido[3,2-e]-1,3-thiazin-4-one and 2-[N-(4-chlorophenyl)-N-(3-pyridylmethyl)amino]-4H-pyrido[3,2-e]-1,3-thiazin-4-one In an atmosphere of argon, a mixture of 76 mg (9.6 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 75 minutes. To the mixture was then added a mixture of 680 mg of 3-(chloromethyl)pyridine hydrochloride and 5 ml of DMF. The mixture was then stirred for 92 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/3 to 5/1 mixture of ethyl acetate and normal hexane). As a result, 690 mg of [2-[(4-chlorophenyl)imino]-2,3-dihydro-3-(3-pyridylmethyl)]-4H-pyrido[3,2-e]-1,3-thiazin-4-one was obtained as a low polarity substance, and 141 mg of 2-[N-(4-chlorophenyl)-N-(3-pyridylmethyl)amino]-4H-pyrido[3,2-e]-1,3-thiazin-4-one was obtained as a high polarity substance.

1) [2-[(4-Chlorophenyl)imino]-2,3-dihydro-3-(3-pyridylmethyl)]-4H-pyrido[3,2-e]-1,3-thiazin-4-one Melting point: 132–133° C.

Nuclear magnetic resonance spectrum (DMSO-$d_6$, TMS internal standard) δ: 5.50 (2H, s), 6.90 (2H, d, J=8.8 Hz), 7.36 (2H, dd, J=4.8, 8.0 Hz), 7.46 (2H, d, J=8.8 Hz), 7.52 (1H, dd, J=4.8, 8.0 Hz), 7.85 (1H, dt, J=1.6, 8.0 Hz), 8.48 (1H, dd, J=1.6, 4.8 Hz), 8.51 (1H, dd, J=2.0, 8.0 Hz), 8.67 (1H, d, J=1.6 Hz), 8.71 (1H, dd, J=2.0, 4.8 Hz)

2) 2-[N-(4-Chlorophenyl)-N-(3-pyridylmethyl)amino]-4H-pyrido[3,2-e]-1,3-thiazin-4-one Melting point: 220–221° C.

Nuclear magnetic resonance spectrum (DMSO-$d_6$, TMS internal standard) δ: 5.33 (2H, s), 7.35 (1H, dd, J=4.8, 8.0 Hz), 7.46 (2H, d, J=8.8 Hz), 7.59 (1H, dd, J=4.8, 8.0 Hz), 7.62 (2H, d, J=8.8 Hz), 7.78 (1H, dt, J=2.0, 8.0 Hz), 8.49 (1H, dd, J=2.0, 4.8 Hz), 8.51 (1H, d, J=2.0 Hz), 8.54 (1H, dd, J=1.6, 8.0 Hz), 8.71 (1H, dd, J=1.6, 4.8 Hz)

EXAMPLE 133

2-[(4-Chlorophenyl)imino]-3-(2,3-dihydropropyl)-2,3-dihydro-4H-pyrido[3,2-e]-1,3-thiazin-4-one In an atmosphere of argon, a mixture of 31 mg (3.9 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 45 minutes. To the mixture was then added a mixture of 642 mg of 3-bromo-1,2-propanediol and 2 ml of DMF. The mixture was then stirred for 23 hours. After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane) to obtain 467 mg of 2-[(4-chlorophenyl)imino]-2,3-dihydro-3-(2,3-dihydropropyl)-4-pyrido[3,2-e]-1,3-thiazin-4-one.

Melting point: 123–125° C.

Nuclear magnetic resonance spectrum (DMSO-$d_6$, TMS internal standard) δ: 3.42 (2H, dd, J=5.6, 5.6 Hz), 4.02 (1H, m), 4.25 (1H, dd, J=4.8, 13.2 Hz), 4.49 (1H, dd, J=8.0, 13.2 Hz), 4.58 (1H, t, J=5.6 Hz), 4.84 (1H, d, J=5.2 Hz), 6.93 (2H, d, J=8.4 Hz), 7.48 (2H, d, J=8.4 Hz), 7.50 (1H, dd, J=4.8, 8.0 Hz), 8.49 (1H, dd, J=1.6, 8.0 Hz), 8.69 (1H, dd, J=1.6, 4.8 Hz)

EXAMPLE 134

Ethyl 4-[2-((4-chlorophenyl)imino)-4-oxo-2,3-dihydro-4H-pyrido[3,2-e]-1,3-thiazin-3-yl]butanoate The reaction and processing procedure of Example 127 was followed except that 34 mg (4.3 mmol) of lithium hydride, 16 ml of DMF, 800 mg (2.8 mmol) of 2-(4-chloroanilino)-4H-pyrido[3,2-e]-1,3-thiazin-4-one and 833 mg of ethyl ester 4-bromobutyrate were used and post-treatment was carried out. The resulting residue was then purified through silica gel column chromatography (eluant: 1/3 mixture of ethyl acetate and normal hexane) to obtain 1.19 g of ethyl 4-[2-(4 -chlorophenyl)imino)-4-oxo-2,3-dihydro-4H-pyrido[3,2-e]-1,3-thiazin-3-yl]butanoate.

Nuclear magnetic resonance spectrum (DMSO-$d_6$, TMS internal standard) δ: 1.10 (3H, t, J=7.2 Hz), 2.01 (2H, m), 2.42 (2H, t, J=7.2 Hz), 3.97 (2H, q, J=7.2 Hz), 4.33 (2H, t, J=6.8 Hz), 6.95 (2H, d, J=8.8 Hz), 7.48 (2H, d, J=8.8 Hz), 7.50 (1H, dd, J=4.8, 8.4 Hz), 8.49 (1H, dd, J=2.0, 8.4 Hz), 8.69 (1H, dd, J=2.0, 4.8 Hz)

Elementary analysis (for $C_{19}H_{18}ClN_3O_3S$):

|        | C (%) | H (%) | N (%) | S (%) | Cl (%) |
|--------|-------|-------|-------|-------|--------|
| Calcd.: | 56.50 | 4.49 | 10.40 | 7.94 | 8.78 |
| Found: | 56.19 | 4.48 | 10.32 | 7.99 | 8.71 |

EXAMPLE 135

2-[2-[2-((4-Chlorophenyl)imino]-4-oxo-2,3-dihydro-4H-pyrido[3,2-e]-1,3-thiazin-3-yl]ethyl]isoindol-1,3-dione The reaction and processing procedure of Example 127 was followed except that 30 mg (3.8 mmol) of lithium hydride, 17 ml of DMF, 800 mg (2.8 mmol) of 2-(4-chloroanilino)-4H-pyrido[3,2-e]-1,3-thiazin-4-one and 1.12 g of N-(2-bromoethyl)-phthalimide were used and post-treatment was carried out. The resulting residue was then purified through silica gel column chromatography (eluant: 1/2 mixture of ethyl acetate and normal hexane) to obtain 883 mg of 2-[2-[2-(4-chlorophenyl)imino]-4-oxo-2,3-dihydro-4H-pyrido[3,2-e]-1,3-thiazin-3-yl]ethyl]isoindol-1,3-dione.

Melting point: 183–184° C.

Nuclear magnetic resonance spectrum (DMSO-$d_6$, TMS internal standard) δ: 4.08 (2H, t, J=5.2 Hz), 4.59 (2H, t, J=5.2 Hz), 6.44 (2H, d, J=8.4 Hz), 7.32 (2H, d, J=8.4 Hz), 7.48 (1H, dd, J=4.8, 8.0 Hz), 7.84 (4H, s), 8.41 (1H, dd, J=1.6, 8.0 Hz), 8.69 (1H, dd, J=1.6, 4.8 Hz)

EXAMPLE 136

2-[(4-Chlorophenyl)imino]-3-([1,3]dioxolan-2-ylmethyl)-2,3-dihydro-4H-pyrido[3,2-e]-1,3-thiazin-4-one and 2-[N-(4-chlorophenyl)-N-([1,3]dioxolan-2-ylmethyl)amino]-4H-pyrido[3,2-e]-1,3-thiazin-4-one In an atmosphere of argon, a mixture of 290 mg (1.0 mmol) of 2-(4-chloroanilino)-4H-pyrido[3,2-e]-1,3-thiazin-4-one and 1.4 ml of DMSO was put in a 30 ml flask. To the mixture was then added 113 mg (1.0 mmol) of potassium t-butoxide with stirring. The mixture was then stirred for 1 hour. To the mixture was then added 10 mg (0.06 eq) of potassium iodide. To the mixture was then added 484 mg of 2-bromomethyl-1,3-dioxolane. The mixture was then stirred for 15 hours. After the termination of reaction, the reaction mixture was extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/2 mixture of ethyl acetate and normal hexane). As a result, 36 mg of 2-[(4-chlorophenyl)imino]-3-([1,3]dioxolan-2-ylmethyl)-2,3-dihydro-4H-pyrido[3,2-e]-1,3-thiazin-4-one was obtained as a low polarity substance, and 20 mg of 2-[N-(4-chlorophenyl)-N-([1,3]dioxolan-2-ylmethyl)amino]-4H-pyrido[3,2-e]-1,3-thiazin-4-one was obtained as a high polarity substance.

1) 2-[(4-Chlorophenyl)imino]-3-([1,3]dioxolan-2-ylmethyl)-2,3-dihydro-4H-pyrido[3,2-e]-1,3-thiazin-4-one Melting point: 121–122° C.

Nuclear magnetic resonance spectrum (DMSO-$d_6$, TMS internal standard) δ: 3.85 (2H, m), 3.97 (2H, m), 4.44 (2H, d, J=5.2 Hz), 5.40 (1H, t, J=5.2 Hz), 6.96 (2H, d, J=8.8 Hz), 7.48 (2H, d, J=8.8 Hz), 7.52 (1H, dd, J=4.8, 8.0 Hz), 8.51 (1H, dd, J=1.6, 8.0 Hz), 8.71 (1H, dd, J=1.6, 4.8 Hz)

2) 2-[N-(4-Chlorophenyl)-N-([1,3]dioxolan-2-ylmethyl)amino]-4H-pyrido[3,2-e]-1,3-thiazin-4-one Nuclear magnetic resonance spectrum (DMSO-$d_6$, TMS internal standard) δ: 3.81 (2H, m), 3.87 (2H, m), 4.14 (2H, d, J=4.4 Hz), 5.27 (1H, t, J=4.4 Hz), 7.57 (1H, dd, J=4.8, 8.0 Hz), 7.60 (2H, d, J=8.4 Hz), 7.68 (2H, d, J=8.4 Hz), 8.51 (1H, dd, J=1.6, 8.0 Hz), 8.69 (1H, dd, J=1.6, 4.8 Hz)

Mass spectrum (m/z): 376 ($M^+$+1)

EXAMPLE 137

[2-[(4-Chlorophenyl)imino]-4-oxo-2,3-dihydro-4H-pyrido[3,2-e]-1,3-thiazin-3-yl]acetic acid A mixture of 99 mg (0.3 mmol) of ethyl 2-[(4-chlorophenyl)imino)-4-oxo-2,3-dihydro-4H-pyrido[3,2-e]-1,3-thiazin-3-yl]acetate and 1 ml of ethanol was put in a 50 ml flask. To the mixture was then added a mixture of 52 mg of potassium hydroxide and 2 ml of ethanol with stirring. The mixture was then stirred at a temperature of 100° C. for 2 hours. After the termination of reaction, the mixture was concentrated under reduced pressure. To the resulting residue was then added water. The residue was then washed with ethyl acetate. The resulting aqueous phase was acidified with a 2 N hydrochloric acid, and then extracted with ethyl acetate. The resulting organic phase was separated, washed with water and saturated brine, and then dried over sodium sulfate. The drying agent was then removed by filtration. The filtrate was then concentrated under reduced pressure. The resulting residue was then washed with cold ethanol to obtain 90 mg of 2-[(4-chlorophenyl)imino]-4-oxo-2,3-dihydro-4H-pyrido[3,2-e]-1,3-thiazin-3-yl)acetic acid.

Mass spectrum (m/z): 348 ($M^+$+1)

Elementary analysis (for $C_{15}H_{10}ClN_3O_3S$):

|        | C (%) | H (%) | N (%) | S (%) | Cl (%) |
|--------|-------|-------|-------|-------|--------|
| Calcd.: | 51.80 | 2.90 | 12.08 | 9.22 | 10.19 |
| Found: | 52.16 | 2.93 | 11.86 | 9.42 | 10.18 |

EXAMPLE 138

4-Chloro-N-(4-oxo-4H-pyrido[3,2-e]-1,3-thiazin-2-yl)acetanilide

A mixture of 1.826 g (6.30 mmol) of 2-(4-chloroanilino)-4H-pyrido[3,2-e]-1,3-thiazin-4-one and 30 ml of pyridine was stirred over a 60° C. oil bath for 30 minutes to make a solution. To the solution was then added dropwise 1.3 g of acetic anhydride at the same temperature with stirring in 5 minutes. The mixture was then further stirred overnight. The reaction mixture was allowed to cool to room temperature, and then poured into about 1,000 ml of ice-water. The resulting crystal was collected by filtration, washed with water, and then dried under reduced pressure. The resulting crude product was then recrystallized from a mixture of dioxane and diisopropyl ether to obtain 991 mg of 4-chloro-N-(4-oxo-4H-pyrido[3,2-e]-1,3-thiazin-2-yl)acetanilide.

Melting point: 223.5–224.5° C. (decomposition)

Nuclear magnetic resonance spectrum (CDCl$_3$, TMS internal standard) δ: 2.20 (3H, s), 7.22 (2H, d. J=8.8 Hz), 7.49 (1H, dd, J=4.4, 8.0 Hz), 7.51 (2H, d, J=8.8 Hz), 8.59 (1H, dd, J=1.6, 8.0 Hz), 8.77 (1H, dd, J=1.6, 4.8 Hz)

EXAMPLE 139

N-(4-Chlorophenyl)-N-(4-oxo-4H-pyrido[3,2-e]-1,3-thiazin-2-yl)-3-aminopropionitrile The reaction procedure of Example 57 was followed except that 1.00 g of 2-chloronicotinic acid, 5 ml of thionyl chloride, two droplets of DMF, 10 ml of acetone, 1.15 g of N-(4-chlorophenyl)-3-aminopropionitrile and 10 ml of acetone were used. The resulting crude product was then recrystallized from ethanol to obtain 1.38 g of N-(4-chlorophenyl)-N-(4-oxo-4H-pyrido[3,2-e]-1,3-thiazin-2-yl)-3-aminopropionitrile.

Melting point: 177–178° C.

Elementary analysis (for $C_{16}H_{11}N_4OSCl$):

|          | C (%) | H (%) | N (%) | S (%) | Cl (%) |
|----------|-------|-------|-------|-------|--------|
| Calcd.:  | 56.06 | 3.23  | 16.34 | 9.35  | 10.34  |
| Found:   | 56.00 | 3.20  | 16.18 | 9.25  | 10.42  |

EXAMPLE 140

N-(4-Chlorophenyl)-N-(4-oxo-4H-pyrido[3,2-e]-1,3-thiazin-2-yl)-4-aminobutyronitrile The reaction procedure of Example 57 was followed except that 2.35 g of 2-chloronicotinic acid, 5 ml of thionyl chloride, two droplets of DMF, 15 ml of acetone, 2.90 g of N-(4-chlorophenyl)-4-aminobutyronitrile and 15 ml of acetone were used. The resulting crude product was then recrystallized from ethanol to obtain 2.05 g of N-(4-chlorophenyl)-N-(4-oxo-4H-pyrido[3,2-e]-1,3-thiazin-2-yl)-4-aminobutyronitrile.

Nuclear magnetic resonance spectrum (CDCl$_3$, TMS internal standard) δ: 1.88–1.95 (2H, m), 2.65 (2H, t, J=6.8 Hz), 4.10 (2H, t, J=7.2 Hz), 7.51–7.59 (1H, m), 7.66 (2H, d, J=6.4 Hz), 7.71 (2H, d, J=6.4 Hz), 8.51 (1H, dd, J=1.6, 8.0 Hz), 8.69 (1H, dd, J=2.4, 4.8 Hz)

Melting point: 139–140° C.

EXAMPLE 141

N-(4-Chlorophenyl)-N-(4-oxo-4H-pyrido[3,2-e]-1,3-thiazin-2-yl)-5-aminovaleronitrile The reaction procedure of Example 57 was followed except that 1.92 g of 2-chloronicotinic acid, 5 ml of thionyl chloride, two droplets of DMF, 15 ml of acetone, 1.92 g of N-(4-chlorophenyl)-5-aminovaleronitrile and 15 ml of acetone were used. The product was then recrystallized from ethanol to obtain 0.85 g of N-(4-chlorophenyl)-N-(4-oxo-4H-pyrido[3,2-e]-1,3-thiazin-2-yl)-5-aminovaleronitrile.

Melting point: 134–135° C.

Elementary analysis (for $C_{18}H_{15}N_4OSCl$):

|          | C (%) | H (%) | N (%) | S (%) | Cl (%) |
|----------|-------|-------|-------|-------|--------|
| Calcd.:  | 58.30 | 4.08  | 15.11 | 8.65  | 9.56   |
| Found:   | 58.06 | 4.04  | 15.08 | 8.58  | 9.68   |

EXAMPLE 142

2,3-Dihydro-2-[(4-chlorophenyl)imino]-3-(5-hydroxypentyl)-4H-pyrido[3,2-e]-1,3-thiazin-4-one In an atmosphere of argon, a mixture of 35 mg (4.4 mmol) of lithium hydride and 5 ml of DMF was put in a 100 ml flask. To the flask was then connected a dropping funnel which contained 800 mg (2.8 mmol) of 2-(4-chloroanilino)-4H-pyrido[3,2-e]-1,3-thiazin-4-one and 10 ml of DMF. The solution of 2-(4-chloroanilino)-4H-pyrido[3,2-e]-1,3-thiazin-4-one was then added dropwise to the aforementioned mixture with stirring in 5 minutes. The mixture was further stirred for 1.5 hours. To the mixture was then added a mixture of 508 mg of 5-chloro-1-pentanol and 4 ml of DMF. The mixture was then stirred for 158 hours.

After the termination of reaction, the mixture was concentrated under reduced pressure. The resulting residue was then extracted with water and ethyl acetate. The resulting organic phase was separated, washed with water and saturated brine, and then dried over sodium sulfate. The drying agent was then removed by filtration. The filtrate was then concentrated under reduced pressure. The resulting residue was then purified through silica gel column chromatography (eluant: 1/1 mixture of ethyl acetate and normal hexane) to obtain 156 mg of 2,3-dihydro-2-[(4-chlorophenyl)imino]-3-(5-hydroxypentyl)-4H-pyrido[3,2-e]-1,3-thiazin-4-one.

Nuclear magnetic resonance spectrum (DMSO-d$_6$, TMS internal standard) δ: 1.38 (2H, m), 1.48 (2H, m), 1.73 (2H, qunit, J=7.2 Hz), 3.40 (2H, q, J=6.0 Hz), 4.26 (2H, t, J=7.6 Hz), 4.35 (1H, t, J=4.8 Hz), 6.95 (2H, d, J=8.8 Hz), 7.47 (2H, d, J=8.8 Hz), 7.50 (1H, dd, J=4.8, 8.0 Hz), 8.49 (1H, dd, J=1.6, 8.0 Hz), 8.69 (1H, dd, J=1.6, 4.8 Hz)

Mass spectrum (m/z): 376 (M$^+$+1)

EXAMPLE 143

2-[N-(Benzo[b]thiophen-2-yl)-N-methylamino]-4H-pyrido[3,2-e]-1,3-thiazin-4-one The reaction procedure of Example 102 was followed except that 278 mg of 2-chloronicotinoyl chloride, 120 mg of ammonium thiocyanate, 258 mg of -2-(methylamino) benzo[b]thiophene and 6 ml of acetone were used. The product was then recrystallized from a mixture of ethanol and ethyl acetate to obtain 143 mg of 2-[N-(benzo[b] thiophen-2-yl)-N-methylamino]-4H-pyrido[3,2-e]-1,3-thiazin-4-one.

Melting point: 220–221° C.

Elementary analysis (for $C_{16}H_{11}N_3OS_2$):

|  | C (%) | H (%) | N (%) | S (%) |
|---|---|---|---|---|
| Calcd.: | 59.06 | 3.41 | 12.91 | 19.71 |
| Found: | 58.82 | 3.36 | 12.75 | 19.64 |

The chemical structural formula of the compounds obtained in the aforementioned examples will be given in the tables below. The symbols used hereinafter have the following respective meanings:

Me: a methyl group, Et: an ethyl group, Pr: a propyl group, Bu: a butyl group, Ac: an acetyl group, Ph: a phenyl group, Bn: a benzyl group

TABLE 3

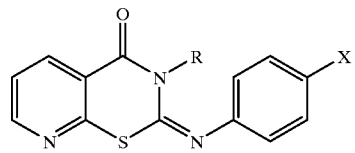

| Example | R | X | Example | R | X |
|---|---|---|---|---|---|
| 1 | H | Me | 2 | H | Cl |
| 3 | H | Br | 4 | H | I |
| 5 | H | H | 6 | H | $NO_2$ |
| 7 | H | CN | 8 | H | OMe |
| 9 | H | $CF_3$ | 10 | H | COOEt |
| 11-1) | n-Pr | Me | 12-1) | i-Pr | Me |
| 13-1) | n-Bu | Me | 14-1) | $CH_2CH=CH_2$ | Me |
| 15-1) | Bn | Me | 16-1) | Me | Br |
| 17-1) | n-Pr | Br | 18-1) | Bn | Br |
| 19-1) | Et | Cl | 20-1) | n-Pr | Cl |
| 21-1) | Bn | Cl | 22-1) | n-Pr | I |
| 23-1) | n-Pr | CN | 24-1) | Bn | CN |
| 25-1) | Me | OMe | 26-1) | Et | OMe |
| 27-1) | n-Pr | OMe | 28-1) | i-Pr | OMe |
| 29-1) | n-Bu | OMe | 30-1) | $CH_2CH=CH_2$ | OMe |
| 31-1) | Bn | OMe | 32-1) | $(CH_2)_2NEt_2$ | OMe |
| 33-1) | Me | $CF_3$ | 34-1) | Bn | COOEt |
| 35 | Me | Me | 36 | Et | Me |
| 37 | Me | Cl | 38 | Me | I |
| 39 | Me | CN | 40 | Me | $NO_2$ |
| 41 | n-Pr | $NO_2$ | 42 | Bn | $NO_2$ |
| 43 | Bn | I | 44 | Me | H |
| 45 | Et | H | 46 | n-Pr | H |
| 47 | i-Pr | H | 48 | n-Bu | H |
| 49 | $CH_2CH=CH_2$ | H | 50 | Bn | H |
| 51 | $(CH_2)_2NEt_2$ | Me | 52 | $(CH_2)_2NEt_2$ | H |
| 53 | n-Pr | $CF_3$ | 54 | Bn | $CF_3$ |
| 55 | Me | COOEt | 56 | n-Pr | COOEt |
| 103-1) | $CH_2$-(3-OCH$_3$-phenyl) | Cl | 104-1) | $CH_2$-(5-Cl-thiophen-2-yl) | Cl |
| 105-1) | $CH_2C\equiv CH$ | Cl | 123-1) | $CH_2CH_2OH$ | Cl |

TABLE 4

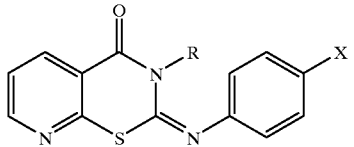

| Example | R | X | Example | R | X |
|---|---|---|---|---|---|
| 124-1) | CH₂CH₂OMe | Cl | 125-1) | CH₂CH₂OC(O)CH₃ | Cl |
| 126-1) | CH₂C(O)CH₃ | Cl | 127-1) | CH₂C(O)OEt | Cl |
| 128-1) | CH₂C(O)NH₂ | Cl | 129-1) | CH₂CN | Cl |
| 130 | CH₂-(1H-tetrazol-5-yl) | Cl | 132-1) | CH₂-(3-pyridyl) | Cl |
| 133 | CH₂CH(OH)CH₂OH | Cl | 134 | CH₂CH₂CH₂C(O)OEt | Cl |
| 135 | CH₂CH₂-phthalimido | Cl | 136-1) | CH₂-(1,3-dioxolan-2-yl) | Cl |
| 137 | CH₂COOH | Cl | 142 | CH₂(CH₂)₄OH | Cl |

TABLE 5

| Example | R | X | Example | R | X |
|---|---|---|---|---|---|
| 11-2) | n-Pr | p-Me | 12-2) | i-Pr | p-Me |
| 13-2) | n-Bu | p-Me | 14-2) | allyl | p-Me |
| 15-2) | Bn | p-Me | 16-2) | Me | p-Br |
| 17-2) | n-Pr | p-Br | 18-2) | Bn | p-Br |
| 19-2) | Et | p-Cl | 20-2) | n-Pr | p-Cl |

TABLE 5-continued

| Example | R | X | Example | R | X |
|---|---|---|---|---|---|
| 21-2) | Bn | p-Cl | 22-2) | n-Pr | p-I |
| 23-2) | n-Pr | p-CN | 24-2) | Bn | p-CN |
| 25-2) | Me | p-OMe | 26-2) | Et | p-OMe |
| 27-2) | n-Pr | p-OMe | 28-2) | i-Pr | p-OMe |

TABLE 6
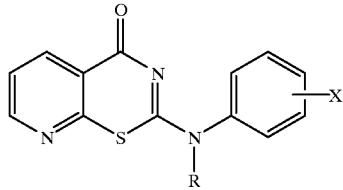
| Example | R | X | Example | R | X |
| --- | --- | --- | --- | --- | --- |
| 29-2) | n-Bu | p-OMe | 30-2) | CH₂CH=CH₂ | p-OMe |
| 31-2) | Bn | p-OMe | 32-2) | (CH₂)₂NEt₂ | p-OMe |
| 33-2) | Me | p-CF₃ | 34-2) | Bn | p-COOEt |
| 57 | Et | p-Me | 58 | Me | H |
| 59 | n-Pr | H | 60 | i-Pr | H |
| 61 | Bn | H | 62 | Et | p-Br |
| 63 | Me | p-NO₂ | 64 | Me | p-Cl |
| 65 | n-Pr | p-CF₃ | 66 | Bn | p-CF₃ |
| 67 | Me | p-COOEt | 68 | n-Pr | p-COOEt |
| 72 | Me | m-Me | 73 | Me | o-Me |
| 75 | Me | p-OCF₃ | 87 | Et | m-OMe |
| 88 | Et | p-i-Pr | 89 | Et | p-Ac |
| 93 | Me | p-NHOH | 94 | Me | p-NH₂ |
| 98 | CH₂CH₂OH | H | 102 | Me | p-F |
| 103-2) | 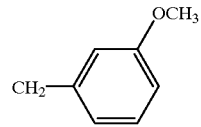 | p-Cl | 104-2) | 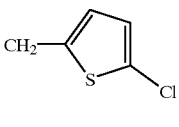 | p-Cl |
| 105-2) | CH₂C≡CH | p-Cl | 112 | Me |  |
| 113 | Me | p-Ph | 114 | Me | p-CH₂CN |
| 115 | Me |  | 116 | Me | p-CH₂COOH |
| 117 | Me | p-COOH | 123-2) | CH₂CH₂OH | p-Cl |
| 124-2) | CH₂CH₂OMe | p-Cl | 125-2) | 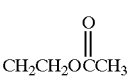 | p-Cl |
| 126-2) |  | p-Cl | 127-2) |  | p-Cl |
| 128-2) |  | p-Cl | 129-2) | CH₂CN | p-Cl |
| 131 | 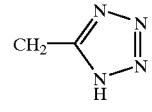 | p-Cl | 132-2) | 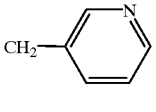 | p-Cl |

TABLE 7
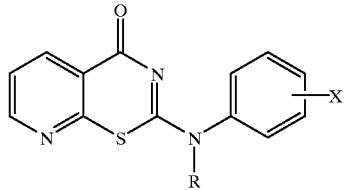
| Example | R | X | Example | R | X |
|---|---|---|---|---|---|
| 136-2) | 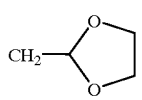 | p-Cl | 138 |  | p-Cl |
| 139 | CH₂CH₂CN | p-Cl | 140 | CH₂CH₂CH₂CN | p-Cl |
| 141 | CH₂(CH₂)₄CN | p-Cl | | | |
TABLE 8
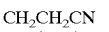
| Example | X | Example | X |
|---|---|---|---|
| 74 |  | 77 | 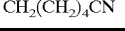 |
| 78 | 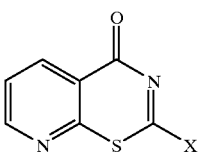 | 79 | 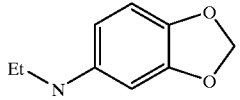 |
| 81 | 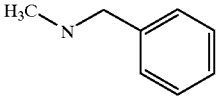 | 85 | 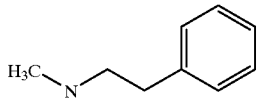 |
| 86 | 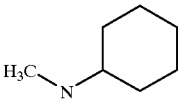 | 90 |  |
| 97 | 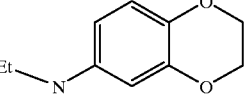 | 99 | 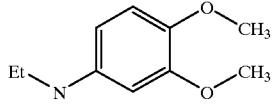 |
| 100 | 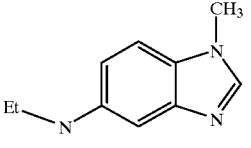 | 118 | 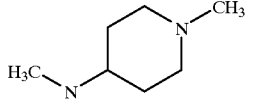 |

TABLE 9
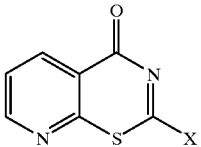
| Example | X | Example | X |
|---|---|---|---|
| 119 | 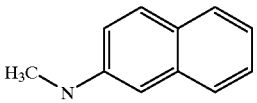 | 120 | 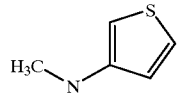 |
| 121 | 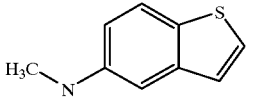 | 122 | 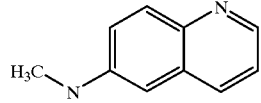 |
| 143 | 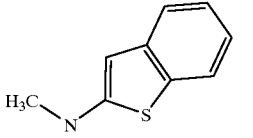 | | |
TABLE 10
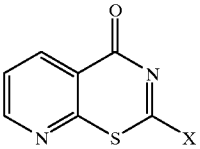
| Example | X | Example | X |
|---|---|---|---|
| 69 | 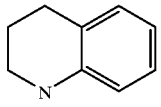 | 70 | 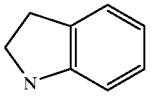 |
| 71 | 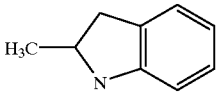 | 76 | 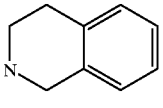 |
| 80 | 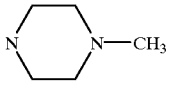 | 83 | 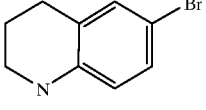 |
| 84 | 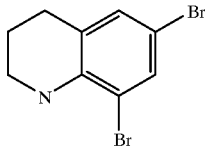 | 91 | 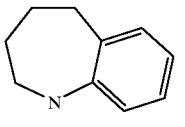 |

TABLE 10-continued

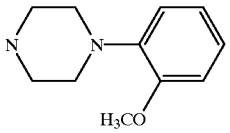

| Example | X | Example | X |
|---|---|---|---|
| 106 | 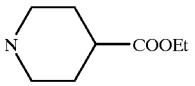 | 107 | 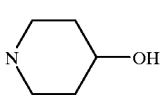 |

TABLE 11

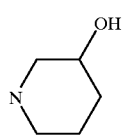

| Example | X | Example | X |
|---|---|---|---|
| 108 | 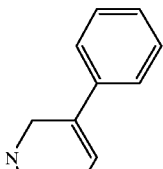 | 109 | 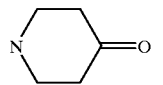 |
| 110 | 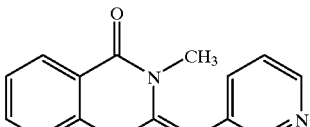 | 111 | 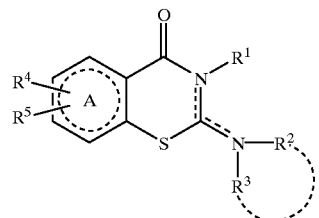 |

TABLE 12

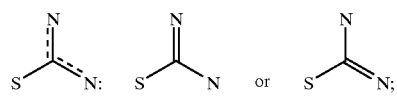

| Example | X | Y | Z | R |
|---|---|---|---|---|
| 82 | CH | C | N | CH₃ |
| 92 | CH | C | N | Ph |
| 95 | CH | N | CH | None |
| 96 | N | C | CH | H |

TABLE 13

| Example | Structural Formula |
|---|---|
| 101 | (structure) |

What is claimed is:

1. A composition for inhibiting kainic acid-induced neurotoxicity, which comprises as an active ingredients a pyridothiazine derivative represented by the following formula (I) or a pharmaceutically acceptable salt thereof, and a pharmaceutically acceptable carrier:

(I)

(structure)

wherein symbols in the formula have the following respective meanings:

the ring A: a pyridine ring;

(structures)

$R^1$ and $R^3$: one of them is not present and the other represents;

R²: a group represented by the formula

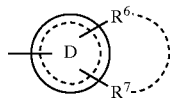

the ring D: a 5- or 6-membered aromatic ring which may have one or two of one or more types of hetero atoms selected from the group consisting of a nitrogen atom, an oxygen atom and a sulfur atom;

R⁶ and R⁷: may be the same or different and each represent a hydrogen atom, a lower alkyl group which may have substituent(s), a lower alkanoyl group, a cycloalkyl group, an aryl group, a hydroxyl group, a lower alkoxy group, a halogeno-lower alkoxy group, a carboxyl group, a lower alkoxycarbonyl group, a halogen atom, a nitro group, a cyano group, an amino group, a mono- or di-lower alkylamino group, a hydroxylamino group or a lower alkoxyamino group, wherein R⁶ and R⁷ may form together with the ring D an 8- to 11-membered bicyclo ring which may have from one to four of one or more types of hetero atoms selected from the group consisting of a nitrogen atom, an oxygen atom and a sulfur atom and may have a lower alkyl group as a substituent);

wherein R² and R³ may together form a 5- to 7-membered nitrogen-containing heterocyclic group which is fused with a benzene ring which may have substituent(s), which may have a nitrogen atom as another hetero atom, and which may have substituent(s); and R⁴ and R⁵: may be the same or different and each represent a hydrogen atom, a lower alkyl group or an aryl group; with the proviso that when one of R¹ and R³ is a methyl group, then one of R⁶ and R⁷ represents a group other than a hydrogen atom.

2. A pyridothiazine derivative represented by the following formula (II) or a pharmaceutically acceptable salt thereof:

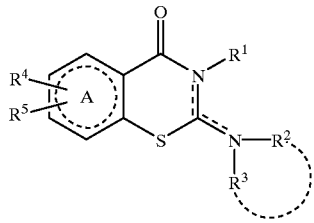 (II)

wherein symbols in the formula have the following respective meanings:

the ring A: a pyridine ring;

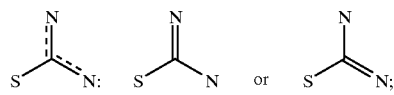

R¹ and R³: one of them is not present and the other represents;

R²: a group represented by the formula

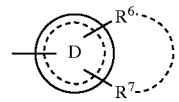

the ring D: a 5- or 6-membered aromatic ring which may have one or two of one or more types of hetero atoms selected from the group consisting of a nitrogen atom, an oxygen atom and a sulfur atom;

R⁶ and R⁷: may be the same or different and each represent a hydrogen atom, a lower alkyl group which may have substituent(s), a lower alkanoyl group, a cycloalkyl group, an aryl group, a hydroxyl group, a lower alkoxy group, a halogeno-lower alkoxy group, a carboxyl group, a lower alkoxycarbonyl group, a halogen atom, a nitro group, a cyano group, an amino group, a mono- or di-lower alkylamino group, a hydroxylamino group or a lower alkoxyamino group, wherein R⁶ and R⁷ may form together with the ring D an 8- to 11-membered bicyclo ring which may have from one to four of one or more types of hetero atoms selected from the group consisting of a nitrogen atom, an oxygen atom and a sulfur atom and may have a lower alkyl group as a substituent);

wherein R² and R³ may together form a 5- to 7-membered nitrogen-containing heterocyclic group which is fused with a benzene ring which may have substituent(s), which may have a nitrogen atom as another hetero atom, and which may have substituent(s); and R⁴ and R⁵: may be the same or different and each represent a hydrogen atom, a lower alkyl group or an aryl group;

with the proviso that when one of R¹ and R³ is a methyl group, then one of R⁶ and R⁷ represents a group other than a hydrogen atom.

3. The compound according to claim 2, wherein

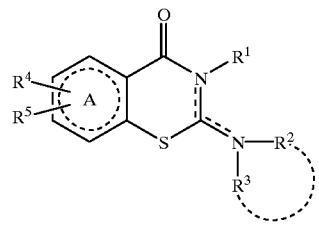

is a group represented by the formula:

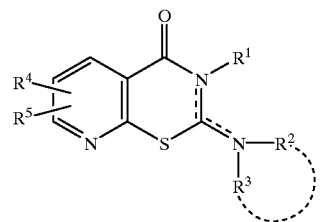

4. The compound according to claim 3, wherein R² is a group represented by the formula:

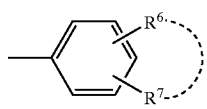

5. The compound according to claim 1 which is selected from the group consisting of 2-[N-methyl-N-(4-chlorophenyl)amino]-4H-pyrido[3,2-e]-1,3-thiazin-4-one, 2-[N-methyl-N-(4-bromophenyl)amino]-4H-pyrido[3,2-e]-1,3-thiazin-4-one, 2-[N-ethyl-N-(3,4-methylenedioxyphenyl)amino]-4H-pyrido[3,2-e]-1,3-thiazin-4-one, 2-[N-methyl-N-(4-trifluoromethoxylphenyl)amino]-4H-pyrido[3,2-e]-1,3-thiazin-4-one, 2-[N-(4-chlorophenyl)-N-(4-oxo-4H-pyrido[3,2-e]-1,3-thiazin-2-yl)amino]acetonitrile, 2-[N-(4-chlorophenyl)imino]-3-(2,3-dihydroxypropyl)-2,3-dihydro-4H-pyrido[3,2-e]-1,3-thiazin-4-one, and a pharmaceutically acceptable salt of these compounds.

6. A pharmaceutical composition which comprises a compound defined in any one of claims 2, 3, 4 and 5 and a pharmaceutically acceptable carrier.

7. A method of treatment comprising a compound for inhibiting kainic acid neurotoxicity according to claim 1, wherein said treatment comprises administering said compound to a subject in need of an AMPA receptor antagonist.

8. The method of treatment according to claim 7, comprising administering said compound to a subject diagnosed with a neurodegenerative disease, a psychiatric disease, pain, and glaucoma.

9. The method of treatment according to claim 8, comprising administering said compound to a subject diagnosed with Huntington's chorea, Parkinson's disease, epilepsy, Alzheimer's disease, senile dementia, cerebral ischemia, anoxia, diabetes, hypoglycemia, drug dependence, head injury, amyotrophic lateral sclerosis and multiple sclerosis.

* * * * *

UNITED STATES PATENT AND TRADEMARK OFFICE
CERTIFICATE OF CORRECTION

PATENT NO. : 6,133,258
DATED : October 17, 2000
INVENTOR(S) : Jun-ichi Shishikura, et al.

It is certified that error appears in the above-identified patent and that said Letters Patent is hereby corrected as shown below:

<u>Title page,</u>
Item [30], under Foreign Priority Data, delete "11/05/1995" and insert -- 11/15/1995 --.

Signed and Sealed this

Twenty-third Day of October, 2001

Attest:

*Nicholas P. Godici*

NICHOLAS P. GODICI
*Acting Director of the United States Patent and Trademark Office*

*Attesting Officer*